(12) United States Patent
Piomelli et al.

(10) Patent No.: US 8,003,693 B2
(45) Date of Patent: Aug. 23, 2011

(54) MODULATION OF ANXIETY THROUGH BLOCKADE OF ANANDAMIDE HYDROLYSIS

(75) Inventors: Daniele Piomelli, Irvine, CA (US); Andrea Duranti, Urbino (IT); Andrea Tontini, Pesaro (IT); Marco Mor, Ghedi (IT); Giorgio Tarzia, Petriano (IT)

(73) Assignees: The Regents of the University of California, Oakland, CA (US); Universita Degli Studi di Urbino, Urbino (IT); Universita Degl Studi di Parma, Parma (IT)

( * ) Notice: Subject to any disclaimer, the term of this patent is extended or adjusted under 35 U.S.C. 154(b) by 1230 days.

(21) Appl. No.: 11/496,051

(22) Filed: Jul. 28, 2006

(65) Prior Publication Data
US 2009/0048337 A1    Feb. 19, 2009

Related U.S. Application Data

(63) Continuation of application No. 10/681,858, filed on Oct. 7, 2003, now Pat. No. 7,176,201.

(60) Provisional application No. 60/417,008, filed on Oct. 7, 2002.

(51) Int. Cl.
    *A61K 31/27*    (2006.01)
(52) U.S. Cl. .................................................. 514/481
(58) Field of Classification Search .............. 560/115, 560/134; 558/234, 235; 514/481
    See application file for complete search history.

(56) References Cited

U.S. PATENT DOCUMENTS

| | | | |
|---|---|---|---|
| 2,776,197 A | 1/1957 | Gysin et al. | |
| 3,084,096 A * | 4/1963 | Lambrech | 514/480 |
| 3,275,512 A | 9/1966 | Lemin et al. | |
| 3,632,631 A | 1/1972 | Wright et al. | |
| 3,880,908 A | 4/1975 | Fields et al. | |
| 4,388,238 A | 6/1983 | Heitkamper et al. | |
| 4,987,233 A | 1/1991 | Achgill et al. | |
| 5,112,859 A | 5/1992 | Commons et al. | |
| 5,476,944 A | 12/1995 | Partis et al. | |
| 6,096,784 A | 8/2000 | Lerner et al. | |
| 6,251,931 B1 | 6/2001 | Boger et al. | |
| 6,271,015 B1 | 8/2001 | Gilula et al. | |
| 6,326,156 B1 | 12/2001 | Civelli et al. | |
| 6,359,010 B1 | 3/2002 | Geracioti, Jr. et al. | |
| 6,531,506 B1 * | 3/2003 | Kroetz et al. | 514/475 |
| 6,562,846 B2 | 5/2003 | Sit et al. | |
| 6,908,939 B2 | 6/2005 | Bernardon et al. | |
| 6,919,358 B2 | 7/2005 | Cheng et al. | |
| 6,927,228 B2 | 8/2005 | Bernardon et al. | |
| 7,176,201 B2 | 2/2007 | Piomelli et al. | |
| 2002/0187542 A1 | 12/2002 | Gilula et al. | |
| 2002/0188009 A1 | 12/2002 | Sit et al. | |
| 2003/0149082 A1 | 8/2003 | Makriyannis et al. | |
| 2003/0195226 A1 | 10/2003 | Sit et al. | |
| 2005/0137238 A1 | 6/2005 | Bernardon et al. | |

FOREIGN PATENT DOCUMENTS

| | | |
|---|---|---|
| DE | 4430 600 A1 | 2/1996 |
| EP | 0 027 952 A1 | 5/1981 |
| EP | 0 193 926 A2 | 3/1986 |
| EP | 0 428 385 A1 | 11/1990 |
| EP | 1 231 212 A1 | 8/2002 |
| HU | 197831 B | 7/1987 |
| JP | 8-92167 A | 4/1996 |
| WO | WO 96/02524 A1 | 2/1996 |
| WO | WO 98/22458 A1 | 5/1998 |
| WO | WO 98/24396 A2 | 6/1998 |
| WO | WO 00/48593 A1 | 8/2000 |
| WO | WO 02/08185 A1 | 1/2002 |
| WO | WO 02/12210 A1 | 2/2002 |
| WO | WO 02/14267 A1 | 2/2002 |
| WO | WO 02/087569 A | 11/2002 |

(Continued)

OTHER PUBLICATIONS

CAS Reg. No. 101192-00-1 (1986).*

(Continued)

*Primary Examiner* — Bernard Dentz
(74) *Attorney, Agent, or Firm* — Kilpatrick Townsend & Stockton LLP

(57) ABSTRACT

Fatty acid amide hydrolase inhibitors of the Formula:

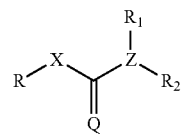

are provided wherein X is NH, $CH_2$, O, or S; Q is O or S; Z is O or N; R is an aromatic moiety selected from the group consisting of substituted or unsubstituted aryl; substituted or unsubstituted biphenylyl, substituted or unsubstituted naphthyl, and substituted or unsubstituted phenyl; substituted or unsubstituted terphenylyl; substituted or unsubstituted cycloalkyl, heteroaryl, or alkyl; and $R_1$ and $R_2$ are independently selected from the group consisting of H, substituted or unsubstituted alkyl, substituted or unsubstituted heteroalkyl, and substituted or unsubstituted phenyl, substituted or unsubstituted biphenylyl, substituted or unsubstituted aryl, and substituted or unsubstituted heteroaryl; with the proviso that if Z is O, one of $R_1$ and $R_2$ is absent, and that if Z is N, optionally $R_1$ and $R_2$ may optionally be taken together to form a substituted or unsubstituted N-heterocycle or substituted or unsubstituted heteroaryl with the N atom to which they are each attached. Pharmaceutical compositions comprising the compounds of Formula I and methods of using them to inhibit FAAH and/or treat appetite disorders, glaucoma, pain, insomnia, and neurological and psychological disorders including anxiety disorders, epilepsy, and depression are provided.

23 Claims, 9 Drawing Sheets

FOREIGN PATENT DOCUMENTS

| | | |
|---|---|---|
| WO | WO 03/051841 A2 | 6/2003 |
| WO | WO 03/051842 A2 | 6/2003 |
| WO | WO 03/065989 A2 | 8/2003 |

OTHER PUBLICATIONS

CAS Reg. No. 15300-40-0 (1984).*
CAS Reg. Mo. 3747-22-6 (1984).*
CAS Reg. No. 93817-28-8 (1984).*
CAS Reg. No. 1133-81-9 (1984).*
CAS Reg. No. 5289-06-5 (1984).*
CAS Reg. No. 5266-97-7 (1984).*
CAS Reg. No. 5241-91-8 (1984).*
CAS Reg. No. 5241-90-7 (1984).*
CAS Reg. No. 5241-89-4 (1984).*
CAS Reg. No. 3262-10-0 (1984).*
CAS Reg. No. 3201-09-0 (1984).*
CAS Reg. No. 21194-74-1 (1984).*
U.S. Appl. No. 60/336,289, filed Oct. 31, 2001, Piomelli et al.
Barnett-Norris, J. et al., "Conformational memories and the endocannabinoid binding site at the cannabinoid CB1 receptor" J. Med. Chem. 451:3649-3659 (2002).
Beltramo, M. et al., "Inhibition of anandamide hydrolysis in rat brain tissue by (E)-6-(bromomethylene) tetrahydro-3-(1-naphthalenyl)-2H-pyran-2-one" FEBS Lett. 403:263-267 (1997).
Bisogno, T. et al., "Fatty acid amide hydrolase, an enzyme with many bioactive substrates. possible therapeutic implications" Curr. Pharm. Des. 8:533-547 (2002).
Boger, D. et al., "Exceptionally potent inhibitors of fatty acid amide hydrolase: The enzyme responsible for degradation of endogenous oleamide and anadamide" Proc. Natl. Acad. Sci. USA 97:5044-5049 (2000).
Bracey, M. et al., "Structural adaptations in a membrane enzyme that terminates endocannabinoid signaling" Science 298:1793-1796 (2002).
Cravatt, B. et al., "Supersensitivity to anandamide and enhanced endogenous cannabinoid signaling in mice lacking fatty acid amide hydrolase" Proc. Natl. Acad. Sci. USA 98:9371-9376 (2001).
De Petrocellis, L. et al., "Novel inhibitors of brain, neuronal, and basophilic anandamide amidohydrolase" Biochem. Biophys. Res. Commun. 231:82-88 (1997).
Deutsch, D. et al., "Fatty acid sulfonyl fluorides inhibit anandamide metabolism and bind to the cannabinoid receptor" Biochem. Biophys. Res. Commun. 231:217-221 (1997).
Dinh, T. et al., "Brain monoglyceride lipase participating in endocannabinoid inactivation" Proc. Natl. Acad. Sci. USA 99:10819-10824 (2002).
Kathuria, S. et al., "Modulation of anxiety through blockade of anandamide hydrolysis" Nature Medicine 9(1):76-81 (2003).
Koutek, B. et al., "Inhibitors of arachidonoyl ethanolamide hydrolysis" J. Biol. Chem. 269:22937-22940 (1994).
Lopez-Rodriguez, M., et al., "Design, synthesis, and biological evaluation of new inhibitors of the endocannabinoid uptake: Comparison with effects on fatty acid amidohydrolase." J. Med. Chem. 46:1512-1522 (2003).
Piomelli, D. et al., "The endocannabinoid system as a target for therapeutic drugs" Trends Pharmacol. Sci. 21:218-224 (2000).
Quistad, G. et al., "Fatty acid hydrolase inhibition by neurotoxic organophosphorus pesticides" Toxicology and Applied Pharmacology 173:48-55 (2001).
Reggio, P. et al., "Conformational requirements for endocannabinoid interaction with the cannabinoid receeotirs, the anandamide transporter and fatty acid amidohydrolase" Chem. Phys. Lipids 108:15-35 (2000).
Smith, A., "Endocannabinoid System: FAAH better anxiolytics?" Nat. Rev. Drug Discov. 2:92 (2003).

Tarzia, G. et al., "Design, synthesis, and structure-activity relationships of alkylcarbamic acid aryl esters, a new class of fatty acid amide hydrolase inhibitors" J. Med. Chem. 46:2352-2360 (2003).
Wendeler, M. et al., "Inhibitors of endocannabinoid degradation: potential therapeutics for neurological disorders" Angew. Chem. Int. Ed. 42:2938-2941 (2003).
Barnes, J.H. et al., "The preparation and pharmacology of some phenolic carbamates and allophanates." J. Pharmacy Pharmacol., vol. 13, pp. 39-48, (1961).
Bisogno, T. et al., "Fatty acid amide hydrolase, an enzyme with many bioactive substrates. Possible therapeutic implications." Curr. Pharmaceut. Des., vol. 8, 533-47 (2002).
Brown, L.W. and A.A. Forist, "In vitro and in vivo hydrolysis of salicylanilide N-methylcarbamate and 4-biphenylyl N-methylcarbamate." J. Pharm. Sci., vol. 61, No. 6, pp. 858-860 (1972).
Kohn, G.K., et al., "Some structural relations of a group of simple alkylphenyl N-methylcarbamates to anticholinestrase activity." J. Agric. Food Chem., vol. 13, No. 3, pp. 232-235 (1965).
Lopez-Rodriguez, M.L. et al., "Design, synthesis, and biological evaluation of new inhibitors of the endocannabinoid uptake: Comparison with effects of fatty acid amidohydrolase." J. Med. Chem., vol. 46, No. 8, pp. 1512-1522 (2003).
Quesnelle, C.A. et al., "Directed ortho metalation—cross coupling connections. Nickel (0)-catalyzed cross coupling of aryl triflates with organozinc reagents." Synlett, vol. 5, No. 5, pp. 349-350 (May 1994).
Smith, A., "FAAH better anxiolytics?" Nature Reviews Drug Discovery vol. 2, p. 92 (2003).
Woods, G.F. et al., "M-diarylbenzenes." J. Am. Chem. Soc., vol. 73, pp. 3854-3856 (1951).
Woods, G.F., "Preparation and properties of some polyphenyls." WADC Technical Report, 59-496, pp. 1-170 (1959).
Foster, R.H.K. et al., "Studies in Analgesia: Piperidine Derivatives with Morphine-Like Activity," J. of Pharmacology., vol. 91, No. 3, pp. 195-209 (1947).
Koutek, B. et al., "Inhibitors of Arachidonoyl Ethanolamide Hydrolysis,", J. of Bio. Chem., Vo. 269, No. 37, pp. 22937-22940 (1994).
Noguchi, J. et al., "Synthetic method of protein analogs. IX. Preparation of polycapramide and poly-3-aminocaproyl-L-phenylalanine," Nippon Kagaku Zasshi, 76:646-648 (1955).
Wood, E., et al., "A prodrug approach to the design of cRaf1 kinase inhibitors with improved cellular activity," Anti-Cancer Drug Design, 16(1):1-6 (Feb. 2001).
Bal'on, Y., et al., Addition of N,N-Dichlorourethanes to Alkenes. . beta-Chloroalkyl Isocyanates.
Database Online, Chemical Abstracts Service on STN, comp. RN 195140-79-5 (entered in STN Oct. 9, 1997).
Database Online, ACS ON STN comp. RN 546141-08-6 (entered in STN Jul. 11, 2003).
Database Online, ACS ON STN comp. RN 546141-07-5 (entered in STN Jul. 11, 2003).
Effenberger, F., et al. "Die Umlagerung von Carbamidsaure-phenylestern-Synthesen von 2.4-Dioxo-3.4-dihydro-sH-1.3-benzoxazinen und Salicylamiden," Chemische Berichte, 1972, vol. 105, pp. 1926-1942.
Kawahara, M., et al. "An efficient synthesis of optically active physostigmine from tryptophan via alkylative cyclization." Organic Letters, 2000, vol. 2, No. 5, pp. 675-678.
Morisseau, C., et al. "Potent urea and carbamate inhibitors of soluble expoxide hydrolases," Proceedings of the National Academy of Sciences of USA, National Academy of Science, Washington, DC, US, 1999, vol. 96, pp. 8849-8854.
Tarzia, G., et al. "Design, synthesis, and structure-activity relationships of alkylcarbamic acid aryl esters, a new class of Fatty Acid Amide Hydrolase inhibitors," Journal of Medicinal Chemistry, 2003, vol. 46, No. 12, pp. 2352-2360.

* cited by examiner

MODULATION OF ANXIETY THROUGH BLOCKADE OF ANANDAMIDE HYDROLYSIS

RELATED APPLICATIONS

This application is a continuation of U.S. patent application Ser. No. 10/681,858, filed Oct. 7, 2003, which claims the benefit of U.S. Ser. No. 60/417,008, filed Oct. 7, 2002. This application is also related to U.S. application Ser. No. 10/112, 509, filed Mar. 27, 2003 and U.S. patent application Ser. No. 10/642,462, filed Aug. 15, 2003. The disclosures of each of which are incorporated in its entirety.

STATEMENT AS TO RIGHTS TO INVENTIONS MADE UNDER FEDERALLY SPONSORED RESEARCH OR DEVELOPMENT

This research was made, in part, with government support under Grant Nos. DA12413, DA 12447, and DA 12653 awarded by the National Institutes of Health which may have certain rights to the invention.

BACKGROUND OF THE INVENTION

Anxiety is a pathological counterpart of fear and is often accompanied by disturbances of mood, thinking, behavior, and physiology. Whereas fear is typically triggered by a perception of a threat in the environment, anxiety disorders typically involve a fearfulness which is either unprovoked by an environmental threat or highly disproportionate to an environmental threat.

Anxiety disorders are among the most common mental disorders and can greatly limit the quality of life. In an anxiety disorder, an extreme or pathological anxiety is generally the principal disturbance of mood or emotional tone. Such disorders include, but are not limited to, panic disorder (with and without a history of agoraphobia), agoraphobia (with and without a history of panic disorder), generalized anxiety disorder, specific phobia, social phobia, obsessive-compulsive disorder, acute stress disorder, and post-traumatic stress disorder. In addition, there are adjustment disorders with anxious features, anxiety disorders due to general medical conditions, substance-induced anxiety disorders, and the residual category of anxiety disorder not otherwise specified (See DSM-IV).

Cognitive-behavioral therapies can be beneficial for many patients with anxiety disorders (Chambless et al., 1998). Benzodiazepines, antidepressants, selective serotonin reuptake inhibitors and the novel compound buspirone (Lydiard et al., 1996) have been used with some success in the treatment of anxiety and anxiety disorders. Treatments combining psychotherapy and pharmacotherapy are also beneficial (March et al., 1997; American Psychiatric Association, 1998). One limitation of such psychotherapeutic treatments has been their cost and the reluctance of patients to enter such treatment. Many of the pharmaceutical treatments rely upon drugs, most particularly the important class of benzodiazepines, which have some addiction or abuse potential. As the anti-anxiety pharmacopeia is relatively bare, there is a need for additional therapeutic agents to treat anxiety and anxiety disorders.

Anxiety is one of the few mental disorders for which animal models are available. Researchers can reproduce symptoms of human anxiety in test animals by manipulating physical or psychosocial stressors. These animal models provide a means for screening compounds for anti-anxiety activity. In light of increasing awareness of numerous neurochemical alterations in anxiety disorders, many new classes of drugs are likely to be developed through such screening.

The psychoactive constituent of Cannabis, $\Delta^9$-tetrahydrocannabinol ($\Delta^9$-THC), produces in humans subjective emotional responses mediated by CB1 cannabinoid receptors, suggesting that endogenous cannabinoids may contribute to the regulation of mood and emotions. But the variable effects of $\Delta^9$-THC—which, depending on dosage, range from relaxation and euphoria to anxiety and panic attacks—obscure the interpretation of these results and limit the therapeutic potential of direct-acting cannabinoid agonists.

Anandamide, the naturally occurring amide of arachidonic acid with ethanolamine, meets all key criteria of an endogenous cannabinoid substance (Devane, W. A. et al. *Science*, 258, 1946-1949 (1992)): it is released upon demand by stimulated neurons (Di Marzo, V. et al., *Nature*, 372, 686-691 (1994); Giuffrida, A. et al., *Nat. Neurosci.*, 2, 358-363 (1999)); it activates cannabinoid receptors with high affinity (Devane, W. A. et al. *Science*, 258, 1946-1949 (1992)) and it is rapidly eliminated through a two-step process consisting of carrier-mediated transport followed by intracellular hydrolysis (Di Marzo, V. et al., *Nature*, 372, 686-691 (1994); Beltramo, M. et al., *FEBS Lett.*, 403, 263-267 (1997)). Anandamide hydrolysis is catalyzed by the enzyme fatty acid amide hydrolase (FAAH), a membrane-bound serine hydrolase (Cravatt, B. F. et al., *Nature*, 384, 83-87 (1996); Patricelli, M. P. et al., *Biochemistry*, 38, 9804-9812 (1999)) (WO 98/20119) (U.S. Pat. No. 6,271,015) that also cleaves other bioactive fatty ethanolamides, such as oleoylethanolamide (cis-9-octadecenamide)) (Rodriguez de Fonseca, F. et al. *Nature*, 414, 209-212 (2001)) and palmitoylethanolamide (Calignano, A. et al., *Nature*, 394, 277-281 (1998)). Mutant mice lacking the gene encoding for FAAH cannot metabolize anandamide (Cravatt, B. F. et al., *Proc. Natl. Acad. Sci. U.S.A.*, 98, 9371-9376 (2001)) and, though fertile and generally normal, show signs of enhanced anandamide activity at cannabinoid receptors, such as reduced pain sensation (Cravatt, B. F. et al., *Proc. Natl. Acad. Sci. U.S.A.*, 98, 9371-9376 (2001)). This suggests the possibility that drugs targeting FAAH may heighten the tonic actions of anandamide, while possibly avoiding the multiple, often unwanted effects produced by $\Delta^9$-THC and other direct-acting cannabinoid agonists (Hall, W., et al., *Lancet*, 352, 1611-1616 (1998); Chaperon, F., et al., *Crit. Rev. Neurobiol.*, 13, 243-281 (1999)).

Most current inhibitors of the FAAH enzyme lack the target selectivity and biological availability needed for in vivo studies (Koutek, B. et al., *J. Biol. Chem.*, 269, 22937-22940 (1994); De Petrocellis, L. et al., *Biochem. Biophys. Res. Commun.*, 231, 82-88 (1997); Deutsch, D. G. et al., *Biochem. Biophys. Res. Commun.*, 231, 217-221 (1997); Beltramo, M. et al., *FEBS Lett.*, 403:263-267 (1997)), while newer compounds, though promising, have not yet been characterized (Boger, D. L. et al. *Proc. Natl. Acad. Sci. U.S.A.*, 97, 5044-5049 (2000)). Thus, the therapeutic potential of FAAH inhibition with respect to the endogenous cannabinoid system activity remains essentially unexplored.

The present invention expands the pharmacopeia for the inhibition of FAAH and the treatment of anxiety and other conditions by providing a new class of FAAH inhibitors and new methods for treating anxiety and anxiety disorders or conditions by administering FAAH inhibitors.

BRIEF SUMMARY OF THE INVENTION

The invention provides novel compounds for inhibiting Fatty Acid Amide Hydrolase (FAAH) and methods of treating anxiety or pain, and other neurological, sleep, or psychological disorders, for inducing sleep, for treating glaucoma, and controlling appetite or treating appetive disorders by administering FAAH inhibitors to a subject. In one of its aspects the invention discloses the use of FAAH inhibitors as useful in treating anxiety and depression. In another of its aspects the invention provides FAAH inhibitory compounds of the following Formula:

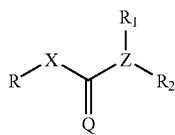

in which X is $CH_2$, NH, O, or S; Q is O or S; Z is O or N, with the proviso that when Z is O, one of $R_1$ and $R_2$ is absent; and R is an aromatic or alkyl or lipophilic moiety selected from the group consisting of substituted or unsubstituted aryl; substituted or unsubstituted biphenylyl, substituted or unsubstituted naphthyl, and substituted or unsubstituted phenyl; substituted or unsubstituted terphenylyl; substituted or unsubstituted cycloalkyl, substituted or unsubstituted heteroaryl, substituted or unsubstituted alkyl; substituted or unsubstituted heteroalkyl, and

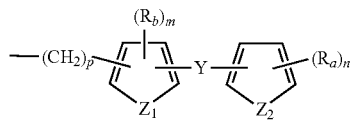

wherein p is a number from 0 to 3; m is a number from 0 to 4, and n is a number from 0 to 5, $Z_1$ and $Z_2$ are same or different and are independently a divalent radical selected from the group consisting of —O—, —S—, —N($R_5$)—, —C($R_6$)=C($R_7$)—, C($R_6$)=N— and —N=C($R_6$)— wherein $R_5$ is selected from H, alkyl, heteroalkyl, alkenyl, alkynyl, cycloalkyl, aryl, acyl and aroyl; $R_6$ and $R_7$ are H or $R_6$ and $R_7$ optionally may combine to form a saturated or unsaturated carbocyclic or heterocyclic ring, optionally substituted with one or more $R_a$ and $R_b$ groups; Y is a bond, or a divalent radical selected from the group consisting of —O—, —S—, —N($R_5$)—, $C_1$-$C_4$ alkylene, (Z)- or (E)-ethylene, and cycloalkyl with 3 to 6 carbon atoms; $R_a$ and $R_b$ are independently selected from the group consisting of H, alkyl, heteroalkyl, alkenyl, alkynyl, cycloalkyl, aryl, substituted aryl, arylalkyl, substituted arylalkyl, ketoalkyl, hydroxyalkyl, aminoalkyl, —$CH_2$—$NR_3R_4$, alkoxy, aryloxy, arylalkyloxy, halo, haloalkyl, cyano, hydroxy, nitro, amino, —$NR_3R_4$, —$SR_5$, carboxamido, —$CONR_3R_4$, —O-carboxamido, —O—CO—$NR_3R_4$, sulfonamido, and —$SO_2NR_3R_4$, wherein $R_3$ and $R_4$ are selected from H, alkyl, alkenyl, alkynyl, cycloalkyl, hydroxyalkyl and imino-methylamino and wherein optionally $R_3$ and $R_4$ together with the N atom to which they are attached to form a 5-7 membered cyclic ring.

In addition, $R_1$ and $R_2$ are independently selected from the group consisting of H, substituted or unsubstituted alkyl, substituted or unsubstituted heteroalkyl, substituted or unsubstituted cycloalkyl, and substituted or unsubstituted cycloheteroalkyl, and substituted or unsubstituted phenyl, and substituted or unsubstituted aryl or heteroaryl, and wherein optionally, when X is N, if taken together with the N atom to which they are attached, $R_1$ and $R_2$, form a substituted or unsubstituted N-heterocycle or substituted or unsubstituted heteroaryl with the atom to which they are each attached.

In one aspect, the invention provides compounds in which R and not —$NR_1R_2$ provides the majority the hydrophobic bulkiness needed to occupy a hydrophobic channel in FAAH as set forth in Example 18. In particular embodiments, for instance, when $R_1$ and/or $R_2$ is substituted aryl or heteroaryl or comprises a bulky aromatic ring, R represents a substituent which has a greater mass or weight than —$NR_1R_2$. Other embodiments include, but are not limited to, compounds in which R has a greater mass or molecular weight than —$NR_1R_2$ when $R_1$ and $R_2$ taken alone or together do not comprise any aryl, heteroaryl, or aromatic rings. In some embodiments, a compound with a FAAH $IC_{50}$ of less than 1 micromolar can have a surprisingly small —$NR_1R_2$ moiety. For instance, such an inhibitor can have a molecular weight of less than 200 or 100 Daltons or be no larger in bulkiness than a $C_7$ cycloalkyl or $C_6$ or $C_{10}$ alkyl group when R is as described above. In another aspect, the compounds of the invention include compounds which interact more with the hydrophobic channel of FAAH instead of the catalytic site of the enzyme to support their binding. Exemplary such compounds have a hydrophilic moiety distal to the carbamate end of the molecule and separated there from by a lipophillic moiety occupying the hydrophilic channel of the enzyme.

In one embodiment, the inhibitor of Formula I has an $IC_{50}$ of less than 1 µM. In one embodiment the inhibitor Formula I has an $IC_{50}$ of less than 0.01 µM. In another embodiment, the inhibitor Formula I has an $IC_{50}$ of from about 1 µM to about 0.01 µM, or from about 0.01 to about 0.001 µM.

In one embodiment the FAAH inhibitor is a compound of Formula II:

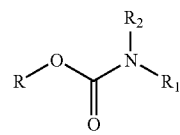

in which $R_1$, $R_2$ and R are defined as recited above.

In one embodiment of a compound of Formula II, $R_1$ is H and $R_2$ is cyclohexyl. In another embodiment, R is substituted or unsubstituted biphenylyl. In a further embodiment, $R_1$ is H, $R_2$ is cyclohexyl and R is substituted or unsubstituted biphenylyl or substituted or unsubstituted phenyl.

In one embodiment, such an inhibitor or compound according to Formula I or II has a FAAH $IC_{50}$ of less than 1 µM. In another embodiment the inhibitors have a FAAH $IC_{50}$ of less than 0.01 µM. In another embodiment, the inhibitors have a FAAH $IC_{50}$ of from about 1 µM to about 0.01 µM, or from about 0.01 to about 0.001 µM.

In yet another embodiment of a compound in which X is O, Q is O; and Z is N; $R_1$ is H and $R_2$ is $C_1$ to $C_8$ alkyl. In a further embodiment, R is substituted or unsubstituted biphenylyl, terphenylyl, or stilbyl.

In another aspect, the invention provides FAAH inhibitors and compounds of the following general formula:

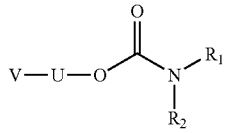

In Formula III, $R_1$ and $R_2$ are independently selected from the group consisting of H, unsubstituted or substituted homoalkyl, substituted or unsubstituted heteroalkyl, substituted or unsubstituted cycloalkyl, substituted or unsubstituted heterocycloalkyl, and optionally $R_1$ and $R_2$, may be taken together to form a substituted or unsubstituted heterocycle with N; U is a hydrophobic spacer, wherein the spacer comprises substituted or unsubstituted aryl; and V is a hydrophilic moiety having at least one functional group capable of forming a hydrogen bond. In addition, the hydrophobic spacer is at least 9 angstroms in length; and the hydrophilic moiety is attached to the spacer at a point from 8 to 12 angstroms distant from a point at which the hydrophobic spacer is covalently attached to the rest of the inhibitor.

In a further embodiment, the inhibitor or compound of Formula III has a hydrophobic spacer comprising a first and a second aromatic ring, wherein the first and second aromatic rings are covalently attached by a linker selected from the group consisting of a bond, a single heteroatom, and substituted or unsubstituted $C_1$ to $C_4$ alkylene.

In another embodiment, V is selected from the group consisting of ketoalkyl, hydroxyalkyl, aminoalkyl, —$CH_2$—$NR_3R_4$, alkoxy, aryloxy, halo, haloalkyl, cyano, hydroxy, nitro, amino, —$NR_3R_4$, carboxamido, —$CONR_3R_4$, —O-carboxamido, —O—CO—$NR_3R_4$, sulfonamido, and —$SO_2NR_3R_4$; in which $R_3$ and $R_4$ are selected from H, alkyl, heteroalkyl, alkenyl, alkynyl, cycloalkyl, hydroxyalkyl and imino-methylamino or $R_3$ and $R_4$ may optionally combine with the N atom to which they are attached to form a 5-7 membered cyclic ring.

In another embodiment, U and V are each set forth as described above and the hydrophilic moiety is attached to the spacer at a point about 9 to 11 angstroms from a point at which the spacer is covalently attached to the rest of the inhibitor. In a further embodiment, the hydrophilic moiety is attached to the spacer at a point about 10 angstroms from a point at which the spacer is covalently attached to the rest of the inhibitor.

In one embodiment, U and V taken together have a greater mass than the remainder of the molecule or than the —$NR_1R_2$ moiety.

In yet another embodiment, the hydrophobic spacer occupies the central hydrophobic channel of the FAAH enzyme as set forth in Example 18 and is of sufficient length to allow an appropriately positioned V group to engage in hydrogen bonding at a hydrophilic site at the indicated hydrophilic wall of the channel and distal to the carbamate moiety binding site.

In another embodiment, the compound of Formula I or Formula II or Formula III is a FAAH inhibitor which is selective for FAAH as compared to the neurotoxic esterase (NTE) or acetylcholinesterase (ACHE). In one embodiment, the compound has an FAAH $IC_{50}$ which is one-tenth to one-hundredth that for the NTE or ACHE $IC_{50}$.

In one embodiment, such an inhibitor according to Formula I, II, or III has an $IC_{50}$ of less than 1 µM. In still another embodiment, the inhibitor according to Formula I, II, or III has an $IC_{50}$ of less than 0.01 µM. In yet another embodiment, the inhibitor according to Formula I, II, or III has an $IC_{50}$ of from about 1 µM to about 0.01 µM, or from about 0.01 to about 0.001 µM.

In one embodiment, the inhibitor of Formula I, II or III is a selective inhibitor of FAAH over any one of electric eel ACHE, rat brain monoglyceride lipase, or horse plasma butyryl cholinesterase. In further embodiments, the selective inhibitor has an $IC_{50}$ for inhibition of FAAH that is no more than one-fifth, one-tenth, or one-twentieth its $IC_{50}$ for inhibition of electric eel ACHE, rat brain monoglyceride lipase, or horse plasma butyryl cholinesterase.

In one embodiment, the inhibitor of Formula I, II or III is a selective inhibitor of FAAH which does not substantially directly interact with the CB1 or the CB2 cannabinoid receptor at the $IC_{50}$ concentrations for inhibition of FAAH. In further embodiments, the binding $IC_{50}$ for inhibiting the binding of an agonist of the CB1 or CB2 cannabinoid receptor is at least 10 or 20 or 100 times greater than the $IC_{50}$ for inhibiting FAAH.

In one embodiment, a compound of the Formula I or II or III is contacted with FAAH to inhibit the FAAH enzyme. In a further embodiment, the enzyme is contacted in vivo. In a second further embodiment, the enzyme is contacted in vitro with a compound of Formula I, II, or III.

In one aspect, the invention provides novel carbamate inhibitors of FAAH and their use in inhibiting FAAH. In one embodiment, a compound of the Formula I, II, or III is contacted with a FAAH to inhibit the enzyme. In a further embodiment, the enzyme is contacted in vivo. In another embodiment, the enzyme is contacted in vitro with a compound of Formula I, II, or III.

In another aspect, the invention provides a method of treating anxiety, an anxiety disorder, or a psychological disorder associated with anxiety by administering an inhibitor of a FAAH inhibitor to a subject having one or more of such conditions. In another embodiment, such a subject is not otherwise in need of treatment with a FAAH inhibitor. In another embodiment, the subject with one of such conditions is not in need of a sleep-inducing agent or pain relief. In another embodiment, the FAAH inhibitor is selective for FAAH as compared to the neurotoxic esterase (NTE) or acetylcholinesterase (ACHE).

In one embodiment, a FAAH inhibitor is administered to a subject to treat anxiety or an anxiety disorder. In a further embodiment, a compound according to Formula I or Formula II or Formula III is administered to treat anxiety or an anxiety disorder. In a further embodiment, the compound to be administered to treat anxiety or an anxiety disorder is UCM532 or UCM597. In a further embodiment, the subject is not otherwise in need of treatment with a FAAH inhibitor. In another embodiment, the subject to be treated is not in need of a sleep-inducing agent or pain relief, including but not limited to neuropathic pain. In another embodiment, the FAAH inhibitor is formulated with an antianxiety compound which is not a FAAH inhibitor and/or administered as part of a combination therapy with such an antianxiety compound.

In one embodiment, a FAAH inhibitor is administered to a subject to treat depression or a depressive disorder. In a further embodiment, a compound according to Formula I, II, or III is administered to treat such depression or disorder. In a further embodiment, the compound to be administered to treat such depression or disorder is UCM532 or UCM597. In another embodiment, such a subject is not otherwise in need of treatment with a FAAH inhibitor. In another embodiment, the subject is not in need of sleep-inducing agent or pain relief. In another embodiment, the FAAH inhibitor is formulated with a second antidepressant which is not a FAAH inhibitor or administered as part of a combination therapy with such an antidepressant.

In another aspect, the invention provides a method of treating epilepsy by administering a FAAH inhibitor to a subject with epilepsy. In one embodiment, a compound according to Formula I, II, or III is administered to treat epilepsy. In another embodiment, the subject is also treated with an additional anti-epilepsy compound which is not an FAAH inhibitor. In another embodiment, the compound according to Formula I is UCM532 or UCM597. In another embodiment, the FAAH inhibitor is administered or formulated with a second compound which is not a FAAH inhibitor.

In one aspect of the instant invention, methods are provided for reducing appetite, body fat or body weight, or for treating or preventing obesity or overweight, or for reducing food intake, or treating an appetency disorder in a mammal by administering to the mammal a FAAH inhibitor to reduce an appetite or the consumption of an appetizing substance such as food. In some embodiments, the compound is a compound of Formula I, II, or III.

In another aspect the invention provides methods of identifying anxiolytic FAAH inhibitors by administering the inhibitor to a test subject; exposing the subject to an anxiety-causing stimulus; and measuring the degree of anxiety in the exposed test subject. In one embodiment, the invention provides a method of determining whether a compound is an anxiolytic fatty acid amide hydrolase inhibitor by contacting the compound with a fatty acid amide hydrolase enzyme under enzymatic assay conditions and selecting the compound if it is a fatty acid amide hydrolase inhibitor; and then determining if the selected compound is an anxiolytic fatty acid amide hydrolase enzyme inhibitor by administering the inhibitor to a test subject; exposing the subject to an anxiety-causing stimulus; and measuring the degree of anxiety in the exposed test subject. In one embodiment, such an inhibitor is a compound of Formula I, II, or III.

In another aspect the invention provides methods for identifying an anti-depressant or an anti-epilepsy FAAH inhibitor by administering the inhibitor to a test subject in an animal model for depression or epilepsy, respectively, and measuring the performance of the test subject according to the test. In one embodiment, the invention provides a method of determining whether a compound is an anti-depressant or an anti-epileptic fatty acid amide hydrolase inhibitor by contacting the compound with a fatty acid amide hydrolase enzyme under enzymatic assay conditions and selecting the compound if it is a fatty acid amide hydrolase inhibitor; and then determining if the selected compound is an anti-depressant or anti-epileptic fatty acid amide hydrolase enzyme inhibitor by administering the inhibitor to a test subject in an animal model for depression or epilepsy, respectively. In one embodiment, such an inhibitor is a compound of Formula I, II, or III.

In one embodiment, a FAAH inhibitor is administered to a subject to treat schizophrenia or paranoia or a related disorder or a disorder of dopamine transmission. In a further embodiment, a compound according to Formula I, II, or III is administered to treat such diseases or conditions. In a further embodiment, the compound to be administered is UCM532 or UCM597. In one embodiment, the FAAH inhibitor is formulated or administered with or given as part of a combination therapy with a second anti-psychotic agent which is not a FAAH inhibitor.

In still another aspect, the invention provides a pharmaceutical composition comprising a compound of Formula I, II, or III and a pharmaceutically acceptable excipient. In another aspect, the invention provides methods of treating depression, anxiety, insomnia, pain, schizophrenia, epilepsy, glaucoma, or an appetite disorder by administering such a composition to a subject. In one embodiment, the invention provides pharmaceutical doses in unit dosage format comprising a therapeutically effective amount of the FAAH inhibitor. In some embodiments, the therapeutically effect is in an amount sufficient to treat one of the above psychological conditions or disorders. In one embodiment, the therapeutically effect is in an amount sufficient to treat anxiety or an anxiety disorder in a subject. In other embodiments, the treated subject is a human with acute anxiety, chronic anxiety, or an anxiety disorder. In other embodiments, the unit dosage of the FAAH inhibitor is in an amount sufficient to treat a human with depression or a depressive disorder.

In still other aspects the invention provides a method of modulating endogenous fatty acid amide levels in a subject by administering a compound of Formula I, II, or III to a subject. In one such embodiment, the modulating reduces anxiety in said subject. In another embodiment, the modulating reduces sensitivity to pain in the subject. In another embodiment, the modulating does not induce catalepsy. In another embodiment, the modulating does not induce hyperphagia or affect appetite.

In another aspect, the invention also provides methods for increasing the levels of endogenous anandamide, endogenous oleoylethanolamide, and other endogenous fatty acid amides in a subject by administering a compound of Formula I, II, or III. The invention also provides methods for increasing the levels (e.g., blood, plasma, brain or other tissue concentrations) or biological activity (e.g., therapeutic activity, FAAH inhibitory activity) of administered or exogenous anandamide, oleoylethanolamide, and fatty acid amides in a subject by administering a compound of Formula I, II, or III.

Figure 1:
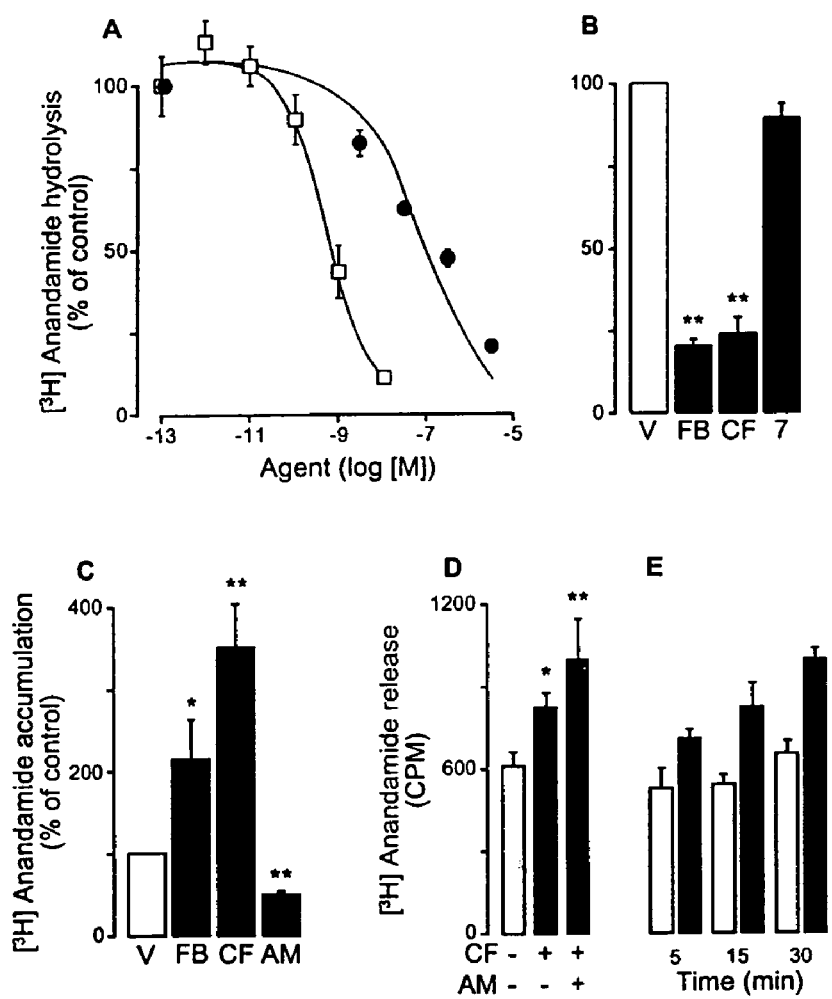
FIG. 1. The FAAH inhibitors UCM532 and UCM597 block [$^3$H]anandamide degradation in intact brain neurons. a, Concentration-dependent inhibition of [$^3$H]anandamide hydrolysis by UCM597 (open squares) and UCM532 (closed circles) in primary cultures of rat cortical neurons. b, Unlike UCM532 (FB, 3 μM) or UCM597 (CF, 10 nM), the UCM532 analog 7 (10 μM) has no effect on [$^3$H]anandamide degradation. c, UCM532 (FB, 3 μM) and UCM597 (CF, 10 nM) promote accumulation of non-metabolized [$^3$H]anandamide in neurons, whereas the anandamide transport inhibitor AM404 (AM, 10 μM) reduces it. d, Release of non-metabolized [$^3$H]anandamide from UCM597-treated (10 nM) neurons during a 15-min incubation in the absence or presence of AM404 (AM, 10 μM). e, Time course of [$^3$H]anandamide release from UCM597-treated (10 nM) neurons. One asterisk, $P<0.05$; two asterisks, $P<0.01$ versus vehicle-treated neurons; ANOVA with Tukey's post-hoc test (n=4-8).

Table 1. Values reported are the concentrations required to inhibit FAAH activity by 50% (IC$_{50}$, nM), and are expressed as the mean±SEM of at least three independent experiments. They were calculated from concentration-response curves, by using non-linear regression analysis as implemented in the Prism 2.0 software package.

Table 2. Values indicate the maximal concentrations of FAAH inhibitor tested on each target (in μM) and their corresponding selectivity index (SI). The SI is the ratio of maximal inhibitor concentration tested/IC$_{50}$ for FAAH (from Table 1).

Table 3. FAAH and acetylcholinesterase IC$_{50}$ values are reported for 18 compounds, including carbaryl and physostigmine.

Table 4. FAAH IC$_{50}$ values are reported for over 50 compounds of Formula I.

Table 5. FAAH IC$_{50}$ values are reported for over 20 meta biphenyl compounds.

Table 6. Observed and calculated pIC50 values for FAAH inhibition of the meta substituted derivatives included in the QSAR analysis.

DETAILED DESCRIPTION OF THE INVENTION

In one aspect, the invention provides novel inhibitors of fatty acid amide hydrolase (FAAH), the enzyme responsible for the intracellular degradation of the endogenous cannabinoid anandamide. The inventors have surprisingly discovered compounds that inhibit FAAH in vivo with a low IC$_{50}$. Exemplary compounds according to the invention can be potent, selective, systemically active inhibitors of FAAH. FAAH inhibitors can be useful for a variety of purposes such as the induction of sleep, treatment of insomnia, and the alleviation of pain. The invention also provides a means of treating anxiety by administering FAAH inhibitors. Like clinically used anti-anxiety drugs, such inhibitors surprisingly exhibit benzodiazepine-like properties in the elevated zero-maze test and suppress isolation-induced vocalizations in rats. Furthermore, they reduce nocifensive (pain-avoiding) behaviors in models of acute pain. These effects have been accompanied by augmented brain levels of anandamide, but not of the other endogenous cannabinoid 2-arachidonoylglycerol, and are prevented or antagonized by CB1 cannabinoid receptor blockade. The results show that anandamide participates in the modulation of emotional states, and point to FAAH inhibition as an innovative mechanistic approach to anti-anxiety therapy.

FAAH inhibitors can be also useful in the treatment of a variety of other neurological psychological disorders and conditions, including but not limited to pain, depression, attention deficit hyperactivity disorders, jet lag, insomnia, schizophrenia, pain, muscle spasticity, epilepsy, and seizure disorders as well as glaucoma.

The invention also provides methods for increasing the levels of endogenous anandamide, endogenous oleoylethanolamide, and other endogenous fatty acid amides in a subject by administering a compound of Formula I or Formula II. The invention also provides methods for increasing the levels and biological activity of administered anandamide, oleoylethanolamide, and fatty acid amides in a subject by also administering (e.g., prior administration, contemporaneous administration, co-administration) to the subject a FAAH inhibitor of Formula I or Formula II. Thus, the FAAH inhibitors of Formula I and II can be useful in potentiating the biological activity of anandamide or oleoylethanolamide.

The invention provides a new class of agents that prevent anandamide or oleoylethanolamide inactivation by targeting the intracellular enzymatic activity of FAAH.

The invention provides further a novel class of inhibitors of FAAH activity, which enhance endogenous anandamide signaling. The behavioral profile of these agents—characterized by anxiolysis and mild analgesia—reveal a key role for anandamide in the regulation of emotional states and provide a new mechanistic approach to anti-anxiety therapy in particular.

The invention also provides a means of inhibiting FAAH by contacting the enzyme in vitro or in vivo with an inhibitor or compound according to the invention (e.g., compounds of Formula I, Ia-c, I, IIa-b, and III). The enzyme is preferably mammalian (e.g., rat, human, mouse, dog, cat, domesticated species of mammals).

DEFINITIONS

It is noted here that, as used in this specification, the singular forms "a," "an," and "the" include plural reference unless the context clearly dictates otherwise.

Unless otherwise defined, all technical and scientific terms used herein have the same meaning as commonly understood by one of ordinary skill in the art to which this invention belongs. Each publication, patent application, patent, and other reference cited herein is incorporated by reference in its entirety to the extent that it is not inconsistent with the present disclosure.

In the present description and in the claims, "appetency disorders" are understood as meaning disorders associated with a substance and especially abuse of a substance and/or dependency on a substance, disorders of food behaviors, especially those liable to cause excess weight, irrespective of its origin, for example: bulimia, appetency for sugars, non-insulin-dependent diabetes. Appetizing substances are therefore understood as meaning substances to be taken into the body and for which an appetite or craving for such consumption is present by any route of entry or self-administration. Appetizing substances includes, foods, and their appetizing ingredients such as sugars, carbohydrates, or fats, as well as drinking alcohol or drugs of abuse or excess consumption. An "appetite" may be directed toward such substances as foods, sugars, carbohydrates, fats, as well as ethanol or drugs of abuse or addiction or excess consumption (e.g., tobacco, CNS depressants, CNS stimulants).

Appetite refers to the desire to consume an appetizing substance or the behavior of consuming appetizing substances. An appetizing substance may be a food or sugar or other substance. In one embodiment, the appetizing substance is a food. In some embodiments, the appetizing substance is a drug of abuse such as ethanol, nicotine, cocaine, an opioid, a CNS stimulant or a CNS depressant.

Anxiety is a state of fearfulness which is unprovoked by an environmental threat or highly disproportionate to an environmental threat. Anxiety may be acute and short term lasting hours to days; or chronic and lasting from many days to weeks or longer.

The term clinical anxiety refers to any form of anxiety for which treatment is necessary or indicated in order to alleviate it. Such clinical anxiety may be persistent or recurrent and typically severe.

Anxiety disorders include, but are not limited to, any of the anxiety disorders as provided in the Diagnostic and Statistical Manual of Mental Disorders, Fourth Edition. (Copyright 1994 American Psychiatric Association) which is hereby incorporated by reference. Such disorders include, but are not limited to, panic disorder, agoraphobia, generalized anxiety disorder, specific phobia, social phobia, obsessive-compulsive disorder, acute stress disorder, and post-traumatic stress disorder; and adjustment disorders with anxious features, anxiety disorders due to general medical conditions, substance-induced anxiety disorders, and the residual category of anxiety disorder not otherwise specified.

Depressive disorders and conditions include, but are not limited to, any of the depressive disorders and conditions as provided in the Diagnostic and Statistical Manual of Mental Disorders, Fourth Edition (Copyright 1994 American Psychiatric Association). These disorders include major depressive disorder (unipolar depression), dysthymic disorder (chronic, mild depression), and bipolar disorder (manic-depression). Clinical depression refers to any form of depression that requires some form of treatment in order to alleviate it. Such clinical depression may persist for months and last for most of every day and seriously impairs the quality of life.

A "major depressive episode" is defined as at least two weeks of depressed mood or loss of interest, which may be accompanied by other symptoms of depression. The symptoms must persist for most of the day (i.e. for at least two thirds of the patients' waking hours), nearly every day (i.e. for at least ten out of fourteen days) for at least two consecutive weeks. A "depressed mood" is often described by the patient as feeling sad, hopeless, helpless or worthless. The patient may also appear sad to an observer, for example, through facial expression, posture, voice and tearfulness. In children and adolescents, the mood may be irritable. A "loss of interest" is often described by the patient as feeling less interested in hobbies or not feeling any enjoyment in activities that were previously considered to be pleasurable.

A major depressive episode may be accompanied by other symptoms of depression including significant weight loss when not dieting or weight gain (e.g. a change of more than 5% body weight in one month), or decrease or increase in appetite; insomnia or hypersomnia; psychomotor agitation or retardation; fatigue or loss of energy; feelings of worthlessness or excessive or inappropriate guilt; diminished ability to think or concentrate; or indecisiveness; and recurrent thoughts of death, recurrent suicidal ideation with or without a specific plan, or a suicide attempt.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. The term "pharmaceutical composition" indicates a composition suitable for pharmaceutical use in a subject, including an animal or human. A pharmaceutical composition generally comprises an effective amount of an active agent and a pharmaceutically acceptable carrier.

The term "modulate" means to induce any change including increasing or decreasing. (e.g., a modulator of fatty acid oxidation increases or decreases the rate of fatty oxidation.)

The term "pharmaceutically acceptable carrier" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in Remington's Pharmaceutical Sciences (Mack Publishing Co., Easton, 19th ed. 1995). Preferred pharmaceutical carriers depend upon the intended mode of administration of the active agent. Typical modes of administration are described below.

The term "effective amount" means a dosage sufficient to produce a desired result with respect to the indicated disorder, condition, or mental state. The desired result may comprise a subjective or objective improvement in the recipient of the dosage. With respect to anxiety, the improvement may be decreased sign or symptom of anxiety.

The terms "treatment", "therapy" and the like include, but are not limited to, methods and manipulations to produce beneficial changes in a recipient's status. The changes can be either subjective or objective and can relate to features such as symptoms or signs of the disease, disorder or condition being treated. For example, if the patient notes decreased fearfulness, anxiety or worry, then successful treatment of anxiety or an anxiety disorder has occurred. For example, if a decrease in the frequency or severity of seizures is noted, then a beneficial treatment of epilepsy has occurred. For example, if depressive ideation is reduced, a beneficial change in depression or a depressive disorder has been achieved. Similarly, if the clinician notes objective changes, such as decreases in tremulousness or agitation, then treatment for anxiety has also been beneficial or successful. Preventing the deterioration of a recipient's status is also included by the term. Therapeutic benefit includes any of a number of subjective or objective factors indicating a response of the condition being treated as discussed herein.

"Drug", "pharmacological agent", "pharmaceutical agent", "active agent", and "agent" are used interchangeably and are intended to have their broadest interpretation as to any therapeutically active substance which is delivered to a living organism to produce a desired, usually beneficial effect.

"Pharmaceutically-acceptable" or "therapeutically-acceptable" refers to a substance which does not interfere with the effectiveness or the biological activity of the active ingredients and which is not toxic to the hosts, which may be either humans or animals, to which it is administered.

"Therapeutically-effective amount" refers to the amount of an active agent sufficient to induce a desired biological or clinical result. That result may be alleviation of the signs, symptoms, or causes of a disease, or any other desired alteration of a biological system. The term "therapeutically effective amount" is used herein to denote any amount of the formulation which causes a substantial improvement in a disease, disorder or condition when administered to a subject over a period of time. The amount will vary with the condition being treated, the stage of advancement of the condition, and the type and concentration of formulation applied. Appropriate amounts in any given instance will be readily apparent to those skilled in the art or capable of determination by routine experimentation.

A "prophylactic treatment" is a treatment administered to a subject who does not exhibit signs of a neurological or psychological disorder or condition or exhibits only early or slight signs of such a disorder or condition, wherein treatment is administered for the purpose of decreasing the risk of developing a pathology or worsening of disorder or condition. The compounds of the invention may be given as a prophylactic treatment to prevent undesirable or unwanted anxiety or panic attacks, or to reduce the level of anxiety should worsening occur.

The term "subject" as used herein includes any animal, including, but not limited to, mammals (e.g., rat, mouse, cat, dog) including humans to which a treatment is to be given.

Schizophrenia and related disorders include, but are not limited to the following types: Catatonic Type; Disorganized Type; Paranoid Type; Residual Type; Undifferentiated Type; and Schizophreniform Disorder as provided in the Diagnostic and Statistical Manual of Mental Disorders, Fourth Edition. TEXT REVISION Copyright 2000 American Psychiatric Association which is hereby incorporated be reference.

"FAAH" denotes a mammalian Fatty Acid Amide Hydrolase and includes, but is not limited to, the human, rat, mouse forms of the enzyme. U.S. Pat. No. 6,271,015 discloses isolated and purified forms of FAAH. In one set of embodiments, the FAAH $IC_{50}$ of the subject compounds is defined according to inhibition of the rat enzyme under physiologically relevant conditions. Fatty Amide Hydrolases (FAAHs) (Deutsch, D. G., et al., *Prostaglandins Leukot. Essent. Fatty Acid*, 66, 201-210 (2002)) are enzymes responsible for the degradation of lipid ethanolamides, (Fowler, C. J., et al., *Biochem. Pharmacol.* 62, 517-526 (2001); Patricelli, M. P., et al. *Vitam. Horm.*, 62, 663-674 (2001)) e.g. anandamide (AEA, 1, FIG. 1), (Devane, W. A., et al., *Science* 258, 1946-1949 (1992)) oleoylethanolamide, (Rodriguez de Fonseca, F., et al. *Nature (London)* 414, 209-212 (2001); Fu, J., et al., *Nature (London)* 425, 90-93 (2003)) and palmitoylethanolamide, (Calignano, A., et al. *Nature (London)* 394, 277-281 (1998); Lambert, D. M., et al., *Curr. Med. Chem.* 9, 663-674 (2002)) a biochemical process which, along with selective trasport into cells in the case of AEA, (Di Marzo, V., *Nature (London)* 372, 686-691 (1994); Beltrama, M., et al., *Science* 277, 1094-1097 (1997); Piomelli, D., et al., *Proc. Natl. Acad. Sci. U.S.A.* (2002)) brings about the cessation of the cellular effects of these autacoids. Owing to the various and important physiological roles of fatty acid ethanolamides, classes of small-molecule compounds able to block FAAH or FAAHS but not bind to other endocannabinoid-metabolizing enzymes, e.g. monoglyceride lipase (MGL), (Dinh, T. P., et al., *Proc. Natl. Acad. Sci. U.S.A.* 99, 10819-10824 (2002)) or cannabinoid receptors, would be advantageous both as pharmacological tools and as prototypes for drug development projects (Piomelli, D., et al. *Trends Pharmacol. Sci.* 21, 218-224 (2000); Bisogno, T., et al., *Curr. Pharm. Des.* 8, 533-547 (2002); Yarnell, A., *Chem. Eng. News* 80(49), 32 (2002); Smith, A., *Nat. Rev. Drug Discov.* 2, 92 (2003); Wendeler, M., et al. *Angew. Chem. Int. Ed.* 42, 2938-2941 (2003)).

Compounds of the Invention Generally

Compounds of the invention may contain one or more asymmetric centers and can thus occur as racemates and racemic mixtures, single enantiomers, diastereomeric mixtures and individual diastereomers. The present invention is meant to comprehend all such isomeric forms of the inventive compounds.

Compounds of the invention include the diastereoisomers of pairs of enantiomers. Diastereomers for example, can be obtained by fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of such a compound of the invention may be obtained by stereospecific synthesis using optically pure starting materials of known configuration.

The compounds of the present invention may have unnatural ratios of atomic isotopes at one or more of their atoms. For example, the compounds may be radiolabeled with isotopes, such as tritium or carbon-14. All isotopic variations of the compounds of the present invention, whether radioactive or not, are within the scope of the present invention.

The instant compounds may be isolated in the form of their pharmaceutically acceptable acid addition salts, such as the salts derived from using inorganic and organic acids. Such acids may include hydrochloric, nitric, sulfuric, phosphoric, formic, acetic, trifluoroacetic, propionic, maleic, succinic, malonic and the like. In addition, certain compounds containing an acidic function can be in the form of their inorganic salt in which the counterion can be selected from sodium, potassium, lithium, calcium, magnesium and the like, as well as from organic bases. The term "pharmaceutically acceptable salts" refers to salts prepared from pharmaceutically acceptable non-toxic bases or acids including inorganic bases or acids and organic bases or acids.

The invention also encompasses prodrugs of the present compounds, which on administration undergo chemical conversion by metabolic processes before becoming active pharmacological substances. In general, such prodrugs will be derivatives of the present compounds that are readily convertible in vivo into a functional compound of the invention. Conventional procedures for the selection and preparation of suitable prodrug derivatives are described, for example, in "Design of Prodrugs", ed. H. Bundgaard, Elsevier, 1985. The invention also encompasses active metabolites of the present compounds.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed by the inventive Formulas.

As used herein, the term "heteroatom" is meant to include oxygen (O), nitrogen (N), sulfur (S).

Where substituent groups are specified by their conventional chemical Formulae, written from left to right, they equally encompass the chemically identical substituents which would result from writing the structure from right to left, e.g., —$CH_2O$— is intended to also recite —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, cyclohexylmethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-butadienyl, 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the Formula of the linking group is written. For example, the Formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —OC(O)R', —C(O)R', —CO₂R', —CONR'R", —OC(O)NR'R", —NR"C(O)R', —NR'—C(O)NR'''R''', —NR''C(O)₂R', —NR—C(NR'R"R''')=NR'''', —NR—C(NR'R")=NR''', —S(O)R', —S(O)₂R', —S(O)₂NR'R", —NRSO₂R', —CN and —NO₂ in a number ranging from zero to (2m'+1), where m' is the total number of carbon atoms in such radical. R', R'', R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R'', R''' and R'''' groups when more than one of these groups is present. When R' and R'' are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —OC(O)R', —C(O)R', —CO₂R', —CONR'R", —OC(O)NR'R", —NR"C(O)R', —NR'—C(O)NR'''R''', —NR''C(O)₂R', —NR—C(NR'R"R''')=NR'''', —NR—C(NR'R")=NR''', —S(O)R', —S(O)₂R', —S(O)₂NR'R", —NRSO₂R', —CN and —NO₂, —R', —N₃, —CH(Ph)₂, fluoro(C₁-C₄)alkoxy, and fluoro(C₁-C₄)alkyl, in a number ranging from zero to the total number of open valences on the aromatic ring system; and where R', R'', R''' and R'''' are preferably independently selected from hydrogen, (C₁-C₈)alkyl and heteroalkyl, unsubstituted aryl and heteroaryl, (unsubstituted aryl)-(C₁-C₄)alkyl, and (unsubstituted aryl)oxy-(C₁-C₄)alkyl. When a compound of the invention includes more than one R group, for example, each of the R groups is independently selected as are each R', R'', R''' and R'''' groups when more than one of these groups is present.

Novel Fatty Acid Amide Hydrolase Inhibitory Compounds of the Invention

The invention provides fatty acid amide hydrolase inhibitors of the Formula:

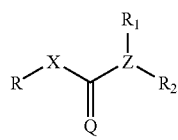

I in which X is CH₂, NH, O, or S; Q is O or S; Z is O or N, with the proviso that if Z is O then one of R₁ or R₂ is absent; and R is an aromatic or alkyl or lipophilic moiety selected from the group consisting of substituted or unsubstituted aryl; substituted or unsubstituted biphenylyl, substituted or unsubstituted naphthyl, and substituted or unsubstituted phenyl; substituted or unsubstituted terphenylyl; substituted or unsubstituted cycloalkyl, substituted or unsubstituted heteroaryl, substituted or unsubstituted alkyl, substituted or unsubstituted heteroalkyl, and

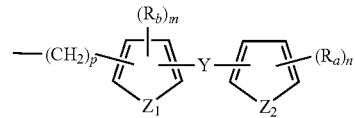

in which p is a number from 0 to 3; m is a number from 0 to 4, and n is a number from 0 to 5, $Z_1$ and $Z_2$ are same or different and are independently a divalent radical selected from the group consisting of —O—, —S—, —N(R₅)—, —C(R₆)=C(R₇)—, —CR₆, —C(R₆)=N— and —N=C(R₆)— wherein R₅ is selected from H, alkyl, heteroalkyl, alkenyl, alkynyl, cycloalkyl, aryl, acyl and aroyl; R₆ and R₇ are independently H or R₆ and R₇ optionally may combine to form a saturated or unsaturated carbocyclic or heterocyclic ring, optionally substituted with one or more $R_a$ and $R_b$ groups; Y is a linker, including but not limited to, a bond, —O—, —S—, —N(R₅)—, C₁-C₄ alkylene, (Z)- or (E)-ethylene, and cycloalkyl with 3 to 6 carbon atoms; $R_a$ and $R_b$ are independently selected from the group consisting of H, alkyl, heteroalkyl, alkenyl, alkynyl, cycloalkyl, aryl, substituted aryl, arylalkyl, substituted arylalkyl, ketoalkyl, hydroxyalkyl, aminoalkyl, —CH₂—NR₃R₄, alkoxy, aryloxy, arylalkyloxy, halo, haloalkyl, cyano, hydroxy, nitro, amino, —NR₃R₄, —SR₅, carboxamido, —CONR₃R₄, —O-carboxamido, —O—CO—NR₃R₄, sulfonamido, and —SO₂NR₃R₄; and R₃ and R₄ are selected from H, alkyl, alkenyl, alkynyl, cycloalkyl, hydroxyalkyl and imino-methylamino and optionally R₃ and R₄ together with the N atom to which they are attached to form a 5-7 membered cyclic ring. When $Z_1$ is —C(R₆)=C(R₇)— or —N=C(R₆)—, and p is 0, the aromatic ring of which $Z_2$ is a member is preferably in the meta or para position with respect to Y. More preferably, the position is meta.

In addition, R₁ and R₂ are independently selected from the group consisting of H, substituted or unsubstituted alkyl, substituted or unsubstituted heteroalkyl, substituted or unsubstituted cycloalkyl, and substituted or unsubstituted cycloheteroalkyl, and substituted or unsubstituted phenyl, and substituted or unsubstituted aryl or heteroaryl, and wherein optionally, when X is N, if taken together with the N atom to which they are attached, R₁ and R₂, form a substituted or unsubstituted N-heterocycle or substituted or unsubstituted heteroaryl with the atom to which they are each attached. In some embodiments, R₁ and R₂ is H or hydrocarbyl selected from alkyl, alkenyl, alkynyl, cycloalkyl in which optionally one or more carbons of these hydrocarbyl groups may be substituted with a heteroatom selected from O, N—R₅, and S—R₅, aryl, acyl and aroyl and in which, optionally, when X is N, if taken together with the N atom to which they are attached, R₁ and R₂, form a substituted or unsubstituted N-heterocycle or substituted or unsubstituted heteroaryl with the atom to which they are each attached.

In some embodiments, in compounds of the above formula, X is O or S; Q is O or S; and R is selected from the group consisting of substituted or unsubstituted aryl, substituted or unsubstituted biphenylyl, substituted or unsubstituted naphthyl, and substituted or unsubstituted phenyl, substituted or unsubstituted terphenylyl, substituted or unsubstituted heteroaryl, and

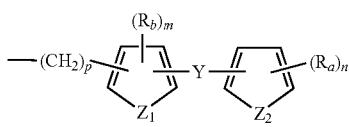

in which p is a number from 0 to 3; m is a number from 0 to 4, and n is a number from 0 to 5, $Z_1$ and $Z_2$ are same or different and are independently a divalent radical selected from the group consisting of —O—, —S—, —N($R_5$)—, —C($R_6$)=C($R_7$)—, and —N=C($R_6$)— wherein $R_5$ is selected from H, alkyl, heteroalkyl, alkenyl, alkynyl, cycloalkyl, aryl, acyl and aroyl; $R_6$ and $R_7$ are independently selected from the group consisting of H, alkyl, heteroalkyl, alkenyl, alkynyl, cycloalkyl, aryl, acyl and aroyl, wherein $R_6$ and $R_7$ optionally may combine to form a saturated or unsaturated carbocyclic or heterocyclic ring, optionally substituted with one or more $R_a$ and $R_b$ groups; and Y is a linking member. Y may be a bond or selected from the group consisting of —O—, —S—, —N($R_5$)—, —S($R_5$)—, —$C_1$-$C_4$ alkylene, (Z)- or (E)-ethylene, and cycloalkyl with 3 to 6 carbon atoms; each $R_a$ and each $R_b$ are independently selected from the group consisting of H, alkyl, heteroalkyl, alkenyl, alkynyl, cycloalkyl, aryl, substituted aryl, arylalkyl, substituted arylalkyl, ketoalkyl, hydroxyalkyl, aminoalkyl, —$CH_2$—$NR_3R_4$, alkoxy, aryloxy, arylalkyloxy, halo, haloalkyl, cyano, hydroxy, nitro, amino, —$NR_3R_4$, —$SR_5$, carboxamido, —$CONR_3R_4$, —O-carboxamido, —O—CO—$NR_3R_4$, sulfonamido, and —$SO_2NR_3R_4$, wherein $R_3$ and $R_4$ are selected from H, alkyl, alkenyl, alkynyl, cycloalkyl, hydroxyalkyl and imino-methylamino and optionally $R_3$ and $R_4$ together with the N atom to which they are attached to form a 5-7 membered cyclic ring; and $R_1$ and $R_2$ are independently selected from the group consisting of H, substituted or unsubstituted alkyl, substituted or unsubstituted heteroalkyl, substituted or unsubstituted cycloalkyl, and substituted or unsubstituted cycloheteroalkyl, and optionally $R_1$ and $R_2$, may be taken together with the N atom to which they are attached to form a substituted or unsubstituted ring.

In another embodiment, in the compound of Formula I, X is O and Q is O. In a further embodiment of such compounds Z is N. In a still further embodiment, p is 0, m is 1 and n is 0, 1, 2, or 3. In still another embodiment, m is 0 and n is 1, 2, or 3.

In still another embodiment of the compound of Formula I, R is selected from the group consisting of substituted or unsubstituted biphenylyl, substituted or unsubstituted naphthyl, substituted or unsubstituted terphenylyl, and substituted or unsubstituted cis-stilbyl ((Z)—C6H5-CH=CHC6H5-). In a further embodiment of such R compound, X is also O and Q is O and Z is N.

In an exemplary embodiment, R is substituted or unsubstituted biphenylyl. In a further embodiment of such biphenyl compounds, X is also O and Q is O and Z is N. In a still further embodiment, at least one of $R_1$ and $R_2$ is H.

In yet another embodiment, in the compound of Formula I, $R_1$ is $C_1$-$C_8$ homoalkyl, $C_1$-$C_8$ heteroalkyl, or $C_1$-$C_8$ cycloalkyl. In a further embodiment, the $C_1$-$C_8$ alkyl is methyl, ethyl, n-propyl, i-propyl, n-butyl, sec-butyl, tert-butyl, pentyl, hexyl, cyclopentyl, cyclohexyl, cycloheptyl, cyclopentenyl, cyclohexenyl, or cycloheptenyl. A particularly preferred $R_1$ group is $R_1$ is cyclohexyl. In a further embodiment of such compounds, X is O; Q is O and Z is N. In an exemplary further embodiment, R is substituted or unsubstituted biphenyl, terphenyl, or stilbyl in which up to 3 atoms of the aromatic ring may be substituted with a heteroatom selected from the group consisting of $NR_5$, O, or S wherein $R_5$ is as defined in any of the above.

In a further embodiment, the compound of Formula I has an $R_1$ group which is a piperidinyl, furyl, furfuryl, furanyl, and morpholinyl and may be substituted or unsubstituted. In a further embodiment of such compounds, X is preferably O; Q is O and Z is N. In a still further embodiment, the R group is substituted or unsubstituted biphenyl, terphenyl, or stilbyl in which up to 3 atoms of the aromatic ring may be substituted with a heteroatom selected from the group consisting of $NR_5$, O, or S wherein $R_5$ is selected from H, alkyl, alkenyl, alkynyl, cycloalkyl, aryl, acyl and aroyl.

In one set of embodiments, the compound of Formula I is of the formula:

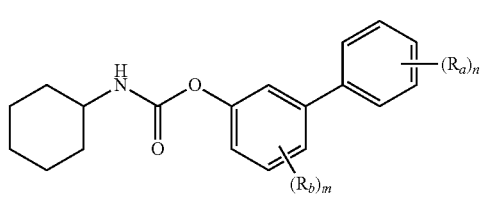

Ia

In the above formula, m is a number from 0 to 4 and n is a number from 0 to 5. In some embodiments, m is 0 or 1 and n is 2 or 3. In the above formula, each $R_a$ and each $R_b$ are independently selected from the group consisting of H, alkyl, alkenyl, alkynyl, cycloalkyl, aryl, substituted aryl, arylalkyl, substituted arylalkyl, ketoalkyl, hydroxyalkyl, aminoalkyl, —$CH_2$—$NR_3R_4$, alkoxy, aryloxy, halo, haloalkyl, cyano, hydroxy, nitro, amino, —$NR_3R_4$, carboxamido, —$ONR_3R_4$, —O-carboxamido, —O—CO—$NR_3R_4$, sulfonamido, —$SO_2NR_3R_4$. $R_3$ and $R_4$ are selected from the group consisting of H, alkyl, heteroalkyl, alkenyl, alkynyl, cycloalkyl, hydroxyalkyl and imino-methylamino or $R_3$ and $R_4$ may combine with the N atom to which they are attached to form a 5-7 membered cyclic ring. In some further embodiments, each $R_a$ and each $R_b$ are independently selected from H, ketoalkyl, hydroxyalkyl, aminoalkyl, —$CH_2$—$NR_3R_4$, alkoxy, halo, haloalkyl, cyano, hydroxy, nitro, amino, —$NR_3R_4$, carboxamido, —$ONR_3R_4$, —O-carboxamido, —O—CO—$NR_3R_4$, sulfonamido, and —$SO_2NR_3R_4$.

Yet another embodiment is represented by a compound of the following formula:

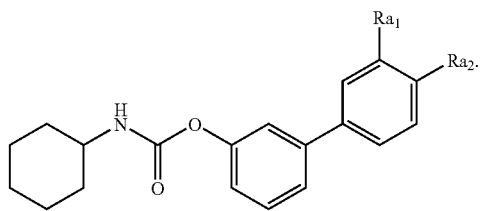

Ib

In the above formula, $Ra_1$ and $Ra_2$ are independently selected from the group consisting of H, alkyl, alkenyl, alkynyl, cycloalkyl, aryl, substituted aryl, arylalkyl, substituted arylalkyl, ketoalkyl, hydroxyalkyl, aminoalkyl, —$CH_2$—$NR_3R_4$, alkoxy, aryloxy, halo, haloalkyl, cyano, hydroxy, nitro, amino, $NR_3R_4$, carboxamido, $CONR_3R_4$, O-carboxamido, O—CO—$NR_3R_4$, sulfonamido, and $SO_2NR_3R_4$; and $R_3$ and $R_4$ are selected from H, alkyl, alkenyl, alkynyl, cycloalkyl, hydroxyalkyl and imino-methylamino. In addition, $R_3$ and $R_4$ may together with the N atom to which they are attached combine to form a 5-7 membered cyclic ring. In a particular set of embodiments, each $R_a$ and each $R_b$ is independently selected from H, ketoalkyl, hydroxyalkyl, aminoalkyl, —$CH_2$—$NR_3R_4$, alkoxy, halo, haloalkyl, cyano, hydroxy, nitro, amino, —$NR_3R_4$, carboxamido, —$ONR_3R_4$, —O-carboxamido, —O—CO—$NR_3R_4$, sulfonamido, and —$SO_2NR_3R_4$. In a further set of such embodiments, at least one of $Ra_1$ and $Ra_2$ is H. In another of such embodiments, $Ra_1$ is selected from the group consisting of —C(O)$NH_2$, —C(O)$CH_3$, or —$(CH_2)_2OH$ and $Ra_2$ is H. In another set of embodiments, $Ra_1$ and $Ra_2$ are each H. In still further embodiments of such compounds $R_1$ is $C_1$-$C_8$ alkyl and $R_2$ is H.

In other embodiments, the compound of Formula I has an $R_1$ of $C_1$-$C_8$ alkyl an X of O, a Q of S and a Z of N. In some such embodiments, R is substituted or unsubstituted phenyl, biphenyl, terphenyl, or stilbyl.

In other embodiments, the compound of Formula I has an X of O, a Q of O and a Z of N, and R is substituted or unsubstituted biaryl or heterobiaryl. In some further embodiments, the heterobiaryl has up to 3 members of the heterobiaryl rings selected from the group consisting of O, N, or S. In still other embodiments, the heterobiaryl is bipyridyl or phenylpyridyl.

In yet another embodiment, the compound of Formula I is n-butyl 4-benzyloxyphenyl carbamate or N-cyclohexyl 3'-carboxamido-biphenyl-3-yl carbamate.

Other embodiments are drawn to those compounds of Formula I which have an $IC_{50}$ for inhibiting the human fatty acid amide hydrolase of less than 1 micromolar. In such embodiments, compounds which have an $IC_{50}$ for inhibiting the human fatty acid amide hydrolase of from 100 to 10 nanomolar, or 10 to 1 nanomolar, or less than 10 nanomolar are exemplary.

In other embodiments, the compounds of Formula I are compounds in which the molecular weight of the R—X— group is greater than the molecular weight of the —$NR_1R_2$ group. In other embodiments, the bulk of the R—X— group is greater than that for the —$NR_1R_2$ group. In further embodiments of such compounds, X is O; Q is O and Z is N. In still further embodiments, R is substituted or unsubstituted aryl, including but not limited to biphenyl, terphenyl, and cis-stilbyl compounds.

In another embodiment of the compound of Formula I, X is O; Q is O; Z is N and

R is substituted or unsubstituted biaryl and substituted or unsubstituted heterobiaryl. In a further embodiment, R is substituted or unsubstituted biaryl or heterobiaryl having up to 3 members of the heterobiaryl rings selected from the group consisting of O, N, or S. In still further embodiments, $R_1$ and $R_2$ are independently selected from the group consisting of H, unsubstituted or substituted homoalkyl, substituted or unsubstituted heteroalkyl, substituted or unsubstituted cycloalkyl, substituted or unsubstituted heterocycloalkyl, and optionally $R_1$ and $R_2$ may be taken together to form a substituted or unsubstituted heterocycle with N; and $Ra_1$ and $Ra_2$ are independently selected from the group consisting of H, alkyl, alkenyl, alkynyl, cycloalkyl, ketoalkyl, hydroxyalkyl, aminoalkyl, —$CH_2$—$NR_3R_4$, alkoxy, aryloxy, halo, haloalkyl, cyano, hydroxy, nitro, amino, —$NR_3R_4$, carboxamido, —$CONR_3R_4$, —O-carboxamido, —O—CO—$NR_3R_4$, sulfonamido, and —$SO_2NR_3R_4$; and $R_3$ and $R_4$ are selected from H, alkyl, heteroalkyl, alkenyl, alkynyl, cycloalkyl, hydroxyalkyl and imino-methylamino or $R_3$ and $R_4$ may combine together with the N to which they are attached to form a 5-7 membered cyclic ring. In a further such embodiment, $R_1$ is $C_1$-$C_8$ homoalkyl, $C_1$-$C_8$ heteroalkyl, or $C_1$-$C_8$ cycloalkyl.

In a still further embodiment, $R_2$ is H. In a still further embodiment, $R_1$ is cyclohexyl and $R_2$ is H.

The invention also provides fatty acid amide hydrolase inhibitors of the Formula:

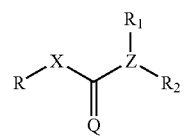

Ic in which X is NH, O, or S; Q is O or S; Z is O or N; and R is an aromatic or alkyl or lipophilic moiety selected from the group consisting of substituted or unsubstituted aryl; substituted or unsubstituted biphenylyl, substituted or unsubstituted naphthyl, and substituted or unsubstituted phenyl; substituted or unsubstituted terphenylyl; substituted or unsubstituted cycloalkyl, heteroaryl, or alkyl; and wherein $R_1$ and $R_2$ are independently selected from the group consisting of H, substituted or unsubstituted alkyl, substituted or unsubstituted heteroalkyl, and substituted or unsubstituted phenyl; with the provision that if Z is O, one of $R_1$ or $R_2$ is absent, and further with the proviso that if Z is N, $R_1$ and $R_2$ may be optionally taken together to form a substituted or unsubstituted N-heterocycle or substituted or unsubstituted heteroaryl with the N atom to which they are each attached. In some embodiments, $R_1$ and $R_2$ is H or hydrocarbyl selected from alkyl, alkenyl, alkynyl, cycloalkyl in which optionally one or more carbons of these hydrocarbyl groups may be substituted with a heteroatom selected from O, N—$R_5$, and S—$R_5$, aryl, acyl and aroyl; $R_6$ and $R_7$ In one embodiment, the FAAH inhibitory compound of Formula Ia has an $IC_{50}$ of less than 10 μM or 1 μM. In another, embodiment the compound of Formula I is an FAAH inhibitor with an $IC_{50}$ of less than 0.01 μM. In another embodiment, the compound of Formula I is an inhibitor of FAAH with an $IC_{50}$ of from about 1 μM to 0.01 μM, or from about 0.01 to 0.001 μM.

In one embodiment of a compound of Formula Ia, X is O, Q is O; and Z is N. In another embodiment, X is O; Q is O; and Z is N; $R_1$ is H and $R_2$ is cyclohexyl. In another embodiment, X is O, Q is O; Z is N and R is substituted or unsubstituted biphenylyl. In a further embodiment, X is O, Q is O; Z is N; $R_1$ is H, $R_2$ is cyclohexyl and R is substituted or unsubstituted biphenylyl or substituted or unsubstituted phenyl.

In another embodiment of a compound of Formula Ia, X is O; Q is O; and Z is N; $R_1$ is H and $R_2$ is cyclohexyl. In another embodiment, R is substituted or unsubstituted biphenylyl. In another embodiment, $R_1$ is H and $R_2$ is cyclohexyl and R is substituted or unsubstituted biphenylyl or substituted or unsubstituted phenyl.

In one embodiment the compound of Formula I is of the Formula

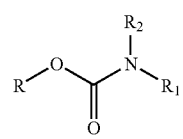

II in which R is an aromatic or alkyl or lipophilic moiety selected from the group consisting of substituted or unsubstituted aryl; substituted or unsubstituted biphenylyl, substituted or unsubstituted naphthyl, and substituted or unsubstituted phenyl; substituted or unsubstituted terphenylyl; substituted or unsubstituted cycloalkyl, heteroaryl, or alkyl; and wherein $R_1$ and $R_2$ are independently selected from the group consisting of H, substituted or unsubstituted alkyl, substituted or unsubstituted heteroalkyl, and substituted or unsubstituted phenyl, substituted or unsubstituted aryl, substituted or unsubstituted heteroaryl, and optionally wherein if $R_1$ and $R_2$ are taken together, form a substituted or unsubstituted N-heterocycle or substituted or unsubstituted heteroaryl with the atom to which they are each attached. In some embodiments, the compound of Formula I or II has an R group with a greater molecular weight or mass than the —$NR_1R_2$ portion of the compound.

In another embodiment, the FAAH inhibitory compound of Formula II has an $IC_{50}$ Of less than 10 μM or 1 μM. In another, embodiment the compound of Formula II is an FAAH inhibitor with an $IC_{50}$ of less than 0.01 μM. In another embodiment, the compound of Formula II is an inhibitor of FAAH with an $IC_{50}$ of from about 1 μM to 0.01 μM, or from about 0.01 to 0.001 μM.

In one embodiment, R is naphthyl in the compound of Formula I, Ia-c, II, or Ia-b, and III.

In another embodiment, $R_1$ is H and $R_2$ is cyclohexyl in a compound of Formula I, Ia-c, II, or IIa-b. In another embodiment, $R_1$ is H and $R_2$ is alkyl in the compound of Formula I, Ia-c, II, or IIa-b.

In another embodiment, $R_1$ is H and $R_2$ is alkyl and R is alkyl in the compound of Formula I, Ia-c, II, or IIa-b.

In another embodiment, $R_1$ is H and $R_2$ is cyclohexyl and R is substituted or unsubstituted aryl in the compound of Formula Ic or Formula II. In a further embodiment, in the compound of Formula Ic or Formula II, R is substituted or unsubstituted biphenylyl. In a still further embodiment, the biphenyl is substituted with halogen (e.g., F) or alkyl (e.g., methyl) or amino or amido or trifluoromethyl.

Exemplary compounds according to Formula I, Ia-c, II, or IIa-b include, but are not limited to, the following compounds from Table 3: 2-naphthyl N-cyclohexylcarbamate; 4-(benzyloxy)phenyl N-butyl carbamate; 6-bromo-2-naphthylyl N-butylcarbamate; 4-biphenylyl N-cyclohexylcarbamate; hexyl N-cyclohexyl carbamate; p-tolyl-N-cyclohexylcarbamate; O-butyl 4-(4'methoxyphenoxycarbonyl)-phenyl carbonate; and 4-fluorophenyl N-butyl carbamate.

In another embodiment, the compound of Formula I is UCM532 or UCM597.

In another embodiment, the inventive FAAH inhibitor is a compound of Formula II in which $R_1$ is H: $R_2$ is $C_1$-$C_{10}$ alkyl; and R is substituted aryl. In a further embodiment, $R_2$ is a tert-butyl, sec-butyl, or n-butyl moiety. In another embodiment of the compounds according to the above Formula II, $R_2$ is cyclohexyl.

In another embodiment, the inventive FAAH inhibitor is a compound of Formula I, II, or IIa in which $R_1$ is H; $R_2$ is $C_1$-$C_{10}$ alkyl; and R is one of the following:

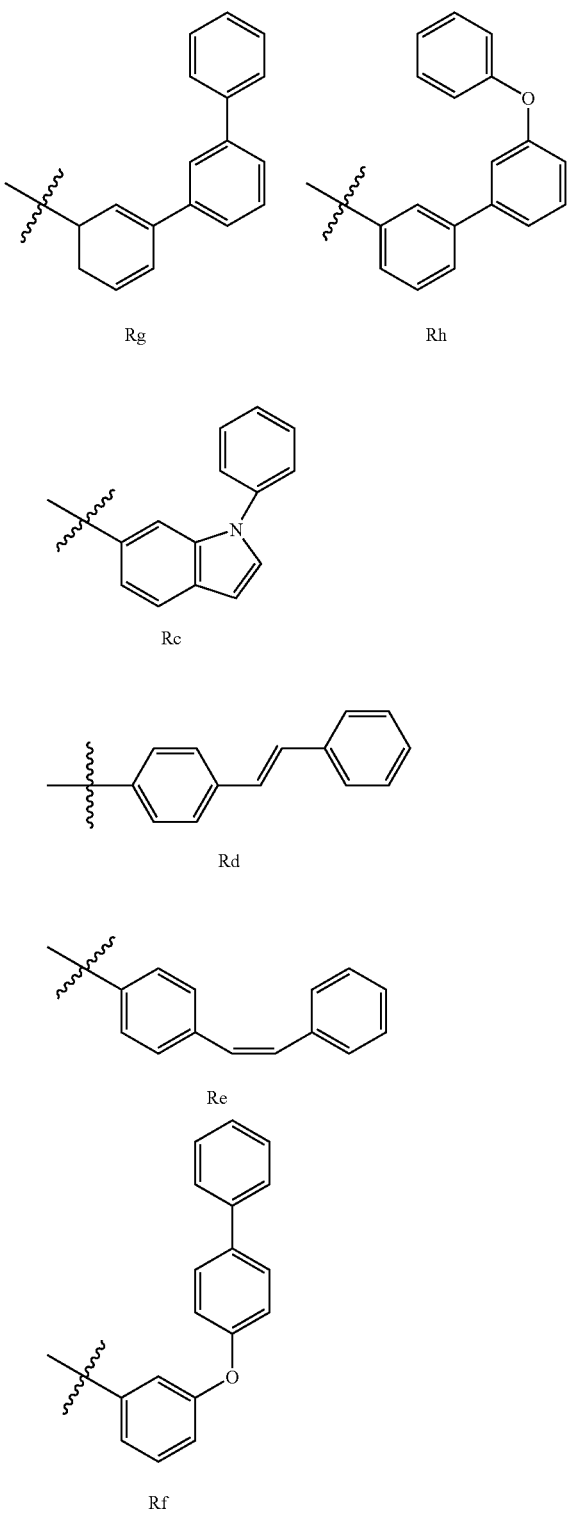

In other embodiments, wherein R is one of Rf, Rg, Rc, Rd, Re, or Rh, $R_2$ is a tert-butyl, sec-butyl, n-butyl moiety, or cyclohexyl. In other embodiments, wherein R is one of Rf, Rg, Rc, Rd, Re, or Rh, each of the benzene rings are further independently and optionally substituted with one, two, three, or four substituents, other than a sole H atom, as defined above for aryl or heteroaryl groups.

In another embodiment, the compound is of Formula IIa:

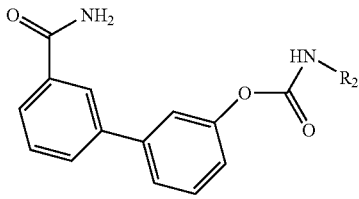

IIa in which $R_2$ is $C_1$-$C_{10}$ alkyl. In a further embodiment, $R_2$ is a cyclohexyl or tert-butyl, sec-butyl, or n-butyl moiety. In another embodiment of the compounds according to the above Formula IIA, $R_2$ is cyclohexyl.

In other embodiments, the inventive compounds are compounds of Formula IIa which are additionally further independently and optionally substituted on each of the benzene rings with one, two, three, or four other substituents, other than a sole H atom, as defined above for aryl or heteroaryl groups In another embodiment, compound or the FAAH inhibitor is a compound of Formula IIb:

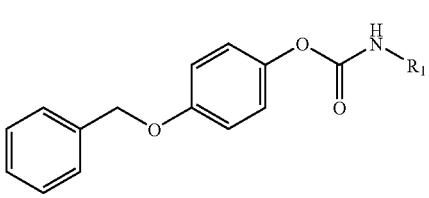

IIb in which $R_1$ is alkyl. In a further embodiment, $R_1$ is lower $C_1$-$C_6$ alkyl. In a still further embodiment, $R_1$ is a t-butyl, s-butyl, n-butyl, hexyl, or cyclohexyl moiety. In other embodiments, the inventive compounds are compounds of Formula IIb which are additionally further independently and optionally substituted on each of the benzene rings with one, two, three, or four additional substituents, other than a sole H atom, as defined above for aryl or heteroaryl groups.

In some embodiments, a compound according to the invention is any compound of Table I through Table VI which has a FAAH $IC_{50}$ of less than 1 micromolar.

In the embodiments, the compounds (e.g., the compounds of Formulae I, Ia-Ic, II, IIa-IIb, III), include their pharmaceutically acceptable salts and biologically active isomers and conformers.

In another aspect, the invention provides FAAH inhibitors and compounds or the following general formula:

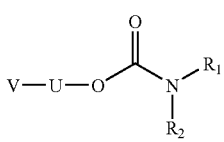

III in Formula III, $R_1$ and $R_2$ are independently selected from the group consisting of H, unsubstituted or substituted homoalkyl, substituted or unsubstituted heteroalkyl, substituted or unsubstituted cycloalkyl, substituted or unsubstituted heterocycloalkyl, and optionally $R_1$ and $R_2$, may be taken together to form a substituted or unsubstituted heterocycle with N; U is a hydrophobic spacer, wherein the spacer comprises substituted or unsubstituted aryl; and V is a hydrophilic moiety having at least one functional group capable of forming a hydrogen bond. In addition, the hydrophobic spacer is at least 9 angstroms in length; and the hydrophilic moiety is attached to the spacer at a point from 8 to 12 angstroms distant from a point at which the hydrophobic spacer is covalently attached to the rest of the inhibitor.

In a further embodiment, the inhibitor or compound of Formula III has a hydrophobic spacer comprising a first and a second aromatic ring, wherein the first and second aromatic rings are covalently attached by a linker selected from the group consisting of a bond, a single heteroatom, and substituted or unsubstituted $C_1$ to $C_4$ alkylene.

In another embodiment, V is selected from the group consisting of ketoalkyl, hydroxyalkyl, aminoalkyl, —$CH_2$—$NR_3R_4$, alkoxy, aryloxy, halo, haloalkyl, cyano, hydroxy, nitro, amino, —$NR_3R_4$, carboxamido, —$CONR_3R_4$, —O-carboxamido, —O—CO—$NR_3R_4$, sulfonamido, and —$SO_2NR_3R_4$; wherein $R_3$ and $R_4$ are selected from H, alkyl, heteroalkyl, alkenyl, alkynyl, cycloalkyl, hydroxyalkyl and imino-methylamino or $R_3$ and $R_4$ may combine with the N atom to which they are attached to form a 5-7 membered cyclic ring.

In another embodiment, U and V are each set forth as described above and the hydrophilic moiety is attached to the spacer at a point about 9 to 11 angstroms from a point at which the spacer is covalently attached to the rest of the inhibitor. In a further embodiment, the hydrophilic moiety is attached to the spacer at a point about 10 angstroms from a point at which the spacer is covalently attached to the rest of the inhibitor.

In another embodiment, U and V taken together have a greater molecular weight or bulk than the remainder of the molecule or than the —$NR_1R_2$ moiety.

In some embodiments, in Formula I, Ia-c, II, IIa-b, or III, $R_1$ and $R_2$ are independently selected from H or hydrocarbyl selected from alkyl, alkenyl, alkynyl, and cycloalkyl in which optionally one or more carbons of these hydrocarbyl groups may be substituted with a heteroatom selected from O, N—$R_5$, and S—$R_5$, and in which, optionally, when X is N, if taken together with the N atom to which they are attached, $R_1$ and $R_2$ form a substituted or unsubstituted N-heterocycle or substituted or unsubstituted heteroaryl. In these embodiments, $R_5$ is a H or a hydrocarbyl selected from alkyl, alkenyl, alkynyl, cycloalkyl in which optionally one or more carbons of these hydrocarbyl groups may be substituted with a heteroatom selected from O, NH, and SH.

In some embodiments, in Formula I, Ia-c, II, IIa-b, or III, $R_1$ and $R_2$ are independently selected from H or hydrocarbyl selected from alkyl, alkenyl, alkynyl, and cycloalkyl in which optionally one or more carbons of these hydrocarbyl groups may be substituted with a heteroatom selected from O, N—$R_5$, and S—$R_5$, and in which, optionally, when X is N, if taken together with the N atom to which they are attached, $R_1$ and $R_2$ form a substituted or unsubstituted N-heterocycle or substituted or unsubstituted heteroaryl. In these embodiments, $R_5$ is a H or a hydrocarbyl selected from alkyl, alkenyl, alkynyl, cycloalkyl in which optionally one or more carbons of these hydrocarbyl groups may be substituted with a heteroatom selected from O, NH, and SH. In still further embodiments in which p is a number from 0 to 3; m is a number from 0 to 4, and n is a number from 0 to 5, $Z_1$ and $Z_2$ are same or different and are independently a divalent radical selected from the group consisting of —O—, —S—, —N($R_5$)—, —C($R_6$)=C($R_7$)—, —$CR_6$, —N=C($R_6$)— and —C($R_6$)=N—, and $R_6$ and $R_7$ are independently selected from H or hydrocarbyl in which the hydrocarbyl is alkyl, alkenyl, alkynyl, cycloalkyl and optionally one or more carbons of these hydrocarbyl groups may be substituted with a heteroatom selected from O, N—$R_5$, and S—$R_5$, aryl, acyl and aroyl. In preferred sets of these embodiments, the hydrocarbyl groups are each independently a $C_1$ to $C_{10}$ hydrocarbyl group which may be optionally substituted with O, N—$R_5$, and S—$R_5$ in which $R_5$ is also a $C_1$ to $C_{10}$ hydrocarbyl. In a more preferred set of embodiments, the $R_6$ and $R_6$ are each independently a $C_1$ to $C_6$ hydrocarbyl group which may be optionally substituted with O, N—$R_5$, and S—$R_5$ in which the $R_5$ hydrocarbyl groups are $C_1$ to $C_6$.

In some preferred embodiments, in Formula I, Ia-c, II, IIa-b, or III, $R_1$ is selected from the group consisting of piperidinyl, furyl, furfuryl, furanyl, morpholinyl, is 2-, 3-, 4-piperidinyl, 2- and 3-morpholinyl, 2- and 3-furyl, furfuryl, 2- and 3-pyrryl or 2- or 3-thienyl.

In some preferred embodiments, in Formula I, Ia-c, II, IIa-b, or III, $R_1$ is $C_1$-$C_8$ hydrocarbyl selected from alkyl and cycloalkyl and optionally one or more carbons of these hydrocarbyl groups may be substituted with a heteroatom selected from O, N—$R_5$, and S—$R_5$. In still further such embodiments, $R_2$ is H. In still further preferred embodiments, R is substituted or unsubstituted biphenylyl.

In some embodiments, in Formula I, Ia-c, II, IIa-b, or III, $R_a$ and $R_b$ are independently selected from the H or a hydrocarbyl group consisting of alkyl, alkenyl, alkynyl, cycloalkyl, wherein optionally one or more carbons of these hydrocarbyl groups may be substituted with a heteroatom selected from O, N—$R_5$, and S—$R_5$, aryl; substituted aryl; aralkyl; substituted aralkyl; ketoalkyl; hydroxyalkyl; aminoalkyl; —$CH_2$—$NR_3R_4$, alkoxy, aryloxy, aralkyloxy, halo, haloalkyl, cyano, hydroxy, nitro, amino, —$NR_3R_4$, $SR_5$, carboxamido, —$CONR_3R_4$, O-carboxamido, —O—CO—$NR_3R_4$, sulfonamido, and —$SO_2NR_3R_4$, wherein $R_3$ and $R_4$ are selected from H or a hydrocarbyl group selected from alkyl, alkenyl, alkynyl, cycloalkyl, hydroxyhomoalkyl and imino-methylamino and optionally $R_3$ and $R_4$ may combine to form a 5-7 membered cyclic ring with the N to which they are attached. In these embodiments, $R_5$ is a H or a hydrocarbyl selected from alkyl, alkenyl, alkynyl, cycloalkyl in which optionally one or more carbons of these hydrocarbyl groups may be substituted with a heteroatom selected from O, NH, and SH. In preferred sets of these embodiments, the hydrocarbyl groups are each independently a $C_1$ to $C_{10}$ hydrocarbyl group which may be optionally substituted with O, N—$R_5$, and S—$R_5$ in which $R_5$ is also a $C_1$ to $C_{10}$ hydrocarbyl. In a more preferred set the $R_a$ and $R_b$ are each independently a $C_1$ to $C_6$ hydrocarbyl group which may be optionally substituted with O, N—$R_5$, and S—$R_5$ in which the $R_5$ hydrocarbyl groups are $C_1$ to $C_6$.

In some embodiments, in Formula I, Ia-c, II, IIa-b, or III, $R_1$ and $R_2$ are independently selected from H or hydrocarbyl selected from alkyl, alkenyl, alkynyl, and cycloalkyl in which optionally one or more carbons of these hydrocarbyl groups may be substituted with a heteroatom selected from O, N—$R_5$, and S—$R_5$, and in which, optionally, when X is N, if taken together with the N atom to which they are attached, $R_1$ and $R_2$ form a substituted or unsubstituted N-heterocycle or substituted or unsubstituted heteroaryl. In these embodiments, $R_5$ is a H or hydrocarbyl selected from alkyl, alkenyl, alkynyl, cycloalkyl in which optionally one or more carbons of these hydrocarbyl groups may be substituted with a heteroatom selected from O, NH, and SH. In still further embodiments, in which p is a number from 0 to 3; m is a number from 0 to 4, and n is a number from 0 to 5; $Z_1$ and $Z_2$ are same or different and are independently a divalent radical selected from the group consisting of —O—, —S—, —N($R_5$)—, —C($R_6$)=C($R_7$)—, —$CR_6$, —C($R_6$)=N— and —N=C($R_6$)— and $R_6$ and $R_7$ are independently selected from H or hydrocarbyl in which the hydrocarbyl is alkyl, alkenyl, alkynyl, cycloalkyl and optionally one or more carbons of these hydrocarbyl groups may be substituted with a heteroatom selected from O, N—$R_5$, and S—$R_5$, aryl, acyl and aroyl. In preferred sets of these embodiments, the hydrocarbyl groups are each independently a $C_1$ to $C_{10}$ hydrocarbyl group which may be optionally substituted with O, N—$R_5$, and S—$R_5$ in which $R_5$ is also a $C_1$ to $C_{10}$ hydrocarbyl. In a more preferred set of such compounds, the $R_6$ and $R_6$ are each independently a $C_1$ to $C_6$ hydrocarbyl group which may be optionally substituted with O, N—$R_5$, and S—$R_5$ in which the $R_5$ hydrocarbyl groups are $C_1$ to $C_6$. In still further embodiments, $R_a$ and $R_b$ are independently selected from the H or a hydrocarbyl group consisting of alkyl, alkenyl, alkynyl, cycloalkyl, wherein optionally one or more carbons of these hydrocarbyl groups may be substituted with a heteroatom selected from O, N—$R_5$, and S—$R_5$, aryl; substituted aryl; aralkyl; substituted aralkyl; ketoalkyl; hydroxyalkyl; aminoalkyl; —$CH_2$—$NR_3R_4$, alkoxy, aryloxy, aralkyloxy, halo, haloalkyl, cyano, hydroxy, nitro, amino, —$NR_3R_4$, $SR_5$, carboxamido, —$CONR_3R_4$, O-carboxamido, —O—CO—$NR_3R_4$, sulfonamido, and —$SO_2NR_3R_4$, wherein $R_3$ and $R_4$ are selected from H or a hydrocarbyl group selected from alkyl, alkenyl, alkynyl, cycloalkyl, hydroxyhomoalkyl and imino-methylamino and optionally $R_3$ and $R_4$ may combine to form a 5-7 membered cyclic ring with the N to which they are attached. In these embodiments, $R_5$ is a H or a hydrocarbyl selected from alkyl, alkenyl, alkynyl, cycloalkyl in which optionally one or more carbons of these hydrocarbyl groups may be substituted with a heteroatom selected from O, NH, and SH. In preferred sets of these embodiments, the hydrocarbyl groups are each independently a $C_1$ to $C_{10}$ hydrocarbyl group which may be optionally substituted with O, N—$R_5$, and S—$R_5$ in which $R_5$ is also a $C_1$ to $C_{10}$ hydrocarbyl. In a more preferred set the $R_a$ and $R_b$ are each independently a $C_1$ to $C_6$ hydrocarbyl group which may be optionally substituted with O, N—$R_5$, and S—$R_5$ in which the $R_5$ hydrocarbyl groups are $C_1$ to $C_6$.

Synthesis of Inhibitors of Formula I or Formula II

The compounds of the present invention can be made with commercially available starting materials using straightforward chemistry. Carbamates are well known in the art. The following procedures are exemplary synthetic routes, which are intended to illustrate, but not to limit the present invention. One of ordinary skill in the art will recognize other variations, modifications, and alternatives.

In one example, n-butylcarbamic acid 4-benzyloxyphenyl ester (UCM532) (4) and 4-fluorophenylcarbamic acid 4-benzyloxyphenyl ester (8) were obtained by treatment of 4-benzyloxyphenol with n-butylisocyanate, and 4-fluorophenylisocyanate, respectively, with a catalytic amount of triethylamine in refluxing toluene. The resulting products were obtained in good yields.

Similarly, cyclohexylcarbamic acid biphenyl-3-yl ester (5), cyclohexylcarbamic acid 5-phenylpentyl ester (7), and cyclohexylcarbamic acid 3'-carbamoylbiphenyl-3-yl ester (UCM597) (6) were synthesized by reacting cyclohexylisocyanate with 3-phenylphenol, 5-phenylpentan-1-ol, and 3'-hydroxybiphenyl-3-carboxylic acid amide, respectively. Again, the resulting products were obtained in good yield.

The latter reactant was prepared as follows: 3-bromobenzoic acid amide, obtained by reaction of 3-bromobenzonitrile and sodium perborate, was coupled with methoxyphenylboronic acid to give 3'-methoxybiphenyl-3-carboxylic acid amide, which was hydrolized with $BBr_3$ to generate the desired 3'-hydroxybiphenyl-3-carboxylic acid amide. Detailed synthetic procedures and physicochemical data will be reported elsewhere.

Other methods suitable for making the subject compounds are disclosed in Tarzia et al. *J. Med. Chem.* 46:2352-2360 (2003) and Kathuria et al. *Nature Medicine* 9(1): 76 (2003) which are incorporated herein by reference.

Other FAAH Inhibitors for Use in the Treatment of Anxiety

Trifluoroketone inhibitors such as the compound of Formula IV are also contemplated for use in inhibiting FAAH to raise endogenous levels of anandamide or treat the subject conditions and disorders.

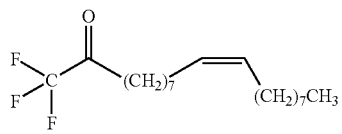

IV

Such compounds are taught in U.S. Pat. No. 6,096,784 herein incorporated by reference.

Other compounds for use according to the invention include octylsulfonyl and octylphosphonyl compounds. See Quistand et al. in Toxicology and Applied Pharmacology 179: 57-63 (2002). See also Quistand et al. in Toxicology and Applied Pharmacology 173: 48-55 (2001).

Other compounds for use according to the invention include the alpha-keto-oxazolpyridines which are reversible and extremely potent inhibitors of FAAH. See Boger et al., PNAS USA 97:5044-49 (2000). Exemplary compounds include compounds of the Formula:

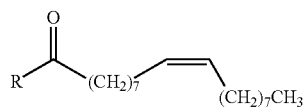

IV wherein R is an alpha-keto oxazolopyridinyl moiety such as

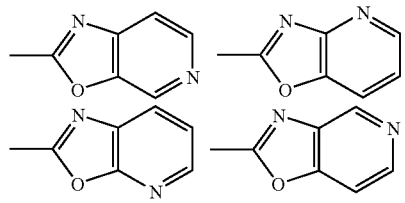

Boger et al. teach other exemplary compounds of the invention including substituted alpha-keto-heterocycle analogs of fatty acid amides. In particular, wherein R is an alpha-keto oxazolopyridinyl moiety and the fatty acid moiety is a homolog of oleic acid or arachidonic acid.

Other FAAH inhibitors for use according to the invention include fatty acid sulfonyl fluorides such as compound AM374 which irreversibly binds FAAH. See Deutsch et al., *Biochem. Biophys Res Commun.* 231:217-221 (1997).

Methods of Screening Compounds for FAAH Inhibitory Activity

Methods for screening compounds for FAAH inhibitory activity in vitro are well known to one of ordinary skill in the art. Such methods are taught in Quistand et al. in *Toxicology and Applied Pharmacology* 179: 57-63 (2002); Quistand et al. in *Toxicology and Applied Pharmacology* 173, 48-55 (2001); Boger et al., *Proc. Natl. Acad. Sci. U.S.A.* 97, 5044-49 (2000).

Methods for screening compounds for FAAH inhibitory activity in vivo and increased endogenous cannabinoid levels or activity are known to one of ordinary skill in the art. Such methods include measurement of fatty acid ethanolamides in tissue and are taught in Quistand et al. in *Toxicology and Applied Pharmacology* 179, 57-63 (2002); Quistand et al. in *Toxicology and Applied Pharmacology* 173, 48-55 (2001); Boger et al., *Proc. Natl. Acad. Sci. U.S.A.* 97:5044-49 (2000). See U.S. Pat. No. 6,096,784. See also PCT Publication WO 98/24396. See Cravatt et al. *Proc. Natl. Acad. Sci. U.S.A.* 98, 9371-9376 (2001).

Methods for Assaying ACHE and NTE Inhibitory Activity

One of ordinary skill in the art would know how to screen a substance for an inhibitory effect on ACHE or NTE. See for instance Quistand et al. in *Toxicology and Applied Pharmacology* 179, 57-63 (2002); and Quistand et al. in *Toxicology and Applied Pharmacology* 173, 48-55 (2001).

Cannabinoid CB1 Receptor Activity

A variety of means may be used to screen cannabinoid CB1 receptor binding activity in order to identify the compounds according to the invention. A variety of such methods are taught in U.S. Pat. No. 5,747,524 and U.S. Pat. No. 6,017,919.

CB1 receptor binding assays are well known to one of ordinary skill in the art. For instance, see, U.S. Patent Application No. US 2001/0053788 published on Dec. 20, 2001, U.S. Pat. No. 5,747,524, and U.S. Pat. No. 5,596,106 and (see: Felder, C. C., et al., *Proc. Natl. Acad. Sci.*, 90, 7656-7660 (1993) each of which is incorporated herein by reference. The affinity of an agent for cannabinoid CB1 receptors can be determined using membrane preparations of Chinese hamster ovary (CHO) cells in which the human cannabis CB1 receptor is stably transfected in conjunction with [$^3$H]CP-55, 940 as radioligand. After incubation of a freshly prepared cell membrane preparation with the [$^3$H]-ligand, with or without addition of compounds of the invention, separation of bound and free ligand can be performed by filtration over glass fiber filters. Radioactivity on the filter was measured by liquid scintillation counting.

The cannabinoid CB1 activity of a candidate compound for use according to the invention can also be determined by functional studies using CHO cells in which human cannabinoid CB1 receptors are stably expressed. Adenylyl cyclase can be stimulated using forskolin and measured by quantifying the amount of accumulated cyclic AMP. Concomitant activation of CB1 receptors by CB1 receptor agonists (e.g., CP-55,940 or (R)-WIN-55, 212-2) can attenuate the forskolin-induced accumulation of cAMP in a concentration-dependent manner. This CB1 receptor-mediated response can be antagonized by CB1 receptor antagonists. See, U.S. Patent Application No. US 2001/0053788 published on Dec. 20, 2001.

Samples rich in cannabinoid CB1 receptors and CB2 receptors, rat cerebellar membrane fraction and spleen cells can be respectively used (male SD rats, 7-9 weeks old). A sample (cerebellar membrane fraction: 50 μg/ml or spleen cells: 1(×10$^7$ cells/ml), labeled ligand ([$^3$H]Win55212-2, 2 nM) and unlabeled Win55212-2 or a test compound can be plated in round bottom 24 well plates, and incubated at 30° C. for 90 min in the case of cerebellar membrane fraction, and at 4° C. for 360 min in the case of spleen cells. As the assay buffer, 50 mM Tris solution containing 0.2% BSA can be used for cerebellar membrane fraction, and 50 mM Tris-HBSS containing 0.2% BSA can be used for spleen cells. After incubation, the samples are filtrated through a filter (Packard, Unifilter 24 GF/B) and dried. A scintillation solution (Packard, Microsint-20) can be added, and the radioactivity of the samples determined (Packard, Top count A9912V). The non-specific binding can be determined by adding an excess Win55212-2 (1 µM), and calculating specific binding by subtracting non-specific binding from the total binding obtained by adding the labeled ligand alone. The test compounds can be dissolved in DMSO to the final concentration of DMSO of 0.1%. $IC_{50}$ can be determined from the proportion of the specifically-bound test compounds, and the $K_i$ value of the test compounds can be calculated from $IC_{50}$ and $K_d$ value of [$^3$H]WIN55212-2. See U.S. Pat. No. 6,017,919.

In one embodiment, the $IC_{50}$ for cannabinoid receptor binding is determined according to the method of Devane et al. *Science* 258: 1946-1949 (1992) and Devane et al. *J. Med. Chem.* 35:2065 (1992). In this method, the ability of a compound to competitively inhibit the binding of an radiolabeled probe (e.g., $^3$H—HU-2430) is determined.

In other embodiments, the $IC_{50}$ of an inventive compound for the CB1 receptor is determined according to any one of the above ligand binding assay methods. In another embodiment, the $IC_{50}$ is according to any assay method which studies binding at physiological pH or physiologically relevant conditions. In another embodiment, the $IC_{50}$ is determined according to any assay method which studies binding at physiological pH and ionic strength.

Cannabinoid CB2 Receptor Binding Assay

Methods of studying CB2 receptor binding are well known to one of ordinary skill in the art. For instance, binding to the human cannabinoid CB2 receptor can be assessed using the procedure of Showalter, et al., *J. Pharmacol Exp Ther.* 278(3), 989-99 (1996), with minor modifications as taught for instance in U.S. Patent Application No. 20020026050 published Feb. 28, 2002. Each of which is incorporated herein by reference.

In other embodiments, the $IC_{50}$ of an inventive compound for the CB2 receptor is determined according to any one of the above CB2 receptor ligand binding assay methods. In another embodiment, the $IC_{50}$ is according to any assay method which studies binding at physiological pH or physiologically relevant conditions. In another embodiment, the $IC_{50}$ is determined according to any assay method which studies binding at physiological pH and ionic strength.

Combinatorial Chemical Libraries

Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al., *J. Med. Chem.* 37(9), 1233 (1994)).

Preparation and screening of combinatorial chemical libraries are well known to those of skill in the art. Such combinatorial chemical libraries include, but are not limited to diversomers such as hydantoins, benzodiazepines and dipeptides (Hobbs et al., *Proc. Natl. Acad. Sci. U.S.A.* 90, 6909 (1993)), analogous organic syntheses of small compound libraries (Chen et al., *J. Amer. Chem. Soc.* 116: 2661 (1994)), oligocarbamates (Cho, et al., *Science* 261, 1303 (1993)), and/or peptidyl phosphonates (Campbell et al., *J. Org. Chem.* 59: 658 (1994)), and small organic molecule libraries (see, e.g., benzodiazepines (Baum *C&EN.* January 18, 33 (1993)), thiazolidinones and metathiazanones (U.S. Pat. No. 5,549,974), pyrrolidines (U.S. Pat. Nos. 5,525,735 and 5,519,134), benzodiazepines (U.S. Pat. No. 5,288,514), and the like.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, HewlettPackard, Palo Alto, Calif.) which mimic the manual synthetic operations performed by a chemist. Any of the above devices are suitable for use with the present invention. The nature and implementation of modifications to these devices so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Biosciences, Columbia, Md., etc.).

High Throughput FAAH Inhibition Assays of Chemical Libraries of Compounds According to Formula I or II The assays for compounds described herein are amenable to high throughput screening. Preferred assays thus detect binding of the inhibitor to FAAH or the release of a reaction product (e.g., fatty acid amide or ethanolamine) produced by the hydrolysis of a substrate such as oleoylethanolamide or ananadamide. The substrate may be labeled to facilitate detection of the released reaction products. High throughput assays for the presence, absence, or quantification of particular reaction products are well known to those of skill in the art. Thus, for example, U.S. Pat. No. 5,559,410 discloses high throughput screening methods for proteins, and U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

Screening for Anxiolytic Activity

One of ordinary skill in the art would appreciate that there are a number of animal models available for assessing the antianxiety effects of a compound. Two pharmacologically validated animal models of anxiety are the elevated zero maze test, and the isolation-induced ultrasonic emission test. The zero maze consists of an elevated annular platform with two open and two closed quadrants and is based on the conflict between an animal's instinct to explore its environment and its fear of open spaces, where it may be attacked by predators (Bickerdike, M. J. et al., *Eur. J. Pharmacol.*, 271, 403-411 (1994); Shepherd, J. K. et al., *Psychopharmacology*, 116, 56-64 (1994)). Clinically used anxiolytic drugs, such as the benzodiazepines, increase the proportion of time spent in, and the number of entries made into, the open compartments.

A second test for an antianxiety compound is the ultrasonic vocalization emission model, which measures the number of stress-induced vocalizations emitted by rat pups removed from their nest (Insel, T. R. et al., *Pharmacol. Biochem. Behav.*, 24, 1263-1267 (1986); Miczek, K. A. et al., *Psychopharmacology*, 121, 38-56 (1995); Winslow, J. T. et al., *Biol. Psychiatry*, 15, 745-757 (1991).

A large number of animal models have been developed in the attempt to predict the anxiolytic activity of novel compounds in man. Many of these paradigms evaluate animal behavior in a so-called "conflict" situation, i.e. a behavioral response is simultaneously under the influence of two opposing motivational states such as approach and avoidance tendencies. Probably the best known model is the conditioned punishment conflict paradigm in which animals are trained to voluntarily exhibit a certain response (e.g. pressing a lever) in order to receive a reward (e.g. food for a hungry animal). Once the animals exhibit a constant rate of lever-press responding, then short periods are introduced (usually signaled by visual or acoustic signals) during which lever pressing is simultaneously rewarded by food and punished by mild electrical foot shock. Animals exhibit a markedly reduced response rate during these conflict periods, which are also characterized by various overt signs of emotionality. The characteristic effect of benzodiazepine receptor agonists, for example the anxiolytic diazepam, is the disinhibition of punished behavior (resulting in an increase in the rate of responding under punishment) at doses that fail to disrupt unpunished responding. Furthermore, these same active drugs produce an anxiolytic-like effect in the absence of actual punishment, i.e. when the rate of lever pressing is reduced by conditioned fear of punishment. The conflict task does not require conditioned behavioral responses: naive thirsty animals can be offered the opportunity to drink, with drinking punished via contact with an electrified spout. Such punishment-suppressed drinking is disinhibited dose-dependently by benzodiazepine receptor agonists (e.g., diazepam). Exploratory activity can likewise be decreased by contingent punishment and released by treatment with known anxiolytics. Conflict models without punishment are based on the presence of the natural opposing motivational states, on the one hand the tendency to explore and, on the other hand, fear of a novel environment (e.g. dark-light chamber task, elevated plus-maze, consumption of unfamiliar food or normal food in an unfamiliar environment, social interaction between animals unfamiliar with each other). While it is obvious to ascribe the behavioral disinhibitory effect of benzodiazepine receptor agonism in these experimental situations to an anxiolytic-like action, their effect can also be interpreted as a general reduction of the influence of aversive factors or even to an impaired ability to withhold innate or conditioned responses. An anti-frustration effect resulting from benzodiazepine receptor agonism is suggested by the increase of responding which is maintained by response-contingent reward in the situation in which the reward is reduced or omitted. Electrical stimulation of the periaqueductal gray area of the midbrain via chronically implanted electrodes in animals is aversive and elicits a number of emotional reactions; benzodiazepine receptor agonists increase the aversive threshold. States of acute anxiety characterised by behavioral and physiological symptoms (cardiovascular, endocrine) can be induced by chemicals known to be anxiogenic in man, e.g. convulsants such as pentylenetetrazol, inverse agonists at the benzodiazepine receptor agonists administered in subconvulsive doses, or even abrupt drug withdrawal after chronic treatment with high doses of sedatives. Ultrasonic distress cries by rat pups acutely separated from their mothers are decreased by benzodiazepine receptor agonists.

Screening for Antidepressant Activity

Animal models for depression are also well known to those of ordinary skill in the art. For instance, the effect of the compound of the invention in the treatment of depression can be tested in the model of chronic mild stress induced anhedonia in rats. This model is based on the observation that chronic mild stress causes a gradual decrease in sensitivity to rewards, for example consumption of sucrose, and that this decrease is dose-dependently reversed by chronic treatment with antidepressants. The method has previously been described and more information with respect to the test appears from Willner, Paul, Psychopharmacology, 1997, 134, 319-329.

Another test for antidepressant activity is the forced swimming test (*Nature* 266, 730-732, 1977) In this test, animals are administered an agent preferably by the intraperitoneal route or by the oral route 30 or 60 minutes before the test. The animals are placed in a crystallizing dish filled with water and the time during which they remain immobile is clocked. The immobility time is then compared with that of the control group treated with distilled water. Imipramine 25 mg/kg can be used as the positive control. The antidepressant compounds decrease the immobility time of the mice thus immersed.

Another test for antidepressant activity is the caudal suspension test on the mouse (*Psychopharmacology*, 85, 367-370, 1985) In this test, animals are preferably treated with the study compound by the intraperitoneal route or by the oral route 30 or 60 minutes before the test. The animals are then suspended by the tail and their immobility time is automatically recorded by a computer system. The immobility times are then compared with those of a control group treated with distilled water. Imipramine 25 mg/kg can be used as the positive control. Antidepressant compounds decrease the immobility time of the mice.

Another test for screening antidepressants is the DRL-72 TEST. This test, carried out according to the protocol of Andrews et al ["Effects of imipramine and mirtazapine on operant performance in rats"—*Drug Development Research* 32, 58-66 (1994)], gives an indication of antidepressant-like activity. See also U.S. Pat. No. 6,403,573.

Additional animal models for screening are well known to one of ordinary skill in the art. For instance, see U.S. Pat. No. 5,952,315.

Methods for Screening for Anticonvulsant and Antiepilepsy Activity

Animals models are available to one of ordinary skill in the art for studying anticonvulsant activity of test compounds. See for instance, U.S. Pat. No. 6,309,406 and U.S. Pat. No. 6,326,156 which describe methods for performing such tests. In addition, the compounds may be administered to humans suffering from epilepsy or other convulsive conditions and the effect on the frequency or severity or onset of convulsions clinically assessed.

Methods for Screening for Sleep Promoting or Soporific Properties

Inhibition of FAAH has been reported to induce sleep in test animals (U.S. Pat. No. 6,096,784). Methods for studying sleep inducing compounds are well known to one of ordinary skill in the art. In particular, methods for testing the ability of a test FAAH inhibitory compound to induce sleep or treat insomnia are also disclosed in U.S. Pat. No. 6,096,784 and U.S. Pat. No. 6,271,015. Most obviously, the compounds can be administered to a test animal (e.g., rat or mouse) or a human and the subsequent time (e.g., onset, duration) spent sleeping (e.g., eyes closed, motor quiescence) can be monitored. See also WO 98/24396.

Methods for Screening Compounds which Induce Catalepsy or Affect Motor Activity

Methods for screening FAAH inhibitors which induce catalepsy are also well known to one of ordinary in the art. See Quistand et al. in *Toxicology and Applied Pharmacology* 173: 48-55 (2001). See Cravatt et al. *Proc. Natl. Acad. Sci. U.S.A.* 98:9371-9376 (2001).

Methods for Screening Compounds for Antinociceptive Activity

Methods for screening FAAH inhibitors for an antinociceptive effect are well known to one of ordinary in the art. For instance, the test compounds can be administered to the subject animals in the mouse hot-plate test and the mouse formalin test and the nociceptive reactions to thermal or chemical tissue damage measured. See also U.S. Pat. No. 6,326,156 which teaches methods of screening for antinociceptive activity. See Cravatt et al. *Proc. Natl. Acad. Sci. U.S.A.* 98:9371-9376 (2001).

Methods for Assessing the Effect of a FAAH Inhibitor on an Appetite

Compounds of the invention can be administered to an animal to determine whether they affect food intake and body weight, body fat, appetite, food seeking behavior, or modulate modulator fatty acid oxidation. Method of conducting such tests are known to one of ordinary skill in the art. For instance, see U.S. Patent Application No. 60/336,289 assigned to the same assignee and herein incorporated by reference in its entirety.

Animals can be, for example, obese or normal guinea pigs, rats, mice, or rabbits. Suitable rats include, for example, Zucker rats. Suitable mice include, for example, normal mice, ALS/LtJ, C3.SW-H-$2b$/SnJ, (NON/LtJ×NZO/HU)F1, NZO/HlJ, ALR/LtJ, NON/LtJ, KK.Cg-AALR/LtJ, NON/LtJ, KK.Cg-A$^{y}$/J, B6.HRS(BKS)-Cpe$^{fat}$/+, B6.129P2-Gck$^{tm/Efr}$, B6.V-Lep$^{ob}$, BKS.Cg-m+/+Lep$^{rdb}$, and C57BL/6J with Diet Induced Obesity.

Administration of an appropriate amount the candidate compound may be by any means known in the art such as, for example, oral or rectal, parenteral such as, for example, intraperitoneal, intravenous, subcutaneous, subdermal, intranasal, or intramuscular. Preferably administration may be intraperitoneal or oral. An appropriate effective amount of the candidate compound may be determined empirically as is known in the art.

Other methods of assessing appetitive behavior are known to one of ordinary skill in the art. For instance, Maruani et al. (U.S. Pat. No. 6,344,474) teach two such assays. One method of assessing the effect on appetite behavior is to administer a FAAH inhibitor to a rat and assess its effect on the intake of a sucrose solution. This method is taught in W. C. Lynch et al., *Physiol. Behav.*, 1993, 54, 877-880. Male Sprague-Dawley rats weighing 190 to 210 g are under a normal light cycle (from 7 am to 7 pm) and receive water and food ad libitum. For 6 days, between 11 am and 3 pm, the food and the water bottles are withdrawn and the rats are given a 5% sucrose solution to drink. Rats drinking less than 3 g of sucrose solution are eliminated. On the seventh day the test is carried out according to the following procedure: 9 am: withdrawal of food, 10 am: administration of the inhibitor or vehicle to the test animals; 11 am=T0: introduction of bottles containing a weighed sucrose solution, T0+1 hour, T0+2 hours, T0+3 hours, T0+4 hours: measurement of the sucrose consumption by weighing of the bottles. Followed by comparison of the experimental and control groups' intake of the sucrose solution.

In another test, the effect of a FAAH inhibitor on the consumption of an alcohol solution can be assessed in mice. For instance, male C 57 BL 6 mice are isolated on the day of their arrival in an animal housing under a reverse cycle (night from 10 am to 10 pm) with 2 bottles filled with water. After 1 week, one of the bottles of water is replaced with a bottle filled with a 10% alcohol solution for 6 hours of the test. Each day, 30 minutes before the bottle of alcohol is introduced, the mice are treated with a FAAH inhibitor. The amounts of alcohol and water consumed are measured after 6 hours. The test is repeated for 4 days.

The results for an experimental and a control or vehicle are compared.

Methods for Screening for Antipsychotic or Antischizophrenic or Dopamine-Modulating Activity Without being wed to theory, it is believed that excessive dopamine transmission in the CNS may contribute to schizophrenia and other mental disorders. Approximately one-third of all schizophrenic patients manifest obvious dopamine transmitter and/or receptor increases. Others who do not overtly manifest this abnormality still show improvement of symptoms with the pharmacological blockade of dopamine receptors. These dopamine receptor antagonists ultimately result in overall reductions in dopamine concentrations due to depolarization block and dopamine receptor antagonism. Thus, malfunction of neural circuits, many of which dopamine has a direct and/or indirect role in activating, appears to be involved in schizophrenic symptoms. As has been shown above, blocking dopamine receptors in subcortical areas of the brain substantially reduces schizophrenic symptoms. Generalized reduction of dopamine production in these areas provides similar relief to patients suffering from this disease. Cannabinoids have been found to modulate dopamine activity in the CNS.

Methods for screening compound for their effects on dopaminergic transmission and systems in the CNS are well known to one of ordinary skill in the art. Methods for conducting clinical trials of candidate agents in any of the above neurological diseases, disorders and conditions are well known to one of ordinary skill in the art.

Glaucoma

Methods of measuring the intraocular pressure of the eye with respect to the treatment of glaucoma are routine in the medical arts and may be readily and safely performed used human or animal subjects. The effect of a FAAH inhibitor on subject eye pressure can be readily assessed by applying the compound directly to the eye and monitoring eye pressure over the next several hours or day. The alternate eye may be used as a control. Alternatively the FAAH inhibitor may be given systemically and another vehicle treated subject used as the control.

Methods of Use, Pharmaceutical Compositions, and their Administration

Methods of Use

Anxiety and Anxiety Related Disorders

In some embodiments, the FAAH inhibitory compounds, including the compounds of Formula I and II, and their pharmaceutical compositions and methods of administering them are useful in treating anxiety and anxiety disorders or conditions. The compounds and compositions are useful, for example in treating anxiety, clinical anxiety, panic disorder, agoraphobia, generalized anxiety disorder, specific phobia, social phobia, obsessive-compulsive disorder, acute stress disorder, and post-traumatic stress disorder; and adjustment disorders with anxious features, anxiety disorders due to general medical conditions, substance-induced anxiety disorders, and the residual category of anxiety disorder not otherwise specified. The treatment may be prophylactic or therapeutic. The treatment may be administered to a human subject. The compounds may be used in otherwise healthy individuals who are not otherwise in need of any pharmaceutical intervention for a disease or condition such as insomnia or for pain relief.

In some embodiments, the compounds methods, and compositions of the invention may also be administered to treat anxiety in mammals, including cats, dogs, and humans. In some embodiments, the compounds may be used in otherwise healthy individuals who are not in need of pharmaceutical interventions for any other disease or disorder than anxiety or an anxiety disorder. In some embodiments, the subject is not otherwise in need of a FAAH inhibitor.

The compounds and compositions of the invention may be administered solely for the purposes of reducing the severity or frequency of anxiety or an anxiety disorder.

Preferred inhibitors for such uses are UCM532 and UCM597.

Depression and Depressive Disorders

In some embodiments, the FAAH inhibitory compounds of Formula I and II, their pharmaceutical compositions and methods of administering them are useful in treating depression and depressive disorders or conditions. The compounds and compositions are useful, for example in treating major depressive disorders (unipolar depression), dysthymic disorders (chronic, mild depression), and bipolar disorders (manic-depression). The depression may be clinical or subclinical depression. The treatment may be prophylactic or therapeutic. The treatment may be administered to a human subject. The compounds may be used in otherwise healthy individuals who are not otherwise in need of any pharmaceutical intervention for a disease such as insomnia or for pain relief.

In some embodiments, the compounds methods, and compositions of the invention may also be administered to treat depression in mammals, including cats, dogs, and humans. In some embodiments, the compounds may be used in otherwise healthy individuals who are not in need of pharmaceutical interventions for any other disease or disorder than depression or a depressive disorder. In some embodiments, the subject is not otherwise in need of a FAAH inhibitor.

The compounds and compositions of the invention may be administered solely for the purposes of reducing the severity or frequency of depression or a depressive disorder.

Preferred inhibitors for such uses are UCM532 and UCM597.

Seizure Disorders

In some embodiments, the FAAH inhibitory compounds, their pharmaceutical compositions and methods of administering them are useful in treating epilepsy and convulsive disorders or seizures. The treatment may be prophylactic or therapeutic. The treatment may be administered to a human subject. The compounds may be used in otherwise healthy individuals who are not otherwise in need of any pharmaceutical intervention for a disease such as insomnia or pain relief.

In some embodiments, the compounds methods, and compositions of the invention may also be administered to treat such diseases and disorders in mammals, including cats, dogs, and humans. In some embodiments, the compounds may be used in otherwise healthy individuals who are not in need of pharmaceutical interventions for any other disease or disorder than a seizure disorder. In some embodiments, the subject is not otherwise in need of a FAAH inhibitor.

The compounds and compositions of the invention may be administered solely for the purposes of reducing the severity or frequency of convulsions or seizures.

Preferred inhibitors for such uses are UCM532 and UCM597.

Use of FAAH Inhibitors to Control of Appetite and Treatment of Appetite Disorders In some embodiments, the invention provides pharmaceutical compositions and methods of using FAAH inhibitory compound to reduce appetite(s), reduce body fat and for treating or preventing obesity or overweight in a mammal and for preventing or treating the diseases associated with these health conditions. In one aspect of the instant invention, methods are provided for reducing appetite, body fat or body weight, or for treating or preventing obesity or overweight, or for reducing food intake, or treating an appetency disorder in a mammal by administering to the mammal a FAAH inhibitor, including inhibitors according to Formula I and Formula II. In a further embodiment, the inhibitor is administered in a combination therapy with oleoylethanolamide (OEA) or another fatty acid alkanolamide compound, or a homologue or analog of oleylethanolamide or the fatty acid alkanolamide compound, which reduces appetite or food consumption and is subject to hydrolysis by FAAH.

In some embodiments, the FAAH inhibitor is administered to a subject in amounts sufficient to reduce body fat, body weight, or prevent body fat or body weight gain or to reduce appetite(s). In another aspect of the invention, pharmaceutical compositions are provided which comprise a first compound which is a FAAH inhibitor and a second compound which is oleylethanolamide or a fatty acid alkanolamide compound, or a homologue or analog of oleylethanolamide or the fatty acid alkanolamide compound which reduces appetite or which has an effect to reduce appetite. In other aspects, the invention is drawn to such pharmaceutical compositions and their methods of use to reduce or control appetite or to treat appetite disorders.

In some aspects, the invention provides method of treating an appetency disorder comprising administration of a first compound which is a FAAH inhibitor and a second compound which is a fatty acid alkanolamide compound, homologue or OEA analog which is not a significant antagonist of the cannabinoid CB1 receptor and is administered in an amount which does not by itself significantly activate or inhibit the CB1 receptor. In another aspect of the invention, pharmaceutical compositions are provided which comprise a first compound which is a FAAH inhibitor and a second compound which is oleylethanolamide (OEA) or a fatty acid alkanolamide compound, or a homologue or analog of oleylethanolamide or the fatty acid alkanolamide compound, which is not a significant CB1 cannabinoid receptor antagonist and which reduces appetite or which has an effect to reduce appetite which is not substantially mediated by binding of the second compound to the CB1 cannabinoid receptor. In other aspects, the invention is drawn to such pharmaceutical compositions and their methods of use to reduce or control appetite and to treat appetite disorders.

Preferred inhibitors for such uses are UCM532 and UCM597.

Schizophrenia and Dopamine Related Disorders

Is some embodiments, the FAAH inhibitory compounds according to Formula I or Formula II, their pharmaceutical compositions and methods of administering them are useful in treating schizophrenia and dopamine related disorders. The treatment may be prophylactic or therapeutic. The treatment may be administered to a human subject. The compounds may be used in otherwise healthy individuals who are not otherwise in need of any pharmaceutical intervention for a disease such as insomnia or hyperalgesia. In some embodiments, the compounds may be used in otherwise healthy individuals who are not in need of pharmaceutical interventions for any other disease or disorder than a seizure disorder. In some embodiments, the subject is not otherwise in need of a FAAH inhibitor.

The compounds and compositions of the invention may be administered solely for the purposes of reducing the severity or frequency of the schizophrenia or dopamine related disorder. They may be administered to reduce paranoid ideation and flat affect.

Preferred inhibitors for such uses are UCM532 and UCM597.

Use to Induce Sleep

In some embodiments, the compounds of Formula I and II may be administered to induce or promote sleep in a mammalian subject. The treatment may be prophylactic or therapeutic. The treatment may be administered to a human subject. The compounds and compositions of the invention may be administered solely for the purposes of reducing the severity or frequency or extent of sleeplessness.

Another aspect of the invention is directed to a method for inhibiting oleamide hydrolysis by FAAH. The method employs the act of contacting or combining the FAAH with an inhibitor. The inhibitor is according to Formula I or Formula II.

Another aspect of the invention is directed to a method for inducing sleep within an oleamide sensitive animal. More particularly, this aspect of the invention is directed to the administration to an oleamide sensitive animal of an effective dose of an agonist of oleamide hydrolase. Preferred inhibitors for such uses are UCM532 and UCM597.

Control of Pain

In some embodiments, the compounds of Formula I and II may be administered to alleviate pain in a subject. The treatment may be prophylactic or therapeutic. The treatment may be administered to a human subject. The compounds and compositions of the invention may be administered solely for the purposes of reducing the severity or frequency or extent of pain. The treatment may be administered in a combination therapy with another pain reliever or antiinflammatory agent.

Glaucoma

In some embodiments, FAAH inhibitors may be administered to treat or prevent glaucoma or to reduce intraocular eye pressure. In some embodiments, the compounds may be given systemically. In other embodiments, the FAAH inhibitors are direct applied to the surface of the eye (e.g., via eye drops).

Pharmaceutical Compositions

Another aspect of the present invention provides pharmaceutical compositions which comprise compounds of the invention and a pharmaceutically acceptable carrier.

The pharmaceutical compositions of the present invention comprise a compound of the instant invention as an active ingredient or a pharmaceutically acceptable salt thereof, and may also contain a pharmaceutically acceptable carrier and optionally other therapeutic ingredients. In some embodiments, the compositions comprise a compound of Formula I or Formula II.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend in part on the nature and severity of the conditions being treated and on the nature of the active ingredient. An exemplary route of administration is the oral route. The compositions may be conveniently presented in unit dosage form and prepared by any of the methods well-known in the art of pharmacy.

In practical use, the compounds of the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations can contain at least 0.1 percent of active compound. The percentage of active compound in these compositions may, of course, be varied and may conveniently be between about 2 percent to about 60 percent of the weight of the unit. The amount of active compound in such therapeutically useful compositions is such that a therapeutically effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. To prevent breakdown during transit through the upper portion of the GI tract, the composition may be an enteric coated formulation.

With respect to formulations with respect to any variety of routes of administration, methods and formulations for the administration of drugs are disclosed in Remington's Pharmaceutical Sciences, 17th Edition, (Gennaro et al. Eds., Mack Publishing Co., 1985). Remington's Pharmaceutical Sciences, Gennaro A R ed. 20th edition, 2000: Williams & Wilkins PA, USA.

Administration

The compounds of the invention may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of the invention can be effective over a wide dosage range. For example, in the treatment of adult humans, dosages from about 10 to about 1000 mg, about 100 to about 500 mg or about 1 to about 100 mg may be needed. Doses of the 0.05 to about 100 mg, and more preferably from about 0.1 to about 100 mg, per day may be used. A most preferable dosage is about 0.1 mg to about 70 mg per day. In choosing a regimen for patients, it may frequently be necessary to begin with a dosage of from about 2 to about 70 mg per day and when the condition is under control to reduce the dosage as low as from about 0.1 to about 10 mg per day. For example, in the treatment of adult humans, dosages from about 0.05 to about 100 mg, preferably from about 0.1 to about 100 mg, per day may be used. The exact dosage will depend upon the mode of administration, on the therapy desired, form in which administered, the subject to be treated and the body weight of the subject to be treated, and the preference and experience of the physician or veterinarian in charge.

Generally, the compounds of the present invention can be dispensed in unit dosage form comprising preferably from about 0.1 to about 100 mg of active ingredient together with a pharmaceutically acceptable carrier per unit dosage. Usually, dosage forms suitable for oral, nasal, pulmonary or transdermal administration comprise from about 0.001 mg to about 100 mg, preferably from about 0.01 mg to about 50 mg of the compounds admixed with a pharmaceutically acceptable carrier or diluent. For storage and use, these preparations preferably contain a preservative to prevent the growth of microorganisms.

Administration of an appropriate amount the candidate compound may be by any means known in the art such as, for example, oral or rectal, parenteral, intraperitoneal, intravenous, subcutaneous, subdermal, intranasal, or intramuscular. In some embodiments, administration is transdermal. An appropriate amount or dose of the candidate compound may be determined empirically as is known in the art. An appropriate or therapeutic amount is an amount sufficient to effect a loss of body fat or a loss in body weight in the animal over time. The candidate compound can be administered as often as required to effect a loss of body fat or loss in body weight, for example, hourly, every six, eight, twelve, or eighteen hours, daily, or weekly Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Injection solutions and suspensions can be prepared from sterile powders, granules, and tablets of the kind previously described. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

With respect to transdermal routes of administration, methods for transdermal administration of drugs are disclosed in Remington's Pharmaceutical Sciences, Gennaro A R ed. 20th edition, 2000: Williams & Wilkins PA, USA. Dermal or skin patches are a preferred means for transdermal delivery of the compounds of the invention. Patches preferably provide an absorption enhancer such as DMSO to increase the absorption of the compounds. Other methods for transdermal drug delivery are disclosed in U.S. Pat. Nos. 5,962,012, 6,261,595, and 6,261,595. Each of which is incorporated by reference in its entirety.

Preferred patches include those that control the rate of drug delivery to the skin. Patches may provide a variety of dosing systems including a reservoir system or a monolithic system, respectively. The reservoir design may, for example, have four layers: the adhesive layer that directly contacts the skin, the control membrane, which controls the diffusion of drug molecules, the reservoir of drug molecules, and a water-resistant backing. Such a design delivers uniform amounts of the drug over a specified time period, the rate of delivery has to be less than the saturation limit of different types of skin.

The monolithic design, for example, typically has only three layers: the adhesive layer, a polymer matrix containing the compound, and a water-proof backing. This design brings a saturating amount of drug to the skin. Thereby, delivery is controlled by the skin. As the drug amount decreases in the patch to below the saturating level, the delivery rate falls.

Compounds of the invention may be used in combination with other compounds of the invention or with other drugs that may also be useful in the treatment, prevention, suppression of a neurological or psychological disorder. In one embodiment, the second drug is not a FAAH inhibitor and is directed toward the same disorder as the fatty acid amide inhibitor. Such other drugs may be administered, by a route and in an amount commonly used therefor, contemporaneously or sequentially with a compound of the invention.

When a compound of the invention is used contemporaneously with one or more other drugs, a pharmaceutical composition in unit dosage form containing such other drugs and the compound is preferred. When used in combination with one or more other active ingredients, the compound of the present invention and the other active ingredients may be used in lower doses than when each is used singly. Accordingly, the pharmaceutical compositions of the present invention include those that contain one or more other active ingredients, in addition to the compounds disclosed above. For example, a FAAH inhibitor according to Formula I or Formula II may be formulated with an anxiolytic agent which is not a FAAH inhibitor. For example, a FAAH inhibitor according to Formula I or Formula II may be formulated with an antidepressant.

In the pharmaceutical compositions of the present invention for oral, sublingual, subcutaneous, intramuscular, intravenous, transdermal, local or rectal administration, the active principle, by itself or in association with another active principle, can be administered to animals and humans in unit forms of administration mixed with conventional pharmaceutical carriers. The appropriate unit forms of administration include oral forms such as tablets, gelatin capsules, powders, granules and solutions or suspensions to be taken orally, sublingual and buccal forms of administration, aerosols, implants, subcutaneous, intramuscular, intravenous, intranasal or intraocular forms of administration and rectal forms of administration.

In other embodiments, the pharmaceutical compositions of the present invention, the active principle or active principles are generally formulated in dosage units. The dosage unit contains from 0.5 to 1000 mg, advantageously from 1 to 500 mg and preferably from 2 to 200 mg of FAAH inhibitor per dosage unit for daily administration.

When used to treat glaucoma, direct application to the eye is preferred. Ocular carrier formulations for such ocular application are taught in Remington's Pharmaceutical Sciences, Gennaro A R ed. 20th edition, 2000: Williams & Wilkins PA, USA.

The following examples are provided for illustrative purposes, and are not intended to limit the scope of the invention as claimed herein. Any variations in the exemplified articles and/or methods which occur to the skilled artisan are intended to fall within the scope of the present invention.

EXAMPLES

Example 1

Subjects

We used male and female Wistar rats (200-350 g) and male Swiss mice (20 g). All procedures met the National Institutes of Health guidelines for the care and use of laboratory animals, and those of the Italian Ministry of Health (D.L. 116/92). We prepared primary cultures of cortical neurons from 18-day-old Wistar rat embryos, and maintained them as described (Stella, N. et al., *Eur. J. Pharmacol.*, 425, 189-196 (2001)); we purchased human astrocytoma cells from American Type Culture Collection (Manassas, Va.).

Example 2

Chemicals

Anandamide and related lipids were synthesized in the laboratory (Giuffrida, A. et al., *Anal. Biochem.*, 280, 87-93 (2000)). SR141716A (rimonabant) was provided by RBI (Natick, Mass.) as part of the Chemical Synthesis Program of the National Institutes of Health; AM404 was from Tocris (Avonmouth, UK) and other drugs from Sigma (St. Louis, Mo.). All chemicals necessary for the preparation of inhibitors were from Aldrich.

Example 3

Synthesis of Inhibitors n-Butylcarbamic acid 4-benzyloxyphenyl ester (UCM532) (4) and 4-fluorophenylcarbamic acid 4-benzyloxyphenyl ester (8) were obtained by treatment of 4-benzyloxyphenol with n-butylisocyanate, and 4-fluorophenylisocyanate, respectively, with a catalytic amount of triethylamine in refluxing toluene. Similarly, cyclohexylcarbamic acid biphenyl-3-yl ester (5), cyclohexylcarbamic acid 5-phenylpentyl ester (7), and cyclohexylcarbamic acid 3'-carbamoylbiphenyl-3-yl ester (UCM597) (6) were synthesized by reacting cyclohexylisocyanate with 3-phenylphenol, 5-phenylpentan-1-ol, and 3'-hydroxybiphenyl-3-carboxylic acid amide, respectively. The latter reactant was prepared as follows: 3-bromobenzoic acid amide, obtained by reaction of 3-bromobenzonitrile and sodium perborate, was coupled with methoxyphenylboronic acid to give 3'-methoxybiphenyl-3-carboxylic acid amide, which was hydrolized with $BBr_3$ to generate the desired 3'-hydroxybiphenyl-3-carboxylic acid amide.

3-Bromobenzoic acid amide. To a solution of 3-bromobenzonitrile (0.91 g, 5 mmol) in dioxane (19 mL), $NaBO_3.4H_2O$ (2.12 g, 13.78 mmol) and $H_2O$ (19 mL) were added. The mixture was stirred at 80° C. 16 hours (h), cooled, added of $H_2O$ and extracted with $CH_2Cl_2$. The combined organic layers were dried over $Na_2SO_4$ and evaporated. Purification of the residue by column chromatography (hexane/EtOAc 2:8) and recrystallization gave the desired product as colorless tablets. Yield 80% (EtOH). Mp: 156-7° C. (lit. 156° C.) (Pearson, D. E. et al., *J. Org. Chem.*, 28: 3147-3149, (1963)). MS (EI): m/z 199 ($M^+$); 183 (100%).

3'-Methoxybiphenyl-3-carboxylic acid amide. To a stirred mixture 3-bromobenzoic acid amide (0.76 g; 3.8 mmol) and toluene (25 mL), $Pd(PPh_3)_4$ (0.180 g; 0.16 mmol), a solution of $Na_2CO_3$ (2.543 g; 24 mmol) in $H_2O$ (10 mL), and one of 3-methoxyphenylboronic acid (1.132 g; 7.45 mmol) in EtOH (10 mL) were added. The mixture was refluxed for 1 h under vigorous stirring, cooled, and the aqueous phase extracted with AcOEt. The combined organic layers were dried over $Na_2SO_4$ and concentrated. Purification of the residue by column chromatography (cyclohexane/EtOAc 1:1 then 4:6) and recrystallization gave the desired product (0.64 g) as white solid. Yield 74%. Mp: 138-40° C. (EtOH). MS (EI): m/z 227 ($M^+$, 100%). $^1H$ NMR ($CDCl_3$): δ 3.88 (s, 3H); 5.71 (br s, 1H); 6.11 (br s, 1H); 6.94 (m, 1H); 7.18 (m, 2H); 7.39 (t, 1H); 7.53 (t, 1H); 7.77 (m, 2H); 8.05 (t, 1H) ppm. IR (Nujol): 3327, 3148, 1676, 1640, 1613, 1584 $cm^{-1}$.

3'-Hydroxybiphenyl-3-carboxylic acid amide. To a stirred, cooled (0° C.) solution of 3'-methoxybiphenyl-3-carboxylic acid amide (0.57 g; 2.5 mmol) in dry $CH_2Cl_2$ (28 mL), under $N_2$ atmosphere, a 1M solution of $BBr_3$ in $CH_2Cl_2$ (6.4 mL) was added. The mixture was stirred at room temperature for 1 h, quenched with 2N $Na_2CO_3$ and extracted with AcOEt. The combined organic layers were washed with brine, dried over $Na_2SO_4$ and concentrated. Purification of residue by column chromatography (cyclohexane/EtOAc 2:8) gave the desired product as an amorphous solid. Yield 91%. Mp: 148-51° C. (after digestion with i-$Pr_2O$). MS (EI): m/z 213 ($M^+$, 100%).

$^1$H NMR (CDCl$_3$/d$_6$-DMSO): δ 6.06 (br s, 1H); 6.59 (m, 1H); 6.85 (m, 2H); 7.01 (t, 1H); 7.23 (t, 1H); 7.35 (br s, 1H); 7.45 (m, 1H); 7.60 (m, 1H) 7.88 (s, 1H); 8.80 (s, 1H) ppm. IR (Nujol): 3314, 3141, 1669, 1630, 1607, 1577 cm$^{-1}$.

Cyclohexylcarbamic acid 3'-carbamoylbiphenyl-3-yl ester. To a stirred mixture of 3'-hydroxybiphenyl-3-carboxylic acid amide (0.43 g, 2 mmol) in toluene (12 mL), Et$_3$N (0.012 g, 0.016 mL, 0.12 mmol), and cyclohexyl isocyanate (0.28 g, 0.28 mL, 2.2 mmol) were added. After refluxing for 20 h, the mixture was cooled and concentrated. Purification of the residue by column chromatography (cyclohexane/EtOAc 4:6) and recrystallization gave 5a as a white solid. An amount of unreacted 4a (0.07 g, 17%) was also recovered. Yield: 33%. Mp: 178° C. (EtOH) (sealed capillar tube). MS (EI): m/z 213 (100%). $^1$H NMR (CDCl$_3$): δ 1.17-1.43 (m, 6H); 1.76 (m, 2H); 2.04 (m, 2H); 3.57 (m, 1H); 4.97 (br d, 1H); 5.63 (br s, 1H); 6.14 (br s, 1H); 7.16 (m, 1H); 7.39-7.56 (m, 4H); 7.77 (m, 2H); 8.03 (s, 1H) ppm. IR (CHCl$_3$): 3301, 3142, 1693, 1666, 1627, 1604, 1573 cm$^{-1}$. Anal. calcd for C$_{20}$H$_{22}$N$_2$O$_3$ (338.41): C, 70.99; H, 6.55; N, 8.28. Found: C, 70.83; H, 6.65; N, 8.17.

Example 4

Molecular Modeling

Molecular modeling calculations, including conformational analysis, energy minimization and compound superposition were performed using a Sybyl 6.8 software (Tripos), employing the MMFF94s force field.

Example 5

Biochemical Assays

We prepared cell fractions from rat brain homogenates, and assayed membrane FAAH activity and cytosol MGL activity using anandamide [ethanolamine-3H] (American Radiolabeled Chemicals, ARC (St. Louis Mo.), 60 Ci/mmol) and 2-mono-oleoyl-glycerol-[glycerol-1,2,3-$^3$H] (ARC, St. Louis Mo., 20 Ci/mmol), respectively, as substrates (Dinh, T. Proc. Natl. Acad. Sci. U.S.A. (2002)). We conducted [$^3$H] anandamide transport assays in human astrocytoma cells (Piomelli, D. et al., Proc. Natl. Acad. Sci. U.S.A., 96, 5802-5807 (1999)); CB1 and CB2 binding assays in rat cerebellar membranes and CB2-overexpressing Chinese hamster ovary cells (Receptor Biology-Perkin Elmer, Wellesley, Mass.), respectively, using [$^3$H]WIN-55212-2 (NEN-Dupont, Boston, Mass., 40-60 Ci/mmol) as a ligand (Devane, W. A. et al. Science, 258, 1946-1949 (1992)); cholinesterase assays with a commercial kit (Sigma, St. Louis, Mo.), using purified enzymes (electric eel acetylcholinesterase type V-S and horse serum cholinesterase; both from Sigma, St. Louis, Mo.) and following manufacturer's instructions. To measure anandamide transport and hydrolysis in rat cortical neurons, we preincubated the cells with FAAH inhibitors at appropriate concentrations for 10 min at 37° C., prior to exposure to [$^3$H]anandamide for 4 min. In some experiments, we stopped the reactions with cold Tris-Krebs' buffer containing 0.1% bovine serum albumin (Type V, fatty acid free, Sigma, St. Louis, Mo.), removed the cells by trypsin-EDTA treatment, and extracted cell lipids with chloroform/methanol (1/1, vol/vol). We measured non-metabolized [$^3$H]anandamide in the organic phase of the extracts, and metabolized [$^3$H]anandamide (as [$^3$H]ethanolamine) in the aqueous phase. In other experiments, after having exposed the neurons to [$^3$H]anandamide for 4 min, we replaced the medium, rinsed the cells and measured [$^3$H]anandamide release into the medium as described above.

Example 6

High-Performance Liquid Chromatography/Mass Spectrometry (HPLC/MS)

We extracted lipids from tissues with a methanol-chloroform mixture and fractionated them by silica gel column chromatography (Giuffrida, A. et al., Anal. Biochem., 280, 87-93 (2000)). Anandamide and other fatty acid derivatives were quantified by HPLC/MS, using an isotope dilution method (Giuffrida, A. et al., Anal. Biochem., 280, 87-93 (2000)).

Example 7

Body Temperature and Catalepsy

We dissolved all compounds in saline/Tween 80/polyethylenglycol (90/5/5) and administered them by i.p. injection immediately before tests. We measured body temperature with a rectal probe (Type T, Copper-Costantan Thermocouple-Physitemp Instruments INC, Clifton, N.J.) connected to a digital thermometer (model BAT-12 Physitemp Instruments INC, Clifton, N.J.); and catalepsy using the procedure described in Tseng and Craft (Tseng, A. H. et al., Eur. J. Pharmacol., 430, 41-47 (2001)).

Example 8

Food Intake

We dissolved UCM597 in DMSO/saline (7/3) and administered it by i.p. injection 45 minutes before the test. We recorded food intake in free-feeding rats by using an automated system (Scipro Inc., New York). Rats were acclimated to the test cages for three days prior to the tests. Each test began at the onset of the dark phase and lasted for 24 hours.

Example 9

Antinociception

We dissolved FAAH inhibitors in polyethyleneglycol/water (1/1) and rimonabant in saline. Formalin and hot-plate assays were carried out in the mouse, as described (Beltramo, M. et al., FEBS Lett., 403, 263-267 (1997)).

Example 10

Anxiety and Motor Activity

We dissolved FAAH inhibitors and rimonabant in dimethylsulfoxide (DMSO)/saline (7/3 and 9/1, respectively); we administered FAAH inhibitors by i.p. injection 30 min before tests and rimonabant 30 min before UCM532. The elevated zero maze was comprised of a black Perspex annular platform (105 cm diameter, 10 cm width) elevated to 65 cm above ground level, divided equally into four quadrants (Bickerdike, M. J. et al., Eur. J. Pharmacol., 271, 403-411 (1994); Shepherd, J. K. et al., Psychopharmacology, 116, 56-64 (1994)). Two opposite quadrants were enclosed by black walls (27 cm high) on both the inner and outer edges of the platform, while the other two were surrounded only by a shallow edge (1 cm high). The apparatus was illuminated by uniform dim red light (40-60 lux). We placed the rats in a closed quadrant and video recorded them for 5-min periods, thoroughly cleaning the maze between sessions. Rats were considered to be in an open quadrant when their four paws were within the quadrant. Results are expressed as percent time in open quadrant/total time (percent time open). Results were analyzed by one-way ANOVA followed by Tukey's test. We recorded motor activity of each rat in an Opto-Varimex cage (Columbus Instruments, Columbus, Ohio) linked on-line to a computer and placed in a sound-attenuated room illuminated by a 20-W white light. The amount of time spent in ambulatory activity was analyzed using an Auto-Track software (Columbus Instruments, Columbus, Ohio) as described elsewhere (Ali, M. M. et al., *Neurosci. Lett.*, 284, 57-60 (2000); Wedzony, K. et al., *Neuropsychopharmacology*, 23, 547-559 (2000)). Session duration was 20 min for 10-days old adult rats and 60 s for 10-days old pups. We analyzed data by overall one-way ANOVA followed by Tukey's test for individual between-group comparisons. We recorded 10-days old pup ultrasonic vocalizations in a sound-attenuating chamber, following the procedure described by Cuomo et al. (Cuomo, V. et al., *Neuropharmacology*, 26, 701-705 (1987)). Tests were conducted between 900 and 1400 h and lasted for 15 s. Drugs were administered after baseline values collection (15 s) and pups were tested again 30 min after drug administration. Data were expressed as percent change from baseline and analysed by overall one-way ANOVA followed by Tukey's test for individual between-group comparisons.

Example 11

Lead Identification and Optimization

Despite its unusual catalytic mechanism (Patricelli, M. P. et al., *Biochemistry*, 38, 9804-9812 (1999)), FAAH is blocked by a variety of serine hydrolase inhibitors, including compounds with activated carbonyls (Boger, D. L. et al. *Proc. Natl. Acad. Sci. U.S.A.*, 97, 5044-5049 (2000)). Therefore we examined whether esters of carbamic acid such as the anticholinesterase agent carbaryl (Table 1, compound 1) may inhibit FAAH activity in rat brain membranes. Although 1 was ineffective, its positional isomer 2 produced a weak inhibition of FAAH (half-maximal inhibitory concentration, $IC_{50}=18.6\pm0.7$ μM; mean±SEM, n=3), which was enhanced by replacing the N-methyl substituent with a cyclohexyl group (3, $IC_{50}=324\pm31$ nM). The aryl ester 4, the benzyloxyphenyl group of which can be regarded as an elongated bioisosteric variant of the naphthyl moiety of 2, inhibited FAAH with a potency ($IC_{50}=396\pm63$ nM) equivalent to 3. A conformational analysis of 4 revealed families of accessible conformers differing mainly in the torsion angle around the O—$CH_2$ bond, with substituents in anti or gauche conformations (data not shown). As the latter conformations more closely resembled the shape of the naphthyl derivative 3, we hypothesized that they might be responsible for the interaction of 4 with the active site of FAAH. Testing this hypothesis led to the design of the biphenyl derivative 5 ($IC_{50}=63\pm9$ nM), which was further optimized by systematic modifications of the distal phenyl group, resulting in the potent inhibitor 6 ($IC_{50}=4.6\pm1.6$ nM) (Table 1).

Kinetic analyses and dialysis experiments suggest that compounds 4 and 6 may inhibit FAAH activity through an irreversible interaction with the enzyme (data not shown), possibly due to a nucleophilic attack of an active serine residue on the carbamate group. This mechanism sets the present compounds apart from the α-keto heterocycle derivatives described by Boger et al. (D. L. Boger et al., *Proc. Natl. Acad. Sci. U.S.A.*, 97, 5044-5049 (2000)), which act as competitive FAAH inhibitors. A further indication of such distinction is that in the α-keto heterocycle series potency is strongly dependent on the hydrophobicity of the flexible acyl chain, whereas in the carbamate series potency is modulated by the shape of the rigid aromatic moiety. Accordingly, when we replaced the biphenyl of 5 with a 5-phenylpentyl group, representing the most effective acyl chain in the α-keto heterocycle series, the inhibitory activity was lost (compound 7, Table 1).

Compounds 4 (UCM532) and 6 (UCM597) blocked the FAAH-catalyzed hydrolysis of exogenous [$^3$H]anandamide by intact cortical neurons in primary cultures, with $IC_{50}$ values that paralleled those obtained in membrane preparations (UCM532, 214±79 nM; UCM597, 0.50±0.05 nM; n=8) (FIG. 1a). By contrast, compound 7, a UCM532 analog that does not inhibit FAAH in membranes (Table 1), had no such effect (FIG. 1b). Moreover, UCM532 and UCM597 selectively impaired the breakdown of [$^3$H]anandamide without reducing its carrier-mediated uptake, causing non-metabolized [$^3$H]anandamide to accumulate in, and eventually exit from, the neurons. Thus, after a 4-min incubation with [$^3$H]anandamide, the intracellular content of non-metabolized [$^3$H] anandamide was markedly higher in inhibitor-treated than in control neurons (FIG. 1c). As expected, the anandamide transport blocker N-(4-hydroxyphenyl)arachidonamide (AM404) had an opposite effect, significantly reducing [$^3$H] anandamide internalization (Beltramo, M. et al., *FEBS Lett.*, 403, 263-267 (1997)) (FIG. 1c). When UCM597-treated neurons were exposed for 4 min to [$^3$H]anandamide and then incubated for 15 min in an [$^3$H]anandamide-free solution, 42.6±8.7% of the accumulated [$^3$H]anandamide was released back into the medium (n=3) (FIG. 1d). This process was linear with time (FIG. 1e) and was not inhibited by AM404 (FIG. 1d), suggesting that it occurred through passive diffusion rather than reverse transport. No such time-dependent release was observed in control neurons, the medium of which only contained residual levels of [$^3$H]anandamide carried over from the preincubation period. Together, these studies identify a novel class of carbamate inhibitors of FAAH activity, which potently block anandamide breakdown in intact brain neurons.

Example 12

Target Selectivity

UCM532 and UCM597 inhibited FAAH, but did not affect the activities of three additional serine hydrolases: electric eel acetylcholinesterase, horse plasma butyryl cholinesterase, and rat brain monoglyceride lipase (MGL) (Table 2). The lack of MGL inhibition is particularly noteworthy in light of the proposed role of this enzyme in the biological inactivation of 2-arachidonoylglycerol (2-AG) (Dinh, T. *Proc. Natl. Acad. Sci. U.S.A.* (2002)), another endogenous cannabinoid present in the brain (Mechoulam, R. et al. *Biochem. Pharmacol.*, 50, 83-90 (1995); Sugiura, T. et al., *Biochem. Biophys. Res. Commun.*, 215, 89-97 (1995); Stella, N. et al., *Nature*, 388, 773-778 (1997)). Furthermore, UCM532 and UCM597 had no effect on anandamide transport in human astrocytoma cells or on the binding of a high-affinity ligand to CB1 and CB2 receptors (Table 2). Even further, UCM532 (10 μM) did not significantly interact with a panel of 21 receptors, ion channels and neurotransmitter transporters, which included adenosine $A_1$, $A_{2A}$ and $A_{2B}$; adrenergic $\alpha_{1A}$, $\alpha_{2A}$, $\beta_1$ and $\beta_2$;

dopamine $D_1$ and $D_2$; glutamate N-methyl-(D)-aspartate; γ-amino-butyric acid $(GABA)_A$ agonist site; histamine $H_1$; opiate μ; muscarinic $M_2$; and brain nicotinic receptors (data not shown). This high selectivity for FAAH encouraged us to examine the effects of UCM532 and UCM597 in live animals.

Example 13

FAAH Inhibition In Vivo

Figure 2:
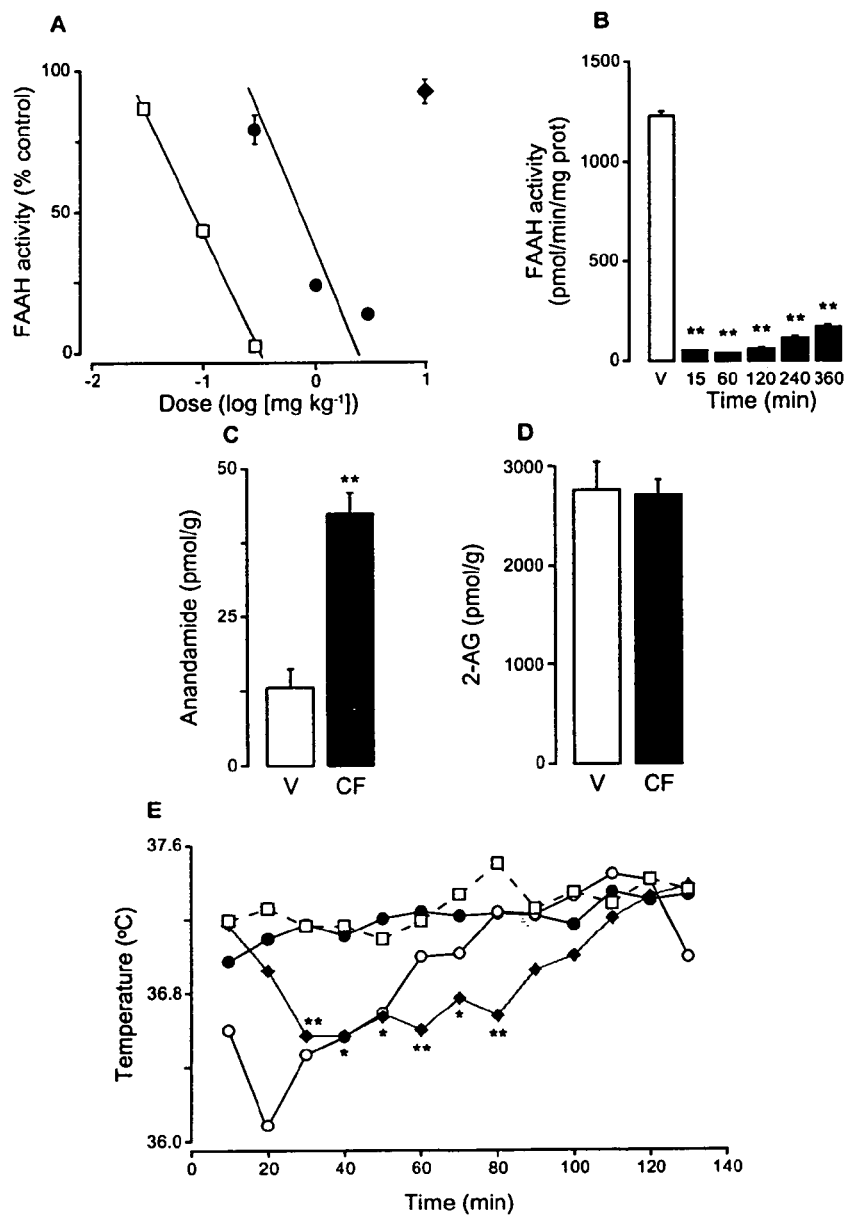
FIG. 2. In vivo inhibition of FAAH activity by UCM532 and UCM597. a, Dose-dependent inhibition of brain FAAH activity by UCM532 (closed circles) and UCM597 (open squares), but not by the inactive analog 7 (closed diamond), after systemic (i.p.) administration in the rat. b, Time-course of the inhibition of brain FAAH activity after a single injection of UCM597 (0.3 mg kg$^{-1}$, i.p.). Brain levels of anandamide (c) and 2-AG (d) 2 h after injections of vehicle (V) or UCM597 (CF, 0.3 mg kg$^{-1}$, i.p). One asterisk, $P<0.05$; two asterisks, $P<0.01$, ANOVA followed by Tukey's test; (n=4-8). e, Enhancement of anandamide-induced hypothermia by UCM597. Effects of UCM597 (0.3 mg kg$^{-1}$; open squares), anandamide (5 mg kg$^{-1}$; closed circles), anandamide (15 mg kg$^{-1}$; open circles), and anandamide (5 mg kg$^{-1}$) plus UCM597 (0.3 mg kg$^{-1}$, 30 min before anandamide) (closed diamonds). One asterisk (P<0.05) or two asterisks (P<0.01) indicate significant differences between anandamide and anandamide/UCM597; t-test with Bonferroni's correction (n=6-7).

Intraperitoneal (i.p.) injections of either UCM532 or UCM597, but not the inactive analog 7, produced a profound, dose-dependent inhibition of brain FAAH activity (FIG. 2a). In six experiments, half-maximal inhibition was reached at 0.60±0.09 mg $kg^{-1}$ UCM532 and 0.150±0.007 mg $kg^{-1}$ UCM597. After injection of a maximal dose of UCM597 (0.3 mg $kg^{-1}$, i.p.), FAAH inhibition was rapid in onset (<15 min), persistent (>6 h) (FIG. 2b), and accompanied by significant elevations in the brain content of anandamide (FIG. 2c) and other fatty acid ethanolamides that are substrates for FAAH (in pmol $g^{-1}$ of tissue at 2 h after injection; oleoylethanolamide: vehicle, 137.0±14.3; UCM597 0.3 mg $kg^{-1}$, 725.3±28.6; palmitoylethanolamide: vehicle, 259.1±15.0; UCM597, 1324±395; n=8-15). Parallel changes in FAAH activity and fatty acid ethanolamide levels were also measured in various peripheral tissues (data not shown). In agreement with the lack of MGL inhibition noted in our in vitro experiments (Table 2), UCM597 did not change the brain content of 2-AG (FIG. 2d).

As previously observed in mutant $FAAH^{-/-}$ mice (Cravatt, B. F. et al., Proc. Natl. Acad. Sci. U.S.A., 98, 9371-9376 (2001)), FAAH inhibition was associated with increased sensitivity to the administration of exogenous anandamide. Accordingly, UCM597 (0.3 mg $kg^{-1}$, i.p.) intensified and prolonged the decrease in body temperature elicited by a subthreshold dose of anandamide (5 mg $kg^{-1}$, i.p.), whereas it had no effect when injected alone (FIG. 2e) ($F_{treatments}$=38.36, df=1/143, P<0.0001; $F_{time}$=3.79, df=12/143, P<0.0001; $F_{timextreatments}$=2.64, df=12/143, P<0.005; two-way ANOVA of UCM597 versus anandamide plus UCM597).

Example 14

Antinociceptive Effects of FAAH Inhibitors

Figure 3:
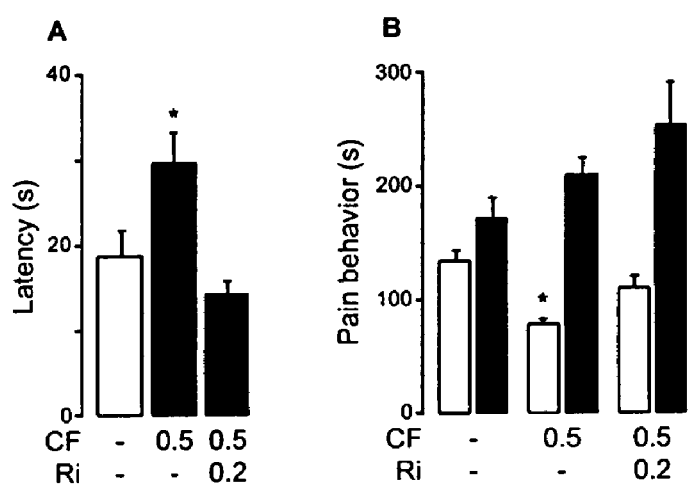
FIG. 3. Antinociceptive actions of UCM597. a, Effects of UCM597 (CF, 0.5 mg kg$^{-1}$, i.p.) on response latencies in the mouse hot-plate test, in the absence or presence of the CB1 antagonist rimonabant (Ri, 0.2 mg kg$^{-1}$, i.v.). b, Effects of UCM597 (0.5 mg kg$^{-1}$) on the early phase (open bars) and late phase (closed bars) of formalin-evoked pain, in the absence or presence of rimonabant. UCM597 and rimonabant were injected 60 min and 40 min before tests, respectively. One asterisk, P<0.05; ANOVA followed by Dunnett's test (n=12).

Though UCM532 and UCM597 increased brain anandamide levels, they did not overtly mimic the spectrum of pharmacological responses produced by exogenous anandamide. Systemic doses of UCM532 (10 mg $kg^{-1}$, i.p.) or UCM597 (0.3 mg $kg^{-1}$, i.p.) that maximally blocked FAAH activity produced no catalepsy (rigid immobility), hypothermia or hyperphagia (increased food intake), three typical signs of CBI receptor activation (Chaperon, F. et al., Crit. Rev. Neurobiol., 13, 243-281 (1999)) (data not shown). The compounds exerted, however, moderate antinociceptive effects in two models of acute pain. In the mouse hot-plate test, which measures the animal's response to noxious thermal stimuli, UCM597 significantly lengthened response latencies at a dose of 0.5 mg $kg^{-1}$ (FIG. 3a), but not at a lower dose (0.1 mg $kg^{-1}$; data not shown). Moreover, in the mouse formalin test, which measures nocifensive reactions to chemical tissue damage, UCM597 (0.5 mg $kg^{-1}$) attenuated the early phase of pain behavior, with little or no change in the late phase (FIG. 3b). Both effects were abrogated by the CB1 antagonist SR1417161A (rimonabant) (0.2 mg $kg^{-1}$, intravenous, i.v.) (FIGS. 3a and b) and mimicked, albeit less effectively, by UCM532 (data not shown). Our results corroborate those obtained in mutant $FAAH^{-/-}$ mice (Cravatt B. F. et al., Proc. Natl. Acad. Sci. U.S.A., 98, 9371-9376 (2001), indicating that acute disruption of FAAH activity results in moderate CB1-mediated antinociception, but no hypothermia or catalepsy.

Example 15

Anxiolytic Effects of FAAH Inhibitors

To identify other intrinsic actions of anandamide that might be magnified by FAAH inhibition, we turned to the regulation of emotional reactivity, for three reasons. First, CB1 receptors are expressed at high levels in brain regions, such as the amygdala, which are implicated in the control of anxiety and fear (Herkenham, M. et al., Proc. Natl. Acad. Sci. U.S.A., 87, 1932-1936 (1990); Glass, M. et al., Neuroscience, 77, 299-318 (1997); Katona, I. et al., J. Neurosci., 21, 9506-9518 (2001)). Second, acute administration of cannabinoid drugs produces marked emotional responses in rodents (Chaperon, F. et al., Crit. Rev. Neurobiol., 13, 243-281 (1999)) and humans (Hall, W. et al., Lancet, 352, 1611-1616 (1998); Robson, P. Br. J. Psychiatry, 178, 107-115 (2001)). Third, the CBI antagonist rimonabant elicits anxiety-like behaviors in rats, suggesting the existence of an intrinsic anxiolytic tone mediated by endogenous cannabinoids (Rodriguez de Fonseca, F. et al., Science, 276, 2050-2054 (1997); C. Arevalo, R. et al., Pharmacol. Biochem. Behav., 70, 123-131 (2001)).

Figure 4:
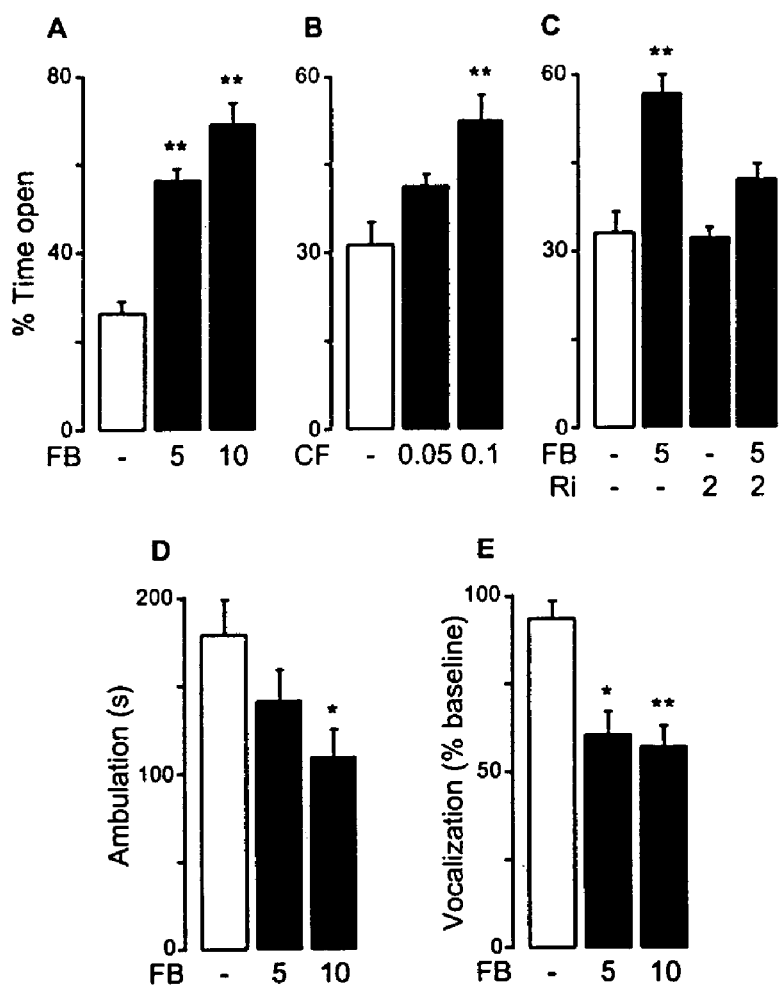
FIG. 4 Anxiolytic-like actions of UCM532 and UCM597. Dose-dependent effects of (a) UCM532 (FB, 5 and 10 mg kg$^{-1}$, i.p.) or (b) UCM597 (CF, 0.05 and 0.1 mg kg$^{-1}$, i.p.) on the percent time spent by adult rats in the open quadrants of a zero maze (percent time open). c, Effect of the CB1 antagonist rimonabant (2 mg kg$^{-1}$, i.p.) on the change in percent time open produced by UCM532 (5 mg kg$^{-1}$). d, Effects of UCM532 (5 and 10 mg kg$^{-1}$) on ambulation time in adult rats (20 min session). e, Effects of UCM532 (5 and 10 mg kg$^{-1}$) on isolation-induced ultrasonic vocalizations in rat pups. One asterisk, P<0.05; two asterisks, P<0.01 (n=7-10).

We used two pharmacologically validated animal models of anxiety, the elevated zero maze test, and the isolation-induced ultrasonic emission test. The zero maze consists of an elevated annular platform with two open and two closed quadrants and is based on the conflict between an animal's instinct to explore its environment and its fear of open spaces, where it may be attacked by predators (Bickerdike, M. J. et al., Eur. J. Pharmacol., 271, 403-411 (1994); Shepherd, J. K. et al., Psychopharmacology, 116, 56-64 (1994)). Clinically used anxiolytic drugs, such as the benzodiazepines, increase the proportion of time spent in, and the number of entries made into, the open compartments. Similarly, UCM532 (5 and 10 mg $kg^{-1}$, i.p.) and UCM597 (0.05-0.1 mg $kg^{-1}$, i.p.) evoked anxiolytic-like responses at doses that corresponded to those required to inhibit FAAH activity in vivo (FIG. 4 a and b) (F=38.58, df=2/27, P<0.001; F=7.7, df=2/27, P<0.01). In keeping with an involvement of endogenous anandamide, the anxiolytic-like effects of UCM532 were attenuated by a non-anxiogenic dose of the CBI antagonist rimonabant (2 mg $kg^{-1}$, i.p.) (FIG. 4c) (F=14.87, df=3/31, P<0.001). Moreover, the effects were apparently dissociated from overall changes in motor behavior. Indeed, although UCM532 elicited, in adult rats, a modest decrease in ambulation (which was also antagonized by rimonabant, data not shown), it did so at doses that were higher than those needed to cause anxiolysis (≧10 mg $kg^{-1}$) (FIG. 4d) (F=3.57, df=2/22, P<0.05). We confirmed this dissociation by testing UCM532 in the ultrasonic vocalization emission model, which measures the number of stress-induced vocalizations emitted by rat pups removed from their nest (Insel, T. R. et al., Pharmacol. Biochem. Behav., 24, 1263-1267 (1986); Miczek, K. A. et al., Psychopharmacology, 121, 38-56 (1995); Winslow, J. T. et al., Biol. Psychiatry, 15:745-757 (1991)). As seen with anxiolytic drugs, UCM532 strongly reduced ultrasonic calls (FIG. 4e) (F=12.27; df=2/18, P<0.001) at a dose (5 mg $kg^{-1}$) that had no effect on pup movement (data not shown) (F=3.23, df=2/18, n.s.).

Example 16

Overall Pharmacological Activity

The fatty acid amide hydrolase inhibitors of Formula I and Formula II represent a new class of agents that prevent anandamide inactivation by targeting the intracellular enzymatic activity of FAAH. UCM597, the most potent member of this class, inhibited FAAH activity with an $IC_{50}$ value of 4 nM in brain membranes and 0.5 nM in intact neurons, and an $ID_{50}$ value of 0.15 mg $kg^{-1}$ following systemic administration in the rat. This compound had much greater selectivity for FAAH than other cannabinoid-related targets, including cannabinoid receptors (selectivity index: >25,000) and MGL, an enzyme involved in the deactivation of the endogenous cannabinoid ester, 2-AG (selectivity index: >7,500). Such a remarkable target discrimination was matched by a lack of overt cannabimimetic effects in vivo. Thus, at doses that almost abolished FAAH activity and substantially raised brain anandamide levels, UCM597 and its analog UCM532 did not evoke catalepsy, reduce body temperature or stimulate feeding, three key symptoms of cannabinoid intoxication in the rodent (Chaperon, F. et al., *Crit. Rev. Neurobiol.*, 13, 243-281 (1999)).

Nevertheless, the compounds did elicit marked anxiolytic-like responses, which paralleled their ability to inactivate FAAH and were attenuated by the CB1 receptor antagonist rimonabant.

Without being wed to theory, UCM597 and UCM532 selectively modulate anxiety-like behaviors by enhancing the tonic actions of anandamide on a subset of CB1 receptors, which may normally be engaged in controlling emotions. Forebrain sites that might be implicated in such actions include the basolateral amygdala, the anterior cingulate cortex and the prefrontal cortex, key elements of an "emotion circuit" (Cahill, L. et al., *Trends Neurosci.*, 21, 294-299 (1998)) that contains high densities of CB1 receptors (Herkenham, M. et al., *Proc. Natl. Acad. Sci. U.S.A.*, 87, 1932-1936 (1990); Glass, M. et al., *Neuroscience*, 77, 299-318 (1997)). Interestingly, CB1 receptors in these structures are exclusively localized to the axon terminals of a subpopulation of GABA-ergic interneurons, which also express the peptide cholecystokinin (CCK) (Katona, I. et al., *J. Neurosci.*, 21, 9506-9518 (2001); McDonald, A. J. et al., *Neuroscience*, 107, 641-652 (2001)).

In addition to their anxiolytic-like actions, UCM597 and UCM532 exerted moderate, but significant antinociceptive effects, which also were sensitive to CB1 receptor blockade. These findings are strikingly similar to those reported for mutant $FAAH^{-/-}$ mice (Cravatt, B. F. et al., *Proc. Natl. Acad. Sci. U.S.A.*, 98:9371-9376 (2001)) and underscore the emerging roles of anandamide in the intrinsic modulation of pain (Iversen, L. et al., *Curr. Opin. Pharmacol.*, 2:50-55 (2002)). Since emotional states may strongly influence pain sensation, it is possible that anxiolysis might have contributed to the antinociceptive effects of the FAAH inhibitors. Distinguishing the roles of these two components will require, however, further experimentation.

UCM597 and UCM532 increased brain anandamide levels without modifying those of the second endogenous cannabinoid, 2-AG. It is likely, therefore, that the pharmacological actions of these compounds, which are sensitive to the CB1 antagonist rimonabant, are primarily due to anandamide accumulation. But the FAAH inhibitors also produced large elevations in the levels of two anandamide analogs, palmitoylethanolamide and oleoylethanolamide, whose recently discovered biological effects are independent of CB1 receptors (Calignano, A. et al., *Nature*, 394:277-281 (1998); Rodriguez de Fonseca, F. et al. *Nature*, 414:209-212 (2001)).

Example 17

This example provides the FAAH inhibitory $IC_{50}$ values for over 50 compounds according to Formula I or Formula II. The results of testing the compounds are shown in Table 4.

Example 18

This example provides a more detailed 3D-QSAR analysis of O-aryl N-alkylcarbamic acid aryl esters and then relates such to the 3-dimensional structure of FAAH.

Recently, starting from the assumption that carbamic acid esters could act as active site-directed inhibitors of FAAH, a series of O-aryl-N-alkylcarbamic acid aryl esters were developed that irreversibly inhibit FAAH activity with good in vitro and in vivo potency, and as a result, exert anxiolytic effects in rats. The methods and results of this work are published in (Kathuria, S, et al., *Nat. Med.* 9, 76-81 (2003); Tarzia, G., et al., *J. Med. Chem.* 46, 2352-2360 (2003)) and incorporated herein by reference in its entirety. Notably, most of the compounds block FAAH, but not several other serine hydrolases, e.g. acetylcholinesterase and MGL, and do not bind to cannabinoid receptors. A preliminary SAR investigation, aimed at the definition of shape requirements for the lipophilic O-aryl moiety, showed that structures characterized by a non-linear shape led to an improvement of potency. The methods and results of this work are described in Tarzia, et al., *Med. Chem.* 46, 2352-2360 (2003) which is incorporated by reference in its entirety. More precisely, the curved molecules of the most potent inhibitors resembled that observed for the folded conformations of fatty acids in complexes with different proteins and for the so-called U-shaped conformation of anandamide, (Reggio, P. H., et al. *Chem. Phys. Lipids* 108, 15-35 (2000) which had been recently proposed as one possibly assumed at the $CB_1$ receptor binding site. (Barnett-Norris, J., et al., *J. Med. Chem.* 451, 3649-3659 (2002)). Moreover, the recently published crystal structure of a complex of FAAH and the inhibitor methyl arachidonyl fluorophosphonate (MAPF) (Bracey, M. H., *Science* 298, 1793-1796 (2002) revealed a folded conformation of the arachidonyl chain.

Figure 5:
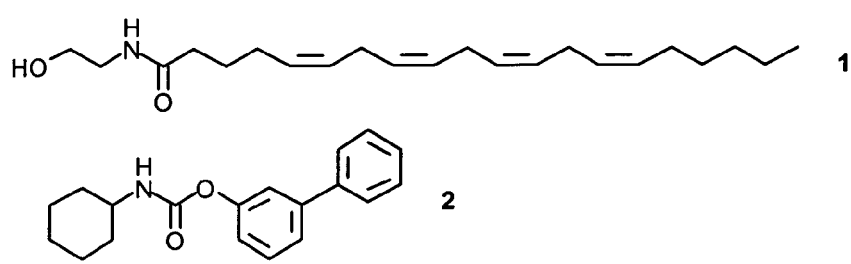
FIG. 5 sets forth the chemical structures of anandamide (1) and URB524 (2).

The 3D-QSAR analysis of O-aryl-N-alkylcarbamic acid aryl esters indicates that the space occupancy of a region corresponding to the meta position of an O-phenyl ring was positively correlated with inhibitor potency, thus suggesting its beneficial interaction with the enzyme binding site. The most potent compound found in this series was URB524 (2, FIG. 5), having an $IC_{50}$ value of 63 nM; To explore QSARs of carbamate FAAH inhibitors and optimizing their activity, compound based upon this compound as the starting point were tested to provide for a systematic exploration of the effect of phenyl substitution. As in the previous series only lipophilic groups had been introduced at the O— position of the carbamate, the series provided information only on the steric interactions occurring within the binding site. To further characterize the nature of possible interaction, a balanced set of substituents, with variation of their lipophilic and electronic properties, was introduced at the meta and para positions of the distal phenyl ring of URB524, since this moiety had been indicated as crucial by the cited 3D-QSAR model.

The experimental design for the exploration of substituent effects was set up in two steps. Firstly, a small set of substituents, having moderate size, was employed to test the sensibility of the meta and the para positions to lipophilic and electronic properties; the four substituents methyl, trifluoromethyl, amino and carbamoyl represented the four combinations of positive and negative levels for the π and σ ($\sigma_m$ or $\sigma_p$) descriptors; (van de Waterbeemd, H., et al. *J. Comput.-Aided Des.* 3, 111-132 (1989)); furthermore, a small (fluoro) and a big (cyclohexylcarbamoyloxy) substituents were added to this first explorative set. Having identified the more responsive position of the phenyl ring, as a second optimization step the series of substitutents were expanded seeking to maintain significant and independent variation among the variables describing lipophilic, electronic and steric properties of the substituents, which is a prerequisite to investigate QSARs by multiple regression analysis (MRA) (Box, G. E. P.; et al. *Statistics for Experimenters*, Wiley: New York 306-373 (1978); van de Waaterbeemd, H., et al. *Chemometric Methods in Molecular Design*, VCH Publishers Inc.: New York 49-62 (1995)).

Half-maximal concentrations ($IC_{50}$) for inhibition of FAAH activity in rat brain membranes, using [$^3$H]anandamide as a substrate,[18] by compounds 3a-z are reported in Table 5.

The first limited set of substituents at the ending phenyl ring (3a-l) revealed that the meta position was much more promising for potency optimization. In fact, though the 3'-methyl (3h) and 3'-amino (3j) derivatives resulted in a compound as potent as the parent compound for FAAH inhibition, the 3'-carbamoyl one (3i) was more potent by an order of magnitude; on the other hand, all the para-substituted compounds were less potent than the parent compound, only the 4'-fluoro derivative (3e) having a comparable $IC_{50}$ value.

The set of substituents at the meta position was therefore expanded to explore statistical relationships between substituent properties and inhibitor potency. Therefore, 12 additional substituents (3m-z in Table 5) were selected to enlarge the space representing lipophilic, steric and electronic properties; some of them were chosen for their similarity to the carbamoyl group (i.e., the sulphamoyl group in 3r) or to parts of it (i.e., the acetyl, aminomethyl, or hydroxymethyl group in 3s, 3z, or 3v, respectively). The 19 substituents, including H, reported in Table 6, had large variation in lipophilicity (almost 4 π unities) and steric bulk, both practically uncorrelated to electronic effects (r with $\sigma_m$ of −0.19 and −0.16, respectively); they still had some correlation between lipophilic (π) and steric (MR) descriptors (r=0.63), due to the known difficulty to obtain big hydrophilic substituents.

TABLE 5

Inhibitory Potencies ($IC_{50}$) of Tested Compounds on FAAH activity.

| Cpds | $R^1$ | $R^2$ | $IC_{50}$ (nM) ± S.E.M. |
|---|---|---|---|
| URB524 | H | H | 63 ± 9 |
| 3a | H | $CF_3$ | 1,587 ± 148 |
| 3b | H | $CH_3$ | 155.4 ± 21 |
| 3c | H | $C(O)NH_2$ | 5,909 ± 951 |
| 3d | H | $NH_2$ | 360 ± 59 |
| 3e | H | F | 64.95 ± 14.00 |
| 3f | H | C(O)NHC(O)NHc-$C_6H_{11}$ | 3,017 ± 688 |
| 3g | $CF_3$ | H | 145.7 ± 16.0 |
| 3h | $CH_3$ | H | 61.75 ± 19.00 |
| 3i | $C(O)NH_2$ | H | 4.6 ± 1.6 |
| 3j | $NH_2$ | H | 64.6 ± 9.0 |
| 3k | F | H | 96.6 ± 4.0 |
| 3l | OC(O)NHc-$C_6H_{11}$ | H | 361 ± 137 |
| 3m | $C_6H_5O$ | H | 420 ± 86 |
| 3n | $C_6H_5$ | H | 565 ± 42 |
| 3o | $CH_2C_6H_5$ | H | 1,857 ± 57 |
| 3p | n-$C_3H_7$ | H | 110 ± 16 |
| 3q | $NO_2$ | H | 49.6 ± 2.0 |
| 3r | $SO_2NH_2$ | H | 26.5 ± 4.5 |
| 3s | $C(O)CH_3$ | H | 9.1 ± 0.5 |
| 3t | CN | H | 33.9 ± 7.0 |
| 3u | OH | H | 8.65 ± 0.10 |
| 3v | $CH_2OH$ | H | 8.67 ± 0.90 |
| 3w | $(CH_2)_2OH$ | H | 18.7 ± 4.5 |
| 3z | $CH_2NH_2$ | H | 21,177 ± 7,277 |

TABLE 6

Observed and Calculated $pIC_{50}$ Values for FAAH Inhibition of the Meta-substituted Derivatives Included in QSAR Analysis.

| Cpds | R | $pIC_{50}$ obsd | $pIC_{50}$ calcd |
|---|---|---|---|
| URB524 | H | 7.20 | 7.28 |
| 3g | $CF_3$ | 6.84 | 6.83 |
| 3h | $CH_3$ | 7.21 | 6.99 |
| 3i | $C(O)NH_2$ | 8.34 | 7.99 |
| 3j | $NH_2$ | 7.19 | 7.86 |
| 3k | F | 7.02 | 7.19 |
| 3l | OC(O)NHc-$C_6H_{11}$ | 6.44 | 6.74 |
| 3m | $C_6H_5O$ | 6.38 | 6.24 |
| 3n | $C_6H_5$ | 6.25 | 6.30 |
| 3o | $CH_2C_6H_5$ | 5.73 | 6.28 |
| 3p | n-$C_3H_7$ | 6.96 | 6.50 |
| 3q | $NO_2$ | 7.30 | 7.40 |
| 3r | $SO_2NH_2$ | 7.58 | 8.15 |
| 3s | $C(O)CH_3$ | 8.04 | 7.53 |
| 3t | CN | 7.47 | 7.54 |
| 3u | OH | 8.06 | 7.59 |
| 3v | $CH_2OH$ | 8.06 | 7.76 |
| 3w | $(CH_2)_2OH$ | 7.73 | 7.64 |

Figure 6:
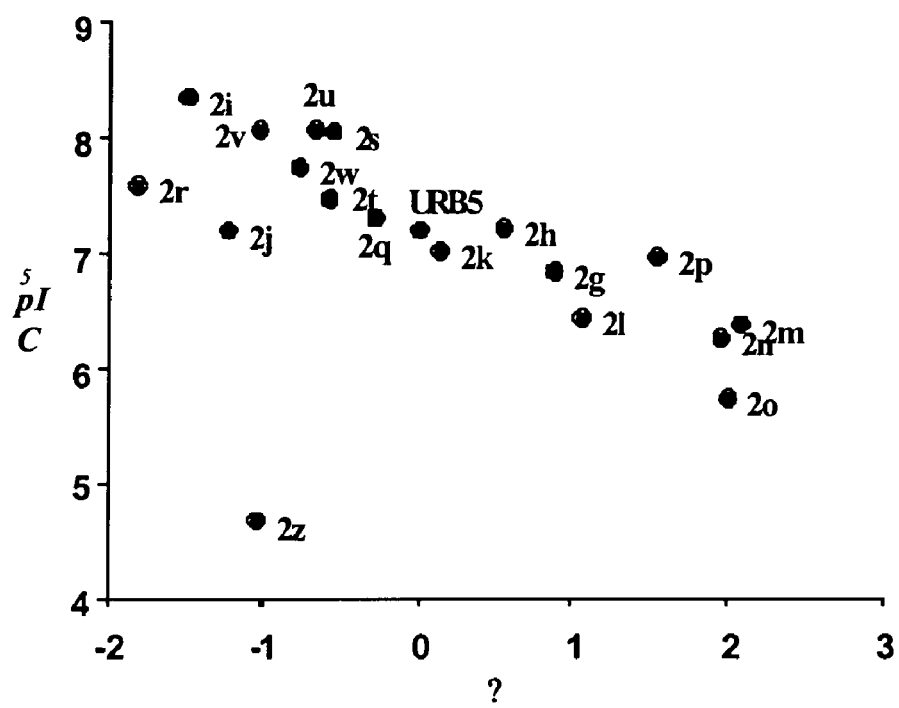
FIG. 6 provides a plot of FAAH inhibition potency (pIC$_{50}$) vs lipophilicity ($\pi$) for URB524 and its meta-substituted derivatives.

Multiple regression analysis (MRA) applied to the data set composed by maximum 3 active variable, selected among 8 common physico-chemical descriptors (p, $\sigma_m$, F, R, MR, L, $B_1$, $B_5$) and the square of π, gave no significant model. However, a simple plot of the potency variable, $pIC_{50}$, vs lipophilicity (FIG. 6) revealed that a clear relationship was observable, but the methylamino derivative 3z resulted an outlier; this could be attributed to its basicity, making it the only compound with a large prevalence of protonated, cationic species at neutral pH. Omitting 3z from the regression set, the negative correlation between lipophilicity and potency could be described by the linear model reported in equation 1; the $pIC_{50}$ values calculated by equation 1 are reported in Table 6.

$$pIC_{50} = -0.49(\pm 0.07)\pi + 7.26(\pm 0.09) \quad (1)$$

n=18 (URB524, 3g-w) $r^2$=0.74 s=0.37 F=46.0 $q^2$=0.66 SDEP=0.40

This negative correlation is characteristic of the meta position, since the limited set of para substituents showed, on the same scales, a parabolic relationships described by the regression equation 2.

$$pIC = 0.52(\pm 0.12)\pi - 1.20(\pm 0.14)\pi^2 + 7.33(\pm 0.14) \quad (2)$$

n=7 (URB524, 3a-f) $r^2$=0.95 s=0.22 F=37.8 $q^2$=0.80 SDEP=0.33

While the set of para-substituted compounds was too small to consider more complicated models, the 18-compound set of meta-substituted derivatives represented a good set for a detailed QSAR investigation; moreover, the negative correlation with lipophilicity appeared perplexing, as our previous results supported the hypothesis that the biphenyl moiety would mimic the arachidonoyl chain in its lipophilic FAAH binding site. However, no MRA model including up to 5 variables had statistical quality better or comparable to that of equation 1; only the inclusion of an hydrogen bond indicator variable (HB), set to 1 for substituents able to give hydrogen bonds and to 0 in other cases, allowed the detection of an alternative model (equation 3) with comparable descriptive ($r^2$) and predictive ($q^2$) power, indicating that potency increase was negatively correlated to the steric bulk (MR) of the substituents, but the polar ones had an average 0.8 $pIC_{50}$ units more than the apolar ones.

$$pIC_{50} = -0.046(\pm 0.009)MR + 0.80(\pm 0.18)HB + 7.29 (\pm 0.17) \quad (3)$$

n=18 (URB524, 3g-w) $r^2$=0.76 s=0.37 F=23.2 $q^2$=0.68 SDEP=0.39

Although this model was not statistically better than equation 1, it could provide a possible interpretation for the positive effect of substituent hydrophilicity within a putative lipophilic binding pocket, attributing this behaviour to the formation of hydrogen bonds between the meta substituent and some polar atoms of the enzyme, not available for the para substituents.

Figure 7:
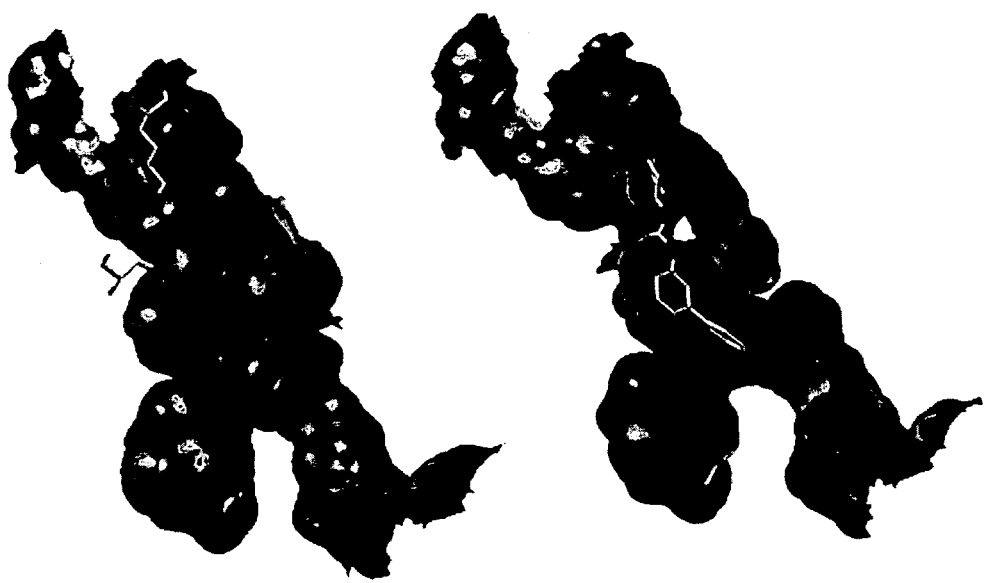
FIG. 7 is a drawing of the 3-D surface of the catalytic channel inside FAAH, colored by residue lipophilicity. Hydrophilic regions are colored in blue, lipophilic ones in brown.
Figure 8:
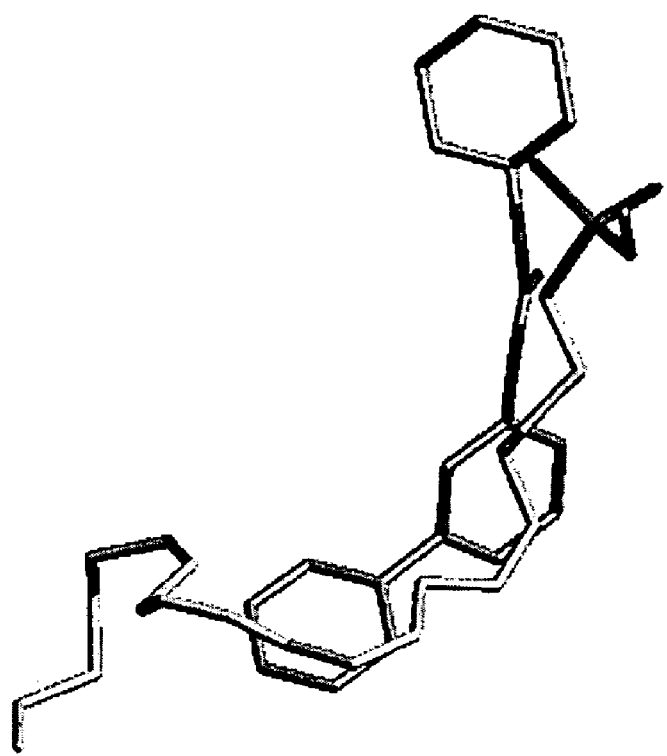
FIG. 8 represents a superposition of the biphenyl fragment of URB524 to the arachidonyl chain of MAPF co-crystallyzed with FAAH.
Figure 9:
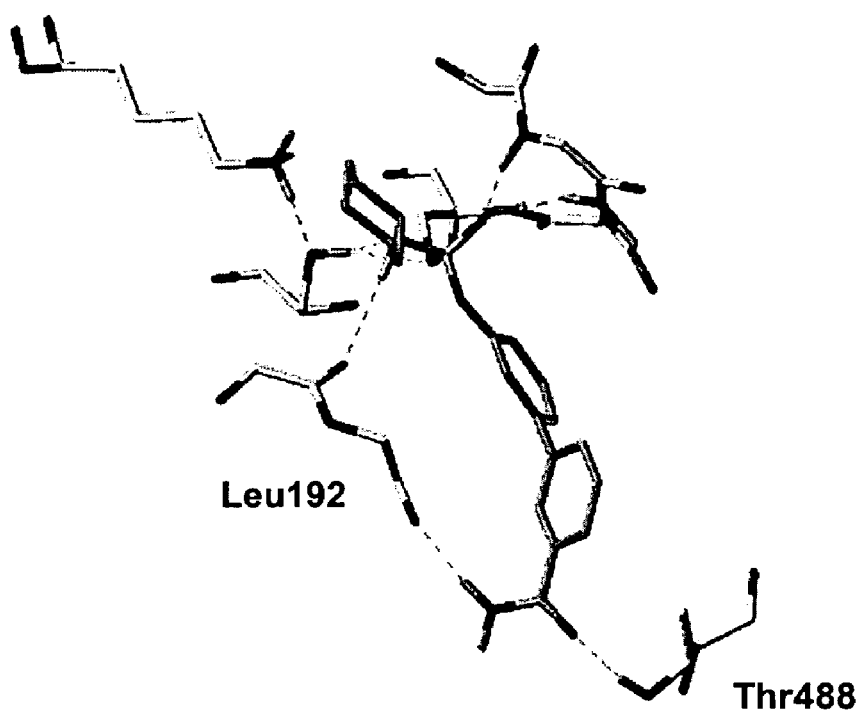
FIG. 9 illustrates docking of URB597 into the FAAH binding site. The hydrogen bonds of the carbamoyl group with the enzyme are evidenced in yellow.

The crystal structure for the FAAH bound to a covalent arachidonyl-phosphonate inhibitor[22] has recently been reported by others. Without being wed to theory, the docking of our inhibitors within the enzyme active site and molecular dynamics simulations can explain the role of the U and V groups or R groups with respect to the subject compounds surprising ability to inhibit the enzyme. It is thought that the binding site of the aforementioned arachidonyl inhibitor is part of a channel spanning the whole enzyme, represented in FIG. 7; the catalytic Ser241 is placed in the middle of this channel, which extends towards the membrane on one side (bottom in FIG. 7, left) and the cytosol on the other. This channel has a complex topography, with a hydrophilic surface in correspondence of the catalytic site, surrounded by lipophilic surfaces in the two directions. That pointing towards the membrane, which is occupied by the arachidonyl chain of the phosphonate inhibitor, forms a lipophilic bulge allocating the terminal atoms of this inhibitor and a narrow tunnel having a hydrophilic "ridge," which could be used by the hydrophilic head of OEA to approach the catalytic site, while moving along from the membrane. Our molecular docking showed that the biphenyl moiety of URB524 could, after deletion of the phosphonate inhibitor, occupy the space of the arachidonyl chain, with the meta position of the distal phenyl ring pointing exactly towards the hydrophilic ridge (see FIG. 7). The superposition of a minimum-energy conformation of the biphenyl moiety to the arachidonyl chain, in the conformation found for the MAPF/FAAH complex, highlights the steric similarity with the first two double bonds, thus supporting our hypothesis (see FIG. 8). Interestingly, all the polar meta substituents were able to undertake hydrogen bonds with some polar residue of the hydrophilic ridge. The heuristic model described by of equations 1 and 3 indicates that the inhibitor potency of meta substituted biphenylyl carbamates is negatively correlated to lipophilicity because, although the biphenyl scaffold can be located in the lipophilic region of space generally occupied by the first atoms of fatty acid chain, substituents at the meta position of the distal phenyl ring can interact to form hydrogen bonds with a hydrophilic wall of a narrow tunnel within the enzyme. These results indicate that moieties interacting via hydrogen bonding with the subject hydrophilic ridge can contribute importantly to the activity of a FAAH inhibitor. Consistent with this prediction from our model, docking of the most potent compound in the biphenyl carbamate series, 31 (URB 597), led to a solution which showed the possibility that the carbamoyl group of URB 597 undertakes two hydrogen bonds with the enzyme: one as an HB-acceptor, with the hydroxyl group of Thr488, and the second as an HB-donor, with the backbone carbonyl of Leu192 (FIG. 9). Altogether our results show that compounds primarily interacting with the hydrophobic channel rather than the catalytic site can be high potency inhibitors of FAAH.

Each publication, patent application, patent, and other reference cited in any part of the specification is incorporated by reference in its entirety to the extent that it is not inconsistent with the present disclosure.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 1

Structures of selected carbamate inhibitors of FAAH activity

| | R | $R_1$ | $IC_{50}$(nM) | S.E.M. |
|---|---|---|---|---|
| 1 | naphthyl | $CH_3$ | >100,000 | |

TABLE 1-continued

Structures of selected carbamate inhibitors of FAAH activity $$R-O-C(=O)-NH-R_1$$

| # | R | R₁ | IC₅₀(nM) | S.E.M. |
|---|---|---|---|---|
| 2 | 2-naphthyl | CH₃ | 18,600 | 708 |
| 3 | 2-naphthyl | c-C₆H₁₁ | 324 | 31 |
| 4 | 4-(benzyloxy)phenyl | n-C₄H₉ | 396 | 63 |
| 5 | 3-biphenyl | c-C₆H₁₁ | 63 | 9 |
| 6 | 3-(aminocarbonyl)biphenyl | c-C₆H₁₁ | 4.6 | 1.6 |
| 7 | 4-(benzyloxy)phenyl | p-C₆H₁₀F | >100,000 | |

TABLE 2

Analysis of selected FAAH inhibitors in vitro

| Compound | AChE | SI | BCh | SI | MGL | SI | AT | SI | CB1 | SI | CB2 | SI |
|---|---|---|---|---|---|---|---|---|---|---|---|---|
| Fenoxbutamate | >100 | ≧333 | >100 | ≧333 | >30 | ≧100 | >300 | ≧1000 | >300 | ≧1000 | >300 | ≧1000 |
| Carbifenamate | >100 | ≧25000 | ≧100 | ≧25000 | >30 | ≧7500 | >30 | ≧7500 | >100 | ≧25000 | >100 | ≧25000 |

TABLE 3

Selectivity of various compounds for Inhibition of FAAH and Cholinesterase

| Compound | Name of the compound | Amidohydrolase IC₅₀ (μM) | Cholinesterase IC₅₀ (μM) |
|---|---|---|---|
| PL #1 | 1-phenyl-N-piperidine carboxylate | >30 | >30 |
| PL #2 | 4-tolyl N-ethylcarbamate | >30 | >30 |
| PL #3 | 6-bromo-2-napthylyl N-butylcarbamate | 0.76 | >30 |
| PL #4 | 2-napthyl N-methyl carbamate | 18.7 | >30 |
| PL #5 | 4-biphenyl N-cylcohexylcarbamate | 2.3 | >30 |
| PL #6 | p-tolyl-N-cyclohexylcarbamate | 5.4 | >30 |
| PL #7 | 4-(benzyloxy) phenyl N-butyl carbamate | 0.4 | >30 |
| PL #8 | 4-(benzyloxy) phenyl N-(4-fluorophenyl)carbamate | >30 | >30 |
| PL #9 | hexyl N-cyclohexyl carbamate | 3.7 | >30 |
| PL #10 | 3-chloro-4-biphenyl N-tertbutylcarbamate | >30 | >30 |
| PL #11 | 2-napthyl N-cyclohexylcarbamate | 0.33 | >30 |
| PL #12 | 4-fluorophenyl N-butyl carbamate | 11.5 | >30 |
| PL #13 | ethyl benzylformate | >30 | >30 |
| PL #14 | ethyl-2-oxo-4-phenylbutyrate | 25.6 | >30 |
| PL #15 | 2,3-dihydro-2,2-dimethyl-7-benzofuranol N-methylcarbamate | >30 | 0.56 |
| PL #16 | physostigmine sulfate | >30 | 0.58 |
| PL #17 | O-butyl 4-(4′methoxyphenoxycarbonyl)-phenyl carbonate | 9.1 | >30 |
| PL #18 | carbaryl | >30 | 3.1 |

TABLE 4

| PL compounds | | Inhibition of Amidohydrolase IC$_{50}$ (μM) | Inhibition of Cholinesterase IC$_{50}$ (μM) | CB1 and CB2 Receptor Binding EC$_{50}$ (μM) |
|---|---|---|---|---|
| PL#1 | 1-phenyl-N-piperidinecarboxylate | >30 | | |
| PL#2 | 4-tolyl N-ethylcarbamate | >30 | | |
| PL#3 | 6-bromo-2-naphtyhyl N-butylcarbamate | 0.76 | | |
| PL#4 | 2-naphtyl-N-methylcarbamate | 18.6 | | |
| PL#5 | 4-biphenyl N-cyclohexylcarbamate | 2.3 | | |
| PL#6 | p-tolyl-N-cyclohexyl carbamate | 5.4 | | |
| PL#7 | 4-(benzyloxy) phenyl N-butylcarbamate (UCM 532) | 0.3 | | |

TABLE 4-continued

| PL compounds | Inhibition of Amidohydrolase IC$_{50}$ (μM) | Inhibition of Cholinesterase IC$_{50}$ (μM) | CB1 and CB2 Receptor Binding EC$_{50}$ (μM) |
|---|---|---|---|
| PL#8 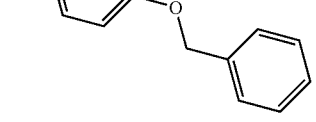 4-(benzyloxy) phenyl N-(4-fluorophenyl)carbamate (UCM 531) | >30 | | |
| PL#9 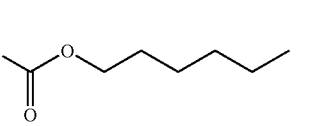 hexyl-N-cyclohexyl carbamate | 3.7 | | |
| PL#10 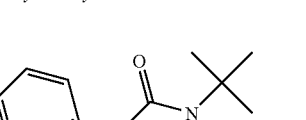 3-chloro-4-biphenylyl N-tert-butylcarbamate | >30 | | |
| PL#11 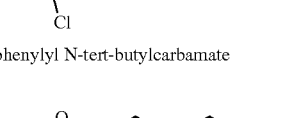 2-naphthyl N-cyclohexylcarbamate | 0.33 | | |
| PL#12 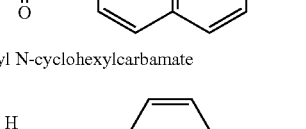 4-fluorophenyl N-butylcarbamate | 11.5 | | |
| PL#13 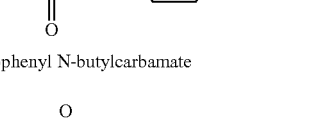 ethyl benzylformate | >30 | | |
| PL#14 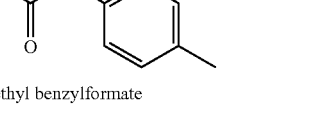 ethyl-2-oxo-4-phenylbutyrate | 25.6 | | |
| PL#15 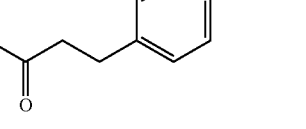 2,3-dihyrdo-2,2-dimethyl-7-benzofumaol N-methylcarbamate | >30 | | |

TABLE 4-continued
| PL compounds | Inhibition of Amidohydrolase IC$_{50}$ (μM) | Inhibition of Cholinesterase IC$_{50}$ (μM) | CB1 and CB2 Receptor Binding EC$_{50}$ (μM) |
|---|---|---|---|
| PL#16 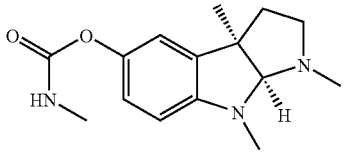 (-)-Physostigmine sulfate | | >30 | |
| PL#17 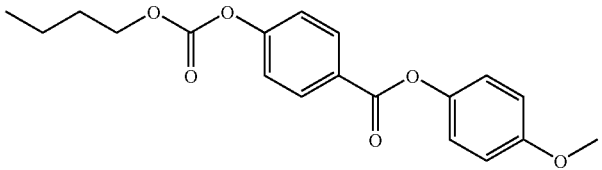 O-butyl 4-(4'-methoxyphenoxycarbonyl)-phenyl carbonate | | 9.1 | |
| PL#18 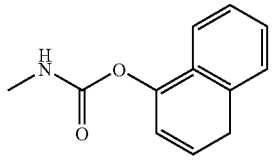 carbaryl | | >30 | |
| PL#19 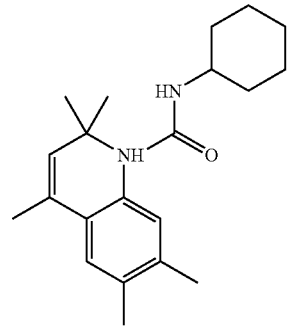 CNC-523605 | | >30 | |
| PL#20 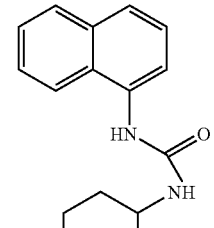 CNC-540335 | | >30 | |

TABLE 4-continued
| PL compounds | Inhibition of Amidohydrolase IC$_{50}$ (μM) | Inhibition of Cholinesterase IC$_{50}$ (μM) | CB1 and CB2 Receptor Binding EC$_{50}$ (μM) |
|---|---|---|---|
| PL#21 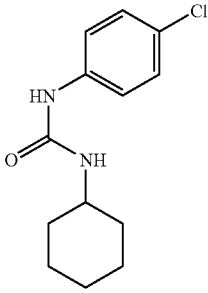 CNC-541078 | | | >30 |
| PL#22 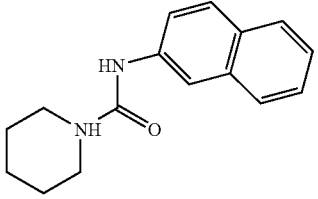 CNC-608455 | | | >30 |
| PL#23 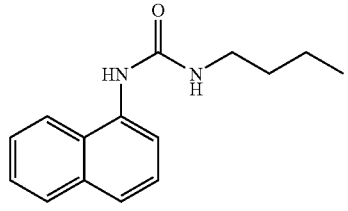 CNC-1072849 | | | >30 |
| PL#24 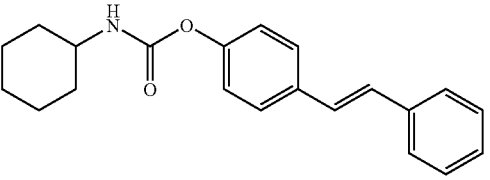 (UCM 522) | | | 3.3 |
| PL#25 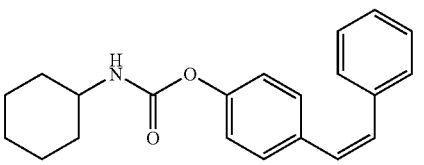 (UCM 523) | | | 0.24 |
| PL#26 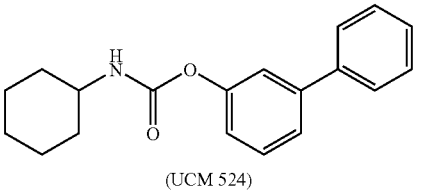 (UCM 524) | | | 0.06 |

TABLE 4-continued
| PL compounds | Inhibition of Amidohydrolase IC$_{50}$ (µM) | Inhibition of Cholinesterase IC$_{50}$ (µM) | CB1 and CB2 Receptor Binding EC$_{50}$ (µM) |
|---|---|---|---|
| PL#27 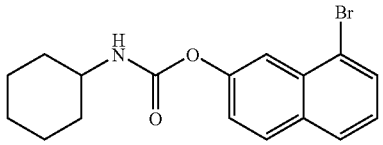 (UCM 525) | 0.17 | | |
| PL#28 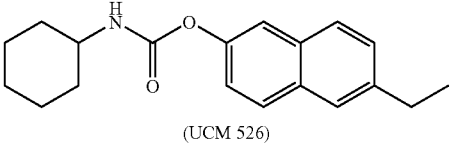 (UCM 526) | 3.0 | | |
| PL#29 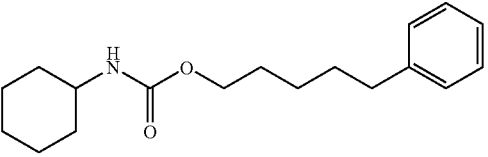 (UCM 527) | >30 | | |
| PL#30 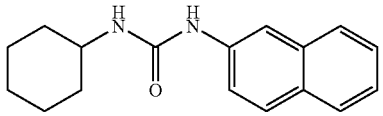 (UCM 528) | >30 | | |
| #31. 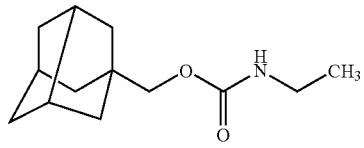 CNC-256597 | >30 | | |
| #32 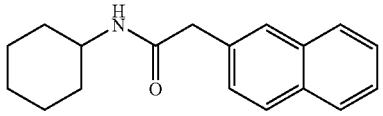 (UCM 533) | >30 | | |
| #33 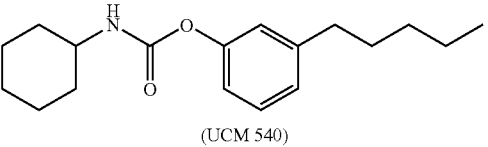 (UCM 540) | 0.22 | | |

TABLE 4-continued
| PL compounds | Inhibition of Amidohydrolase IC$_{50}$ (μM) | Inhibition of Cholinesterase IC$_{50}$ (μM) | CB1 and CB2 Receptor Binding EC$_{50}$ (μM) |
|---|---|---|---|
| #34 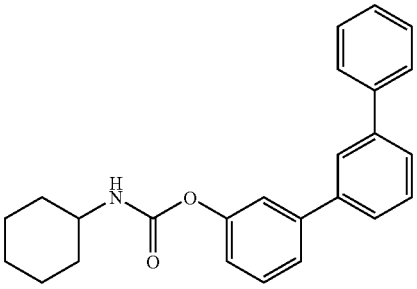 (UCM 566) | 0.56 | | |
| #35 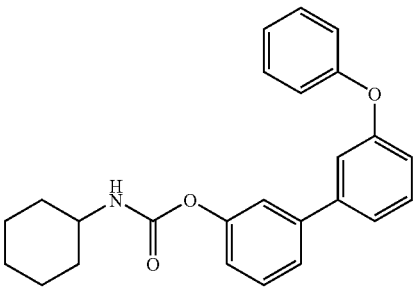 (UCM 564) | 2.6 | | |
| #36 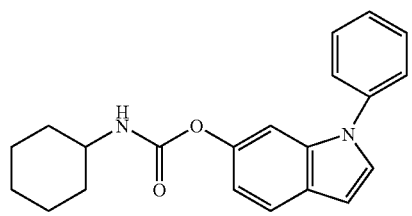 (UCM 561) | 1.4 | | |
| PL#37 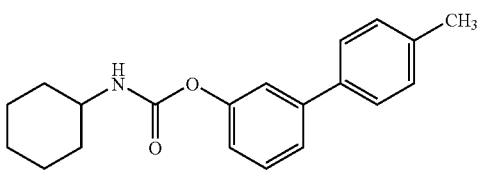 (UCM 588) | 0.23 | | |
| PL#38 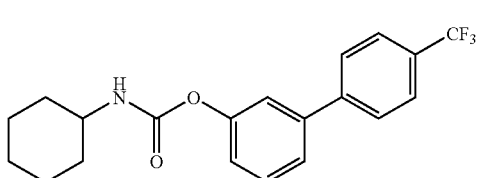 (UCM 589) | 1.6 | | |
| PL#39 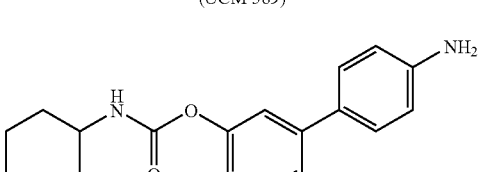 (UCM 590) | 0.51 | | |

TABLE 4-continued
| PL compounds | Inhibition of Amidohydrolase IC$_{50}$ (µM) | Inhibition of Cholinesterase IC$_{50}$ (µM) | CB1 and CB2 Receptor Binding EC$_{50}$ (µM) |
|---|---|---|---|
| PL#40 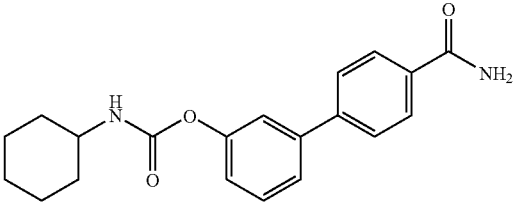 (UCM 591) | | | >10 |
| PL#41 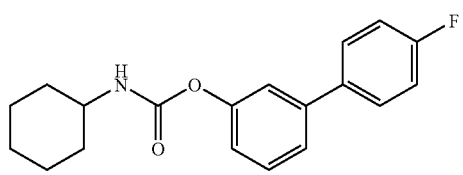 (UCM 592) | | | 0.09 |
| PL#42 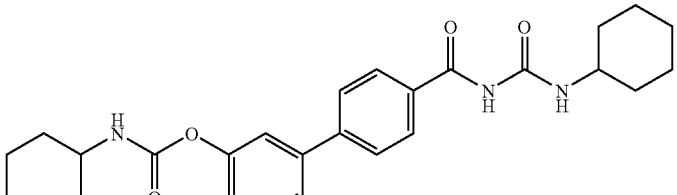 (UCM 593) | | | ~30 |
| PL#43 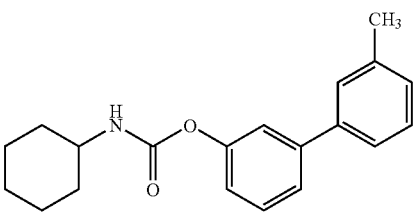 (UCM 594) | | | 0.1 |
| PL#44 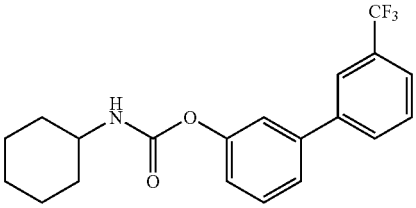 (UCM 595) | | | 0.13 |
| PL#45 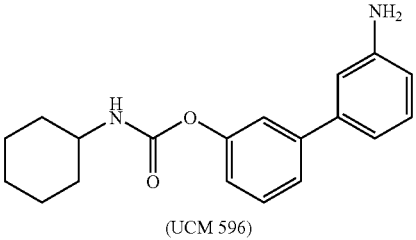 (UCM 596) | | | 0.06 |

TABLE 4-continued
| PL compounds | Inhibition of Amidohydrolase IC$_{50}$ (μM) | Inhibition of Cholinesterase IC$_{50}$ (μM) | CB1 and CB2 Receptor Binding EC$_{50}$ (μM) |
|---|---|---|---|
| PL#46 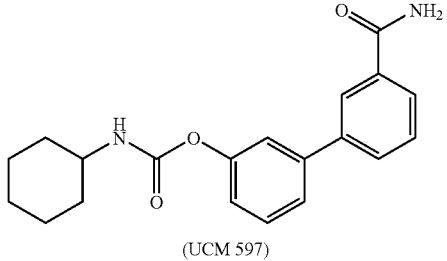 (UCM 597) | 0.004 | | |
| PL#47 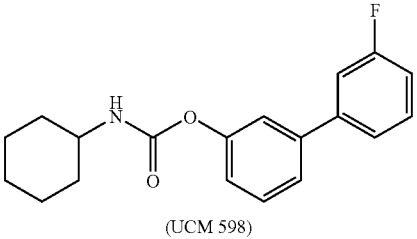 (UCM 598) | 0.092 | | |
| PL#48 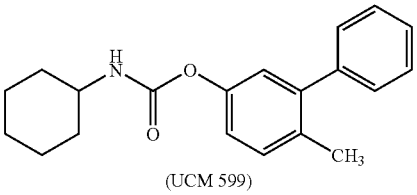 (UCM 599) | 0.2 | | |
| PL#49 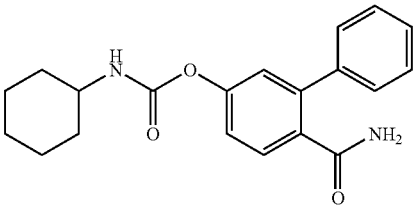 (UCM 600) | 0.2 | | |
| PL#50 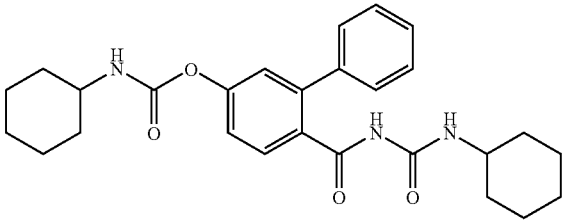 (UCM 601) | 3.1 | | |
| PL#51 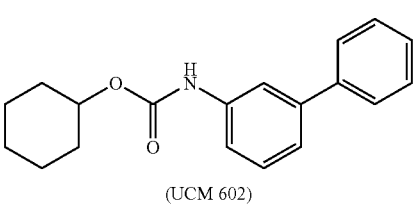 (UCM 602) | >30 | | |

TABLE 4-continued
| PL compounds | Inhibition of Amidohydrolase IC$_{50}$ (μM) | Inhibition of Cholinesterase IC$_{50}$ (μM) | CB1 and CB2 Receptor Binding EC$_{50}$ (μM) |
|---|---|---|---|
| PL#52 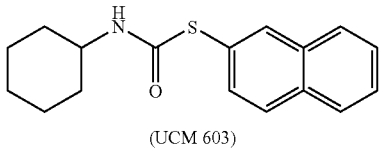 (UCM 603) | 15 | | |
| PL#53 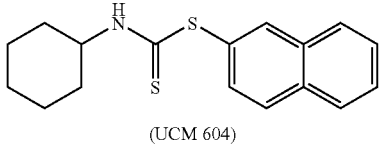 (UCM 604) | >30 | | |
| PL#54 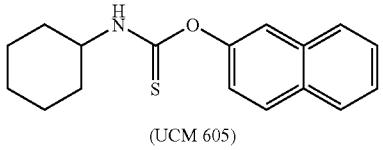 (UCM 605) | >30 | | |
| PL#55 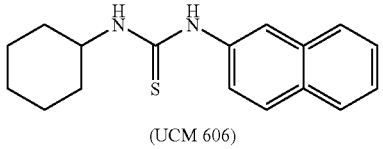 (UCM 606) | >30 | | |
| PL#56 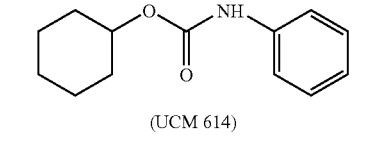 (UCM 614) | 3.1 | | |
| PL#57 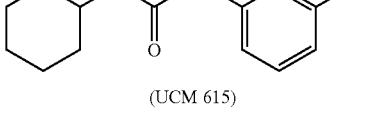 (UCM 615) | 0.8 | | |
| PL#58 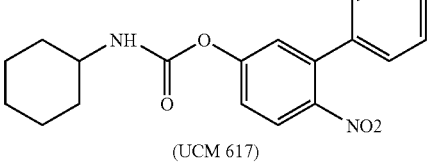 (UCM 617) | >30 | | |
| PL#59 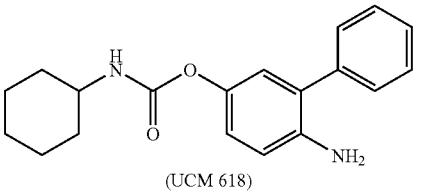 (UCM 618) | 0.05 | | |

TABLE 4-continued

| PL compounds | Inhibition of Amidohydrolase IC$_{50}$ (µM) | Inhibition of Cholinesterase IC$_{50}$ (µM) | CB1 and CB2 Receptor Binding EC$_{50}$ (µM) |
|---|---|---|---|
| PL#60 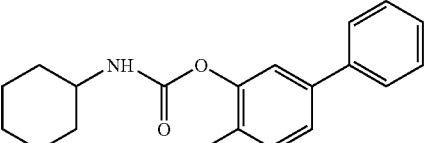 (UCM 619) | >30 | | |
| PL#61 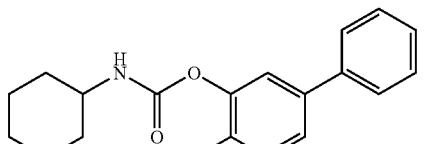 (UCM 620) | >30 ? | | |
| PL#62 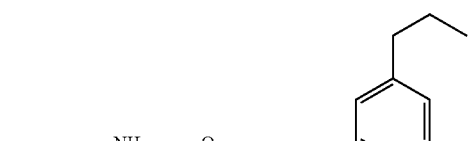 (UCM 621) | 0.08 | | |

What is claimed is:

1. A method of inhibiting fatty acid amide hydrolase activity in a mammal having pain, anxiety or depression, said method comprising administering to the mammal a therapeutically effective amount of a compound of the formula

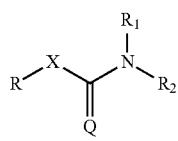

wherein

X is O or S;

Q is O or S;

R is unsubstituted naphthyl or naphthyl substituted with halogen, —OR', —NR'R", —SR', —OC(O)R', —C(O)R', —CO$_2$R', —CONR'R", —OC(O)NR'R", —NR"C(O)R', —NR'—C(O)NR"R''', —NR"C(O)$_2$R', —S(O)R', —S(O)$_2$R', —S(O)$_2$NR'R", —CN and —NO$_2$, —R', fluoro(C$_1$-C$_4$)alkoxy, or fluoro(C$_1$-C$_4$)alkyl, wherein R', R", R''' and R'''' are preferably independently selected from hydrogen and (C$_1$-C$_8$)alkyl, and R$_1$ and R$_2$ are independently selected from the group consisting of H, substituted or unsubstituted alkyl, substituted or unsubstituted cycloalkyl, wherein the substituents are independently selected from —OR', =O, =NR', =N—OR', —NR'R", —SR', -halogen, —OC(O)R', —C(O)R', —CO$_2$R', —CONR'R", —OC(O)NR'R", —NR"C(O)R', —NR'—C(O)NR"R''', —NR"C(O)$_2$R', —S(O)R', —S(O)$_2$R', —S(O)$_2$NR'R", —CN and —NO$_2$; wherein R', R", R''' and R'''' are defined as above;

and the pharmaceutically acceptable salts thereof, and whereby the anxiety, pain, or depression is treated.

2. The method of claim 1, wherein the mammal is human.

3. The method of claim 1, wherein the compound is administered orally.

4. The method of claim 1, wherein R$_2$ is H.

5. The method of claim 1, wherein the cycloalkyl is C$_3$-C$_8$ cycloalkyl.

6. The method of claim 4, wherein R$_1$ is methyl, ethyl, n-propyl, i-propyl, n-butyl, sec-butyl, tert-butyl, pentyl, hexyl, cyclopentyl, cyclohexyl, cycloheptyl, cyclopentenyl, cyclohexenyl, or cycloheptenyl.

7. The method of claim 6, wherein R$_1$ is cyclohexyl.

8. The method of claim 1 wherein the naphthyl is substituted with halogen or alkyl.

9. The method of claim 1 wherein the naphthyl is substituted with fluoro(C$_1$-C$_4$)alkyl.

10. The method of claim 1, wherein X is O and Q is O.

11. The method of claim 6, wherein X is O and Q is O.

12. The method of claim 7, wherein X is O and Q is O.

13. The method of claim 1, wherein the naphthyl is substituted.

14. The method of claim 6, wherein the naphthyl is substituted.

15. The method of claim 6, wherein the naphthyl is substituted with halo, alkyl, or fluoro(C$_1$-C$_4$)alkyl.

16. The method of claim 1 wherein the compound is

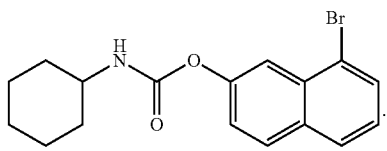

17. The method of claim 1, wherein the subject has pain.
18. The method of claim 17, wherein X is O and Q is O.
19. The method of claim 17, wherein $R_2$ is H.
20. The method of claim 19, wherein $R_1$ is methyl, ethyl, n-propyl, i-propyl, n-butyl, sec-butyl, tert-butyl, pentyl, hexyl, cyclopentyl, cyclohexyl, cycloheptyl, cyclopentenyl, cyclohexenyl, or cycloheptenyl.
21. The method of claim 19, wherein the naphthyl is substituted with halo, alkyl, or fluoro($C_1$-$C_4$)alkyl.
22. The method of claim 21, wherein $R_1$ is cyclohexyl.
23. The method of claim 1, wherein the mammal has anxiety.

* * * * *